(12) United States Patent
Bock et al.

(10) Patent No.: US 8,323,634 B2
(45) Date of Patent: Dec. 4, 2012

(54) STABLE FORMULATIONS OF HIGHLY CONCENTRATED RECOMBINANT HUMAN ALBUMIN-HUMAN GRANULOCYTE COLONY STIMULATING FACTOR

(75) Inventors: Jason Benjamin Bock, North Potomac, MD (US); Xia Luo, Rockville, MD (US)

(73) Assignee: Teva Pharmaceutical Industries Ltd. (IL)

(*) Notice: Subject to any disclaimer, the term of this patent is extended or adjusted under 35 U.S.C. 154(b) by 159 days.

(21) Appl. No.: 12/688,655

(22) Filed: Jan. 15, 2010

(65) Prior Publication Data

US 2010/0297062 A1 Nov. 25, 2010

Related U.S. Application Data

(60) Provisional application No. 61/145,436, filed on Jan. 16, 2009, provisional application No. 61/145,440, filed on Jan. 16, 2009.

(51) Int. Cl.
*A61K 45/00* (2006.01)
*C07K 14/535* (2006.01)
*C12P 21/02* (2006.01)

(52) U.S. Cl. .................. 424/85.1; 424/192.1; 435/69.5; 435/69.7; 530/351; 530/413

(58) Field of Classification Search .................. None
See application file for complete search history.

(56) References Cited

U.S. PATENT DOCUMENTS

| | | | |
|---|---|---|---|
| 5,637,504 A | 6/1997 | Hinchliffe et al. | |
| 5,665,863 A | 9/1997 | Yeh | |
| 7,041,478 B2 | 5/2006 | Fleer et al. | |
| 7,229,645 B2 * | 6/2007 | Maa et al. | 424/489 |
| 7,435,410 B2 | 10/2008 | Fleer et al. | |
| 7,592,010 B2 | 9/2009 | Rosen et al. | |
| 2003/0022308 A1 | 1/2003 | Fleer et al. | |
| 2003/0118612 A1 | 6/2003 | Nissen et al. | |
| 2004/0063635 A1 | 4/2004 | Yu et al. | |
| 2007/0244047 A1 | 10/2007 | Rosen et al. | |
| 2008/0153751 A1 | 6/2008 | Rosen et al. | |
| 2008/0181895 A1 | 7/2008 | Lal et al. | |
| 2010/0227818 A1 | 9/2010 | Bock et al. | |

FOREIGN PATENT DOCUMENTS

| | | |
|---|---|---|
| EP | 0 330 451 | 8/1989 |
| EP | 0 361 991 | 4/1990 |
| EP | 0 286 424 | 3/1994 |
| WO | WO 93/15199 | 10/1993 |
| WO | WO 03/076567 A2 | 9/2003 |
| WO | WO 2004/082640 A2 | 9/2004 |
| WO | WO 2005/003296 A2 | 1/2005 |
| WO | WO 2007/021494 A2 | 2/2007 |

OTHER PUBLICATIONS

Paige et al., Prolonged circulation of recombinant human Granulocyte-Colony Stimulating Factor by covalent linkage to albumin through a heterobifunctional polyethylene glycol, Pharmaceutical Res., 12, 1883-1888, 1995.*

Written Opinion for related International Patent Application No. PCT/US2010/021235, dated Jul. 15, 2010.
Altschul et al., "Issues in Searching Molecular Sequence Databases," *Nature Genetics*, 6, pp. 119-129 (1994).
Altschul, "A Protein Alignment Scoring System Sensitive at All Evolutionary Distances," *J. Mol. Evol.* 36, pp. 290-300 (1993).
Ausubel, F. M. et al., eds., "Current Protocols in Molecular Biology," vol. I, *Green Publishing Associates, Inc. and John Wiley & Sons, Inc., New York* at pp. 6.3.1-6.3.6 and 2.10.3), (1989).
Bowie, et al., "Deciphering the Message in Protein Sequences: Tolerance to Amino Acid Substitutions," *Science*, vol. 247, pp. 1306-1310 (1990).
Brutlag et al., "Improved Sensitivity of Biological Sequence Database Searches," *Comp. App. Biosci.*, 6, pp. 237-245 (1990).
Cleland et al., "The Development of Stable Protein Formulations: A Close Look at Protein Aggregation, Deamidation, and Oxidation," *Crit. Ref. Therapeutic Drug Carrier Systems*, 10, pp. 307-377 (1993).
Creighton, "Proteins: Structures and Molecular Principles," W.H. Freeman & Co., NY, pp. 28-60 (1983).
Cunningham et al., "High-Resolution Epitope Mapping of hGH-Receptor Interactions by Alanine-Scanning Mutagenesis," *Science*, No. 244, pp. 1081-1085 (1989).
Henikoff et al., Proc. Natl. Acad. Sci. USA 89, pp. 10915-10919 (1992).
Karlin et al., "Methods for assessing the statistical significance of molecular sequence features by using general scoring schemes," *Proc. Natl. Acad. Sci. USA*, vol. 87:2264-2268(1990).
Pinckard et al., "Factors Influencing the Immune Response," *Clin Exp. Immunol.* 2, pp. 331-340 (1967).
Posttranslational Covalent Modification of Proteins, B. C. Johnson, Ed., Academic Press, New York, pp. 1-12 (1983).
Phizicky et al., Microbiol. Rev., 59, pp. 94-123 (1995).
Robbins et al., "Antibodies to Covalent Aggregates of Insulin in Blood of Insulin-Using Diabetic Patients," *Diabetes* 36, pp. 838-845 (1987).
Rattan et al., Protein Synthesis, Posttranslational Modifications, and Aging, *Ann. N. Y, Acad Sci.*, 663, pp. 48-62 (1992).
Seifter et al., "Analysis for Protein Modifications and Nonprotein Cofactors," *Meth Enzymol* 182, pp. 626-646 (1990).
International Search Report for related International Patent Application No. PCT/US2010/021241, dated Jul. 15, 2010.
Written Opinion for related International Patent Application No. PCT/US2010/021241, dated Jul. 15, 2010.

(Continued)

*Primary Examiner* — Elly-Gerald Stoica
(74) *Attorney, Agent, or Firm* — Sterne, Kessler, Goldstein & Fox P.L.L.C.

(57) ABSTRACT

Described herein are compositions and methods for treating, preventing and ameliorating diseases and conditions characterized by a lower than normal white blood cell count, such as leukopenia and neutropenia. The compositions and methods include recombinant human albumin-human granulocyte colony stimulating factor. Pharmaceutical formulations including the recombinant fusion protein, and methods of making such formulations are also described.

26 Claims, 39 Drawing Sheets

OTHER PUBLICATIONS

Halpern et al., "Albugranin™, a Recombinant Human Granulocyte Colony Stimulating Factor (G-CSF) Genetically Fused to Recombinant Human Albumin Induces Prolonged Myelopoietic Effects in Mice and Monkeys," *Pharm. Research*, vol. 19, No. 11, pp. 1720-1729 (2002).

Mead, "Novozymes Biopharma-Rethinking Tomorrow," BPE Meeting, Oct. 2008, 19 pgs.

International Search Report for related International Patent Application No. PCT/US2010/021235, dated Jul. 15, 2010.

Holmes, F.A., et al., "Blinded, Randomized, Multicenter Study to Evaluate Single Administration Pegfilgratism Once per Cycle Versus Daily Filgratism as an Adjunct to Chemotherapy in Patients with High-Risk Stage II or Stage III/IV Breast Cancer," *J. Clin. Oncol.* 20:727-731, American Society of Clinical Oncology, United States (2002).

Nabholtz, J.-M., et al., "Docetaxel and Doxorubicin Compared with Doxorubicin and Cyclophosphamide as First-Line Chemotherapy for Metastatic Breast Cancer: Results of a Randomized, Multicenter, Phase III Trial," *J. Clin. Oncol.* 21:968-975, American Society of Clinical Oncology, United States (2003).

Office Action mailed Nov. 2, 2011, in U.S. Appl. No. 12/688,754, Bock et al., filed Jan. 15, 2010.

\* cited by examiner

Effects of Concentrations on rHSA-G-CSF pH Effects (7 Day, 25°)

Effects of NaCl on rHSA-G-CSF (7 Day, 25°)

Effects of Phosphate on rHSA-G-CSF (1 Day, 25°)

Comparison of Protein Concentration Effects in
PMTT20/6.0 and PMTT10/7.2 Formulation Buffers Comparison of Stability in PMTT20/6.0
and PMTT10/7.2 Formulation Buffers

FIGURE 9A

```
   1 GATGCACACAAGAGTGAGGTTGCTCATCGGTTTAAAGATTTGGGAGAAGAAAATTTCAAA  60
   1 D  A  H  K  S  E  V  A  H  R  F  K  D  L  G  E  E  N  F  K    20

61 GCCTTGGTGTTGATTGCCTTTGCTCAGTATCTTCAGCAGTGTCCATTTGAAGATCATGTA 120
  21 A  L  V  L  I  A  F  A  Q  Y  L  Q  Q  C  P  F  E  D  H  V    40

121 AAATTAGTGAATGAAGTAACTGAATTTGCAAAAACATGTGTTGCTGATGAGTCAGCTGAA 180
  41 K  L  V  N  E  V  T  E  F  A  K  T  C  V  A  D  E  S  A  E    60

181 AATTGTGACAAATCACTTCATACCCTTTTTGGAGACAAATTATGCACAGTTGCAACTCTT 240
  61 N  C  D  K  S  L  H  T  L  F  G  D  K  L  C  T  V  A  T  L    80

241 CGTGAAACCTATGGTGAAATGGCTGACTGCTGTGCAAAACAAGAACCTGAGAGAAATGAA 300
  81 R  E  T  Y  G  E  M  A  D  C  C  A  K  Q  E  P  E  R  N  E   100

301 TGCTTCTTGCAACACAAAGATGACAACCCAAACCTCCCCCGATTGGTGAGACCAGAGGTT 360
 101 C  F  L  Q  H  K  D  D  N  P  N  L  P  R  L  V  R  P  E  V   120

361 GATGTGATGTGCACTGCTTTTCATGACAATGAAGAGACATTTTTGAAAAAATACTTATAT 420
 121 D  V  M  C  T  A  F  H  D  N  E  E  T  F  L  K  K  Y  L  Y   140

421 GAAATTGCCAGAAGACATCCTTACTTTTATGCCCCGGAACTCCTTTTCTTTGCTAAAAGG 480
 141 E  I  A  R  R  H  P  Y  F  Y  A  P  E  L  L  F  F  A  K  R   160

481 TATAAAGCTGCTTTTACAGAATGTTGCCAAGCTGCTGATAAAGCTGCCTGCCTGTTGCCA 540
 161 Y  K  A  A  F  T  E  C  C  Q  A  A  D  K  A  A  C  L  L  P   180

541 AAGCTCGATGAACTTCGGGATGAAGGCAAGGCTTCGTCTGCCAAACAGAGACTCAAGTGT 600
 181 K  L  D  E  L  R  D  E  G  K  A  S  S  A  K  Q  R  L  K  C   200

601 GCCAGTCTCCAAAAATTTGGAGAAAGAGCTTTCAAAGCATGGGCAGTAGCTCGCCTGAGC 660
 201 A  S  L  Q  K  F  G  E  R  A  F  K  A  W  A  V  A  R  L  S   220

661 CAGAGATTTCCCAAAGCTGAGTTTGCAGAAGTTTCCAAGTTAGTGACAGATCTTACCAAA 720
 221 Q  R  F  P  K  A  E  F  A  E  V  S  K  L  V  T  D  L  T  K   240

721 GTCCACACGGAATGCTGCCATGGAGATCTGCTTGAATGTGCTGATGACAGGGCGGACCTT 780
 241 V  H  T  E  C  C  H  G  D  L  L  E  C  A  D  D  R  A  D  L   260

781 GCCAAGTATATCTGTGAAAATCAAGATTCGATCTCCAGTAAACTGAAGGAATGCTGTGAA 840
 261 A  K  Y  I  C  E  N  Q  D  S  I  S  S  K  L  K  E  C  C  E   280

841 AAACCTCTGTTGGAAAAATCCCACTGCATTGCCGAAGTGGAAAATGATGAGATGCCTGCT 900
 281 K  P  L  L  E  K  S  H  C  I  A  E  V  E  N  D  E  M  P  A   300

901 GACTTGCCTTCATTAGCTGCTGATTTTGTTGAAAGTAAGGATGTTTGCAAAAACTATGCT 960
 301 D  L  P  S  L  A  A  D  F  V  E  S  K  D  V  C  K  N  Y  A   320

961 GAGGCAAAGGATGTCTTCCTGGGCATGTTTTTGTATGAATATGCAAGAAGGCATCCTGAT 1020
 321 E  A  K  D  V  F  L  G  M  F  L  Y  E  Y  A  R  R  H  P  D   340

1021 TACTCTGTCGTGCTGCTGCTGAGACTTGCCAAGACATATGAAACCACTCTAGAGAAGTGC 1080
 341 Y  S  V  V  L  L  L  R  L  A  K  T  Y  E  T  T  L  E  K  C   360

1081 TGTGCCGCTGCAGATCCTCATGAATGCTATGCCAAAGTGTTCGATGAATTTAAACCTCTT 1140
```

1141 GTGGAAGAGCCTCAGAATTTAATCAAACAAAATTGTGAGCTTTTTGAGCAGCTTGGAGAG 1200
 381 V  E  E  P  Q  N  L  I  K  Q  N  C  E  L  F  E  Q  L  G  E   400

1201 TACAAATTCCAGAATGCGCTATTAGTTCGTTACACCAAGAAAGTACCCCAAGTGTCAACT 1260
 401 Y  K  F  Q  N  A  L  L  V  R  Y  T  K  K  V  P  Q  V  S  T   420

1261 CCAACTCTTGTAGAGGTCTCAAGAAACCTAGGAAAAGTGGGCAGCAAATGTTGTAAACAT 1320
 421 P  T  L  V  E  V  S  R  N  L  G  K  V  G  S  K  C  C  K  H   440

1321 CCTGAAGCAAAAAGAATGCCCTGTGCAGAAGACTATCTATCCGTGGTCCTGAACCAGTTA 1380
 441 P  E  A  K  R  M  P  C  A  E  D  Y  L  S  V  V  L  N  Q  L   460

1381 TGTGTGTTGCATGAGAAAACGCCAGTAAGTGACAGAGTCACCAAATGCTGCACAGAATCC 1440
 461 C  V  L  H  E  K  T  P  V  S  D  R  V  T  K  C  C  T  E  S   480

1441 TTGGTGAACAGGCGACCATGCTTTTCAGCTCTGGAAGTCGATGAAACATACGTTCCCAAA 1500
 481 L  V  N  R  R  P  C  F  S  A  L  E  V  D  E  T  Y  V  P  K   500

1501 GAGTTTAATGCTGAAACATTCACCTTCCATGCAGATATATGCACACTTTCTGAGAAGGAG 1560
 501 E  F  N  A  E  T  F  T  F  H  A  D  I  C  T  L  S  E  K  E   520

1561 AGACAAATCAAGAAACAAACTGCACTTGTTGAGCTCGTGAAACACAAGCCCAAGGCAACA 1620
 521 R  Q  I  K  K  Q  T  A  L  V  E  L  V  K  H  K  P  K  A  T   540

1621 AAAGAGCAACTGAAAGCTGTTATGGATGATTTCGCAGCTTTTGTAGAGAAGTGCTGCAAG 1680
 541 K  E  Q  L  K  A  V  M  D  D  F  A  A  F  V  E  K  C  C  K   560

1681 GCTGACGATAAGGAGACCTGCTTTGCCGAGGAGGGTAAAAAACTTGTTGCTGCAAGTCAA 1740
 561 A  D  D  K  E  T  C  F  A  E  E  G  K  K  L  V  A  A  S  Q   580

1741 GCTGCCTTAGGCTTAACCCCCCTGGGCCCTGCCAGCTCCCTGCCCCAGAGCTTCCTGCTC 1800
 581 A  A  L  G  L  T  P  L  G  P  A  S  S  L  P  Q  S  F  L  L   600

1801 AAGTGCTTAGAGCAAGTGAGGAAGATCCAGGGCGATGGCGCAGCGCTCCAGGAGAAGCTG 1860
 601 K  C  L  E  Q  V  R  K  I  Q  G  D  G  A  A  L  Q  E  K  L   620

1861 TGTGCCACCTACAAGCTGTGCCACCCCGAGGAGCTGGTGCTGCTCGGACACTCTCTGGGC 1920
 621 C  A  T  Y  K  L  C  H  P  E  E  L  V  L  L  G  H  S  L  G   640

1921 ATCCCCTGGGCTCCCCTGAGCAGCTGCCCCAGCCAGGCCCTGCAGCTGGCAGGCTGCTTG 1980
 641 I  P  W  A  P  L  S  S  C  P  S  Q  A  L  Q  L  A  G  C  L   660

1981 AGCCAACTCCATAGCGGCCTTTTCCTCTACCAGGGGCTCCTGCAGGCCCTGGAAGGGATC 2040
 661 S  Q  L  H  S  G  L  F  L  Y  Q  G  L  L  Q  A  L  E  G  I   680

2041 TCCCCCGAGTTGGGTCCCACCTTGGACACACTGCAGCTGGACGTCGCCGACTTTGCCACC 2100
 681 S  P  E  L  G  P  T  L  D  T  L  Q  L  D  V  A  D  F  A  T   700

2101 ACCATCTGGCAGCAGATGGAAGAACTGGGAATGGCCCCTGCCCTGCAGCCCACCCAGGGT 2160
 701 T  I  W  Q  Q  M  E  E  L  G  M  A  P  A  L  Q  P  T  Q  G   720

2161 GCCATGCCGGCCTTCGCCTCTGCTTTCAGCGCCGGGCAGGAGGGGTCCTGGTTGCCTCC 2220
 721 A  M  P  A  F  A  S  A  F  Q  R  R  A  G  G  V  L  V  A  S   740

2221 CATCTGCAGAGCTTCCTGGAGGTGTCGTACCGCGTTCTACGCCACCTTGCCCAGCCC     2280
 741 H  L  Q  S  F  L  E  V  S  Y  R  V  L  R  H  L  A  Q  P      759
```

FIGURE 9C

The amino acid sequence of G-CSF is underlined.
cDNA sequence: A = adenine, C=cytosine, G=guanine, T=thymidine
Amino acid sequence: A = Ala, C = Cys, D = Asp, E = Glu, F = Phe, G = Gly, H = His, I = Ile, K = Lys, L = Leu, M = Met, N = Asn, P = Pro, Q = Gln, R = Arg, S = Ser, T = Thr, V = Val, W = Trp, Y = Tyr

FIGURE 9D

```
  1  MAGPATQSPM KLMALQLLLW HSALWTVQEA TPLGPASSLP QSFLLKCLEQ VRKIQGDGAA
 61  LQEKLCATYK LCHPEELVLL GHSLGIPWAP LSSCPSQALQ LAGCLSQLHS GLFLYQGLLQ
121  ALEGISPELG PTLDTLQLDV ADFATTIWQQ MEELGMAPAL QPTQGAMPAF ASAFQRRAGG
181  VLVASHLQSF LEVSYRVLRH LAQP
```

FIGURE 9E

```
  1  MKWVTFISLL FLFSSAYSRG VFRRDAHKSE VAHRFKDLGE ENFKALVLIA FAQYLQQCPF
 61  EDHVKLVNEV TEFAKTCVAD ESAENCDKSL HTLFGDKLCT VATLRETYGE MADCCAKQEP
121  ERNECFLQHK DDNPNLPRLV RPEVDVMCTA FHDNEETFLK KYLYEIARRH PYFYAPELLF
181  FAKRYKAAFT ECCQAADKAA CLLPKLDELR DEGKASSAKQ RLKCASLQKF GERAFKAWAV
241  ARLSQRFPKA EFAEVSKLVT DLTKVHTECC HGDLLECADD RADLAKYICE NQDSISSKLK
301  ECCEKPLLEK SHCIAEVEND EMPADLPSLA ADFVESKDVC KNYAEAKDVF LGMFLYEYAR
361  RHPDYSVVLL LRLAKTYETT LEKCCAAADP HECYAKVFDE FKPLVEEPQN LIKQNCELFE
421  QLGEYKFQNA LLVRYTKKVP QVSTPTLVEV SRNLGKVGSK CCKHPEAKRM PCAEDYLSVV
481  LNQLCVLHEK TPVSDRVTKC CTESLVNRRP CFSALEVDET YVPKEFNAET FTFHADICTL
541  SEKERQIKKQ TALVELVKHK PKATKEQLKA VMDDFAAFVE KCCKADDKET CFAEEGKKLV
601  AASQAALGL
```

FIGURE 10

| Formulation | Osmolality | SEC% Day at RT | | | |
|---|---|---|---|---|---|
| | mOsm/kg | 0 | 1 | 2 | 3 |
| 10mM PMTT pH5.8 | 297 | 96.75 | 95.55 | 95.46 | 95.43 |
| 10mM CMTT pH6.2 | 299 | 96.55 | 95.47 | 95.42 | 95.01 |
| 10mM PMTT pH6.3 | 299 | 96.52 | 94.01 | 93.99 | 93.87 |
| 10mM PMTT pH6.4 | 294 | 96.58 | 93.57 | 93.51 | 93.24 |
| 10mM PMTT pH7.0 | 299 | 95.96 | 91.12 | 90.65 | 90.33 |

FIGURE 11

| Temperature °C | Time (Day) | SEC (%) | | | |
|---|---|---|---|---|---|
| | | pHs | | | |
| | | 6.0 | 6.8 | 7.2 | 8.0 |
| 4 | 0 | 98.67 | 97.72 | 97.75 | 97.17 |
| | 1 | 98.56 | 98.19 | 97.85 | 96.87 |
| | 7 | 98.31 | 98.44 | 98.26 | 97.72 |
| | 10 | 98.48 | 98.35 | 98.22 | 97.67 |
| 25 | 0 | 98.43 | 97.02 | 96.74 | 97.03 |
| | 1 | 98.5 | 97.58 | 96.87 | 97.11 |
| | 3 | 98.47 | 97.57 | 96.69 | 96.68 |
| | 5 | 98.32 | 97.45 | 96.88 | 95.9 |
| | 7 | 97.65 | 97.28 | 96.62 | 95.64 |
| 40 | 0 | 98.67 | 97.72 | 97.75 | 97.17 |
| | 1 | 93.53 | 90.90 | 84.82 | 69.87 |
| | 7 | 80.47 | 77.09 | 64.80 | 40.2 |
| | 10 | 75.44 | 73.35 | 59.41 | 34.11 |
| 4 | 0 | 98.21 | 97.30 | 97.2 | 97.12 |
| | 1 | 98.52 | 97.51 | 97.26 | 97.07 |
| | 7 | 98.45 | 98.14 | 97.16 | 96.33 |
| | 10 | 98.11 | 97.65 | 97.24 | 96.24 |
| 25 | 0 | 97.96 | 95.62 | 95.92 | 96.52 |
| | 1 | 97.32 | 92.11 | 90.8 | 91.85 |
| | 3 | 97.48 | 91.76 | 90.32 | 90.38 |
| | 5 | 97.13 | 91.84 | 90.07 | 89.45 |
| | 7 | 97.3 | 91.74 | 89.74 | 88.37 |
| 40 | 0 | 98.21 | 97.30 | 97.2 | 97.12 |
| | 1 | 82.67 | 71.98 | 59.16 | 33.29 |
| | 7 | 41.23 | 40.54 | 24.71 | 8.69 |
| | 10 | 31.98 | 33.97 | 20.09 | 6.15 |

FIGURE 12

| Concentration (mg/ml) | Temperature °C | Time (Day) | Bioassay (Relative Potency %) pHs | | | |
|---|---|---|---|---|---|---|
| | | | 6.0 | 6.8 | 7.2 | 8.0 |
| 15 | 4 | 0 | 141 | 141 | 141 | 141 |
| | | 1 | | | | |
| | | 7 | | | | |
| | | 10 | 161 | 102 | 132 | 116 |
| | 25 | 0 | 121 | 121 | 121 | 121 |
| | | 1 | | | | |
| | | 3 | | | | |
| | | 5 | | | | |
| | | 7 | 128 | 112 | 124 | 88 |
| | 40 | 0 | | | | |
| | | 1 | | | | |
| | | 7 | | | | |
| | | 10 | | | | |
| 60 | 4 | 0 | 138 | 138 | 138 | 138 |
| | | 1 | | | | |
| | | 7 | | | | |
| | | 10 | 118 | 96 | 89 | 96 |
| | 25 | 0 | 104 | 104 | 104 | 104 |
| | | 1 | | | | |
| | | 3 | | | | |
| | | 5 | | | | |
| | | 7 | 126 | 116 | 113 | 107 |
| | 40 | 0 | 130 | 130 | 130 | 130 |
| | | 1 | | | | |
| | | 7 | | | | |
| | | 10 | 110 | 92 | 105 | 41 |

FIGURE 13

Fermentation Process

Step 1
1st Stage
Seed Build-Up in Shake Flasks
↓

Step 2
2nd Stage
2x200-L Production Fermentors
↓

Recovery Process

Step 3
Harvest and Clarification of Supernatant by
Microfiltration (MF)/Diafiltration (DF)
↓

Step 4
Ultrafiltration (UF)/Diafiltration (DF) of Supernatant and
0.2 µm Filtration
↓

Purification Process

Step 5
Chromatography Purifications
↓

Step 6
Ultrafiltration (UF)/Diafiltration (DF) (Pre-Formulated Drug Substance)
↓

Step 7
Formulation (Formulated Drug Substance)
↓

Step 8
Aseptic Bulk Fill and Storage (Bulk Drug Substance) (-80°C)

FIGURE 17A

| Test | Analytical Method | Acceptance Criteria | Lot 0710080005 | Lot 071025001 | Lot 071026004 | Lot 071106001 | Lot 071116001 |
|---|---|---|---|---|---|---|---|
| Appearance | Visual inspection | Clear to opalescent, pale yellow to yellow solution | Clear, pale yellow solution | Clear, pale yellow solution | Clear, pale yellow solution | Clear, pale yellow solution | Clear, pale yellow solution |
| pH | pH Electrode | 6.0 ± 0.3 | 6.0 | 6.0 | 6.0 | 6.1 | 6.1 |
| Osmolality | Freezing point | 300 ± 30 mOsm/kg | 305 mOsm/kg | 310 mOsm/kg | 313 mOsm/kg | 313 mOsm/kg | 312 mOsm/kg |
| Protein concentration | Absorbance at 280 nm | Report result (X.X mg/mL) | 64.5 mg/mL | 61.4 mg/mL | 62.0 mg/mL | 64.3 mg/mL | 71.3 mg/mL |
| Purity | SDS-PAGE: Reduced and non-reduced with Coomassie Blue Stain | ≥ 95% | R: 100% NR: 100% | R: 100% NR: 100% | R: 100% NR: 100% | R: 100% NR: 100% | R: 100% NR: 100% |
| Purity | SDS-PAGE: Reduced and non-reduced with Silver stain | Comparable to reference standard | Comparable to reference standard | Comparable to reference standard | Comparable to reference standard | Comparable to reference standard | Comparable to reference standard |
| Purity | SEC-HPLC | ≥ 90.0% | 98.9% | 99.4% | 98.1% | 98.1% | 98.3% |
| Purity | RP-HPLC | Report result (X.X%) | 86.3% | 88.5% | 87.5% | 86.7% | 87.3% |
| Identity | ELISA | Identity confirmed | Identity confirmed | Identity Confirmed | Identity Confirmed | Identity Confirmed | Identity Confirmed |
| Potency | Cell Proliferation | 50-150% | 113% | 79.6% | 87.2% | 102% | 83.4% |

FIGURE 17B

| Bacterial Endotoxin | Kinetic turbidimetric (USP <85>) | ≤ 1.0 EU/mg | <0.003 EU/mg | <0.003 EU/mg | <0.003 EU/mg | <0.003 EU/mg | <0.003 EU/mg |
|---|---|---|---|---|---|---|---|
| Bioburden | Membrane Filtration | ≤10 CFU/10mL | 0 CFU/10mL | 0 CFU/10mL | 0 CFU/10mL | 0 CFU/10mL | 0 CFU/10mL |
| Residual DNA | Threshold | ≤ 100 pg/mg | ND | ND | ND | ND | ND |

FIGURE 17C

| Attribute | Analytical Method | Acceptance Criteria | cGMP Lot 060615001 | cGMP lot 060628001 | cGMP lot 060707001 |
|---|---|---|---|---|---|
| Appearance | Visual inspection | Clear to opalescent, pale yellow to yellow solution | Clear to opalescent, pale yellow to yellow solution | Clear to opalescent, pale yellow to yellow solution | Clear to opalescent, pale yellow to yellow solution |
| pH | pH Electrode | 7.2 ± 0.3 | 7.3 | 7.4 | 7.2 |
| Osmolality | Freezing point | Report result (X mOsm/kg) | 310 mOsm/kg | 311 mOsm/kg | 310 mOsm/kg |
| Protein concentration | Absorbance at 280 nm | Report result (X.X mg/mL) | 26.6 mg/ml | 24.7 mg/ml | 30.1 mg/ml |
| Identity | ELISA | Identity confirmed | Identity confirmed | Identity confirmed | Identity confirmed |
| Purity | SDS-PAGE: Reduced and non-reduced with Coomassie blue stain | ≥ 90% | 100% Reduced 100% Non-Reduced | 100% Reduced 99% Non-Reduced | 100% Reduced 98% Non-Reduced |
| Purity | SDS-PAGE: Reduced and non-reduced with silver stain | Comparable to reference standard | Comparable to reference standard | Comparable to reference standard | Comparable to reference standard |
| Purity | SEC-HPLC | ≥ 90.0% | 97.8% | 99.2% | 98.7% |
| Purity | RP-HPLC | Report result (X.X%) | 85.5% | 85.2% | 84.5% |
| Potency | Bioassay (NFS-60 cell proliferation) | Report result (X%) | 125% | 106% | 109% |
| Residual DNA | Threshold | ≤ 300 pg/mg | <4 pg/mg | <4 pg/mg | <4 pg/mg |

FIGURE 17D

| Attribute | Analytical Method | Acceptance Criteria | cGMP Lot 060615001 | cGMP lot 060628001 | cGMP lot 060707001 |
|---|---|---|---|---|---|
| Bacterial Endotoxin | Kinetic turbidimetric (USP <85>) | ≤ 10 EU/mg | <0.008 EU/mg | <0.008 EU/mg | <0.008 EU/mg |
| Bioburden | Membrane Filtration | ≤10 CFU/10mL | 0 CFU/10 ml | 0 CFU/10ml | 0 CFU/10ml |

| Lane # | Lot | Description | Conditions | µg Load |
|---|---|---|---|---|
| 1 | Mrk1320414 | Size Marker 12 | R | N/A |
| 2 | 2579-092 | Development BDS lot | R | 4 |
| 3 | LDC2378-R | Neugranin Ref. Std. | R | 4 |
| 4 | 02A14078 | Development FDP | R | 4 |
| 5 | 2378FDP | Neugranin FDP | R | 4 |
| 6 | Mrk1320414 | Size Marker 12 | R | N/A |

FIGURE 19
A
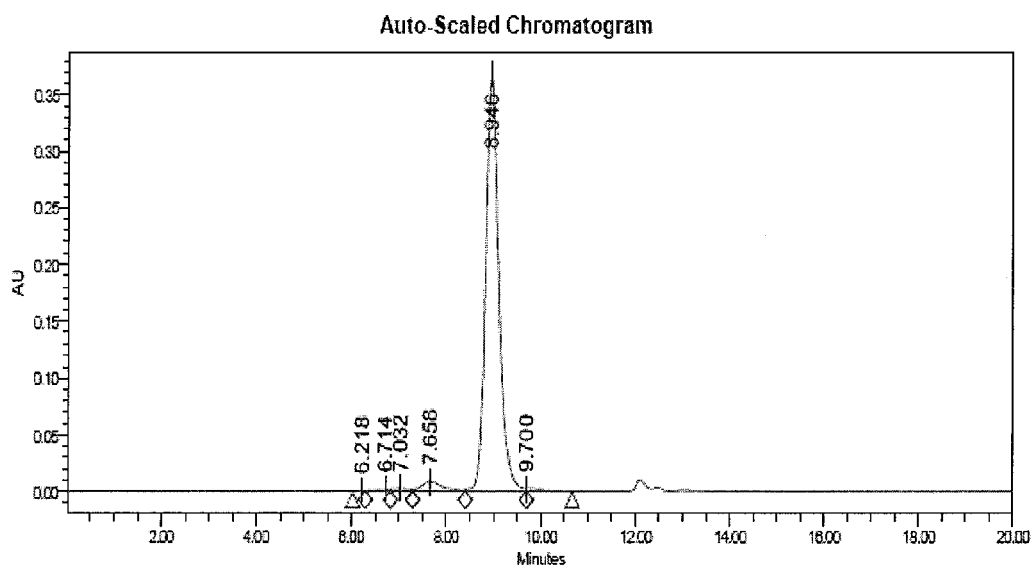
B
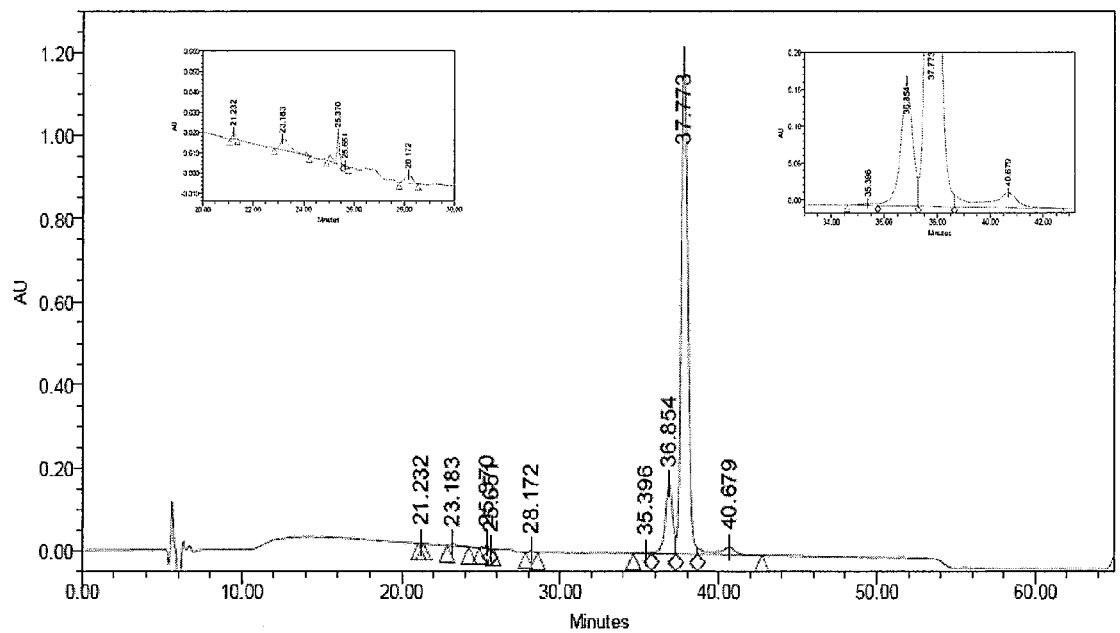

FIGURE 20

| Attribute | Analytical Method | Acceptance Criteria | Lot 3029DP |
|---|---|---|---|
| Appearance | Visual inspection | White to off-white cake | White cake |
| Reconstitution Time (reconstituted with WFI) | Visual inspection | Report result (X sec) | 29 sec. |
| Appearance (post-reconstitution) | Visual inspection | Clear to opalescent, pale yellow to yellow solution, essentially free from foreign particulate matter | Clear, pale yellow, essentially free from foreign particulate matter |
| pH | pH Electrode | 6.0 ± 0.4 | 6.0 |
| Osmolality | Freezing point | 300±50 (X mOsm/kg) | 293 mOsm/kg |
| Purity | SDS-PAGE: Reduced and non-reduced with Coomassie blue stain | ≥ 95% | Reduced: 100% Non-reduced: 100% |
| Purity | SDS-PAGE: Reduced and non-reduced with Silver stain | Comparable to reference standard | Comparable to reference standard |
| Purity | SEC-HPLC | ≥ 90.0% | 98.8% |
| Purity | RP-HPLC | Report result (X.X%) | 86.4% |
| Identity | ELISA | Identity confirmed | ND |
| Potency | Bioassay (NFS-60 cell proliferation) | 50-150% | 95.2% |
| Protein Concentration | Absorbance at 280 nm | 50.0 ± 10.0 mg/mL | 47.7 mg/mL |
| Sterility | USP <71> | No growth | ND |
| Bacterial Endotoxin | Kinetic turbidimetric (USP <85>) | ≤ 1 EU/mg | ND |
| Subvisible Particulate Matter | USP <788> Light Obscuration | Meets USP <788> | ND |
| Residual Moisture | Karl-Fischer Coulometer | ≤3.0% | 0.2% |

FIGURE 22

| Time (hr) | SEC% | | RP% | | IEC% | | Relative Potency (%) | |
|---|---|---|---|---|---|---|---|---|
| | $H_2O_2$ | TPB | $H_2O_2$ | TPB | $H_2O_2$ | TPB | $H_2O_2$ | TPB |
| 0 | 96.06 | 96.06 | 83.86 | 83.86 | 87.53 | 87.53 | 103 | 108 |
| 1 | 96.01 | 96.17 | 44.49 | 70.2 | 21.04 | 82.98 | | |
| 3 | 96.22 | 97.14 | 41.19 | 55.72 | 18.78 | 82.69 | 90.2 | 113 |
| 5 | 96.31 | 97.18 | 37.08 | 47.52 | 14.85 | 81.89 | | |
| 8 | 96.05 | 97.09 | 31.86 | 40.23 | 11.8 | 80.87 | 91.8 | 127 |
| 20 | 95.17 | 97.23 | 17.29 | 32.36 | 13.68 | 79.5 | | |
| 24 | 95.01 | 97.2 | 14.54 | 31.91 | 12.89 | 77.2 | 72.8 | 112 |

Pharmacokinetics of Neugranin in Phase 1 Human Subjects (Cycle 0)

The serum concentration of NEUG administered subcutaneously at the indicated doses was measured in subjects with breast cancer in the absence of chemotherapy.

ANC for Subjects in part B, Phase I

PK/PD of Neugranin in cycle 1 of chemotherapy
Phase I, Part B (450μg/kg Neugranin)

STABLE FORMULATIONS OF HIGHLY CONCENTRATED RECOMBINANT HUMAN ALBUMIN-HUMAN GRANULOCYTE COLONY STIMULATING FACTOR

CROSS-REFERENCE TO RELATED APPLICATION(S)

The present application claims the benefit of U.S. Provisional Application No. 61/145,440 filed on Jan. 16, 2009, and U.S. Provisional Application No. 61/145,436 filed on Jan. 16, 2009. The contents of U.S. Provisional Application No. 61/145,440 and U.S. Provisional Application No. 61/145,436 are hereby incorporated by reference in their entirety.

SEQUENCE LISTING

The instant application contains a Sequence Listing which has been submitted via EFS-Web and is hereby incorporated by reference in its entirety. Said ASCII copy, created on Mar. 4, 2010, is named 75977237.txt, and is 25,492 bytes in size.

BACKGROUND

Leukopenia is a reduction in the circulating White Blood Cells (WBC) and is often defined as WBC count to <4000/mL. The main cells involved in leukopenia are neutrophils. However a reduced number of lymphocytes, monocytes, eosinophils, or basophils may also contribute to the decreased total cell count (Merck Manual, 17th edition).

Neutropenia is characterized by a reduction in the blood neutrophil count, often leading to increased susceptibility to bacterial and fungal infections. Neutropenia is classified by the neutrophil count and the relative risk of infection: mild (1000 to 1500/mL), moderate (grade 3,500 to 1000/mL), or severe (grade 4, <500/mL). Acute and severe neutropenia is a life-threatening condition as it predisposes the patient to rapidly fatal infections (Merck Manual, 17th edition).

Neutropenia can be caused by impaired production of neutrophils in the bone marrow, or by accelerated destruction of neutrophils. Acute neutropenia may occur over a few days when neutrophil use is rapid and production is severely impaired. Chronic neutropenia may last for many months and is often caused by reduced production or sequestration of neutrophils in the spleen. Neutropenia may be classified by whether it arises secondary to factors extrinsic to marrow myeloid cells or whether an intrinsic defect appears to be present in the myeloid progenitors (Merck Manual, 17th edition).

Neutropenia and its infectious complications are among the most common and serious adverse effects of cytotoxic chemotherapy and other cancer therapies such as radiation therapy, biotherapy, and bone marrow transplantation. Cytotoxic chemotherapy, which works by seeking out and destroying fast-growing cells, induces neutropenia because of the high proliferative rate of neutrophil precursors and the rapid turnover of blood neutrophils (Merck Manual, 17th edition). The most common symptoms of neutropenia in patients with undergoing chemotherapy include fever, mouth sores, and ear infections. Patients with profound neutropenia often suffer from pyogenic infections such as septicemia, cutaneous cellulitis, liver abscesses, furunculosis, pneumonia, stomatitis, gingivitis, perirectal inflammation, colitis, sinusitis, and otitis media. Chemotherapy may have to be delayed until the body can produce more neutrophils and a lower dosage may have to be given, resulting in the treatment being less effective.

SUMMARY

The present invention is directed to compositions and methods useful in treating, preventing or ameliorating diseases and conditions characterized by a lower than normal white blood cell count, such as leukopenia and neutropenia. In some embodiments, the compositions and methods include the recombinant human albumin-human granulocyte colony stimulating factor shown in FIG. 9, or a variant or fragment thereof. In some embodiments, the compositions and methods are used to treat, prevent or ameliorate neutropenia and/or leukopenia, for example, neutropenia caused by the administration of drugs, such as chemotherapy drugs administered for the treatment of cancer, can be treated using the compositions of the invention.

In some embodiments, the compositions are pharmaceutical formulations and include the recombinant human albumin-human granulocyte colony stimulating factor shown in FIG. 9, or a fragment or variant thereof. In some embodiments, the pharmaceutical formulation includes at least one pharmaceutically acceptable carrier, and has a pH of between about 5 and about 8.0, between about 5 and about 7.5, between about 5 and about 7.2, between about 5 and about 7.0, between about 5 and about 6.8, between about 5 and about 6.6, between about 5 and about 6.4, between about 5 and about 6.2, between about 5 and about 6, between about 6 and about 7.5, between about 6.0 and about 7.2, between about 6 and about 7. In other embodiments, the pH is about 4, about 4.2, about 4.4, about 4.5, about 4.6, about 4.8 about 5, about 5.2 about 5.4 about 5.5, about 5.6, about 5.8, about 6.0, about 6.2, about 6.4, about 6.5 about 6.6, about 6.8, about 7.0, about 7.2, about 7.4 about 7.5, about 7.6, about 7.8 or about 8.0.

In some embodiments, the pharmaceutical composition includes recombinant human albumin-human granulocyte colony stimulating factor at a concentration of between about 2.5 and about 240 mg/ml, between about 30 and about 120 mg/ml, between about 60 and about 120 mg/ml, about 5 mg/ml, about 10 mg/ml, about 15 mg/ml, about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 70 mg/ml, about 80 mg/ml, about 90 mg/ml, about 100 mg/ml, about 120 mg/ml, about 150 mg/ml, about 100 mg/ml, about 150 mg/ml, about 200 mg/ml, about 240 mg/ml, or about 250 mg/ml.

In some embodiments, the pharmaceutical composition includes at least one pharmaceutically acceptable salt. In some embodiments, the salt is present in the composition at a concentration of between about 5 and about 50 mM, between about 10 and about 40 mM, between about 15 and about 30 mM, between about 20 and about 25 mM. In some embodiments, the salt is present in the composition at a concentration of about 5 mM, about 10 mM, about 15 mM, about 20 mM, about 25 mM, about 30 mM, about 35 mM, about 40 mM about 45 mM and about 50 mM.

In some embodiments, the pharmaceutical composition of includes at least one pharmaceutically acceptable buffer. In some embodiments, the buffer is present in the composition at a concentration of between about 5 and about 50 mM, between about 10 and about 50 mM, between about 15 and about 50 mM, between about 5 and about 10 mM, between about 10 and about 20 mM, between about 20 and about 30 mM, between about 15 and about 25 mM, or at about 20 mM. In some embodiments, the buffer is present in the composition at a concentration of about 5 mM, about 10 mM, about 15 mM, about 20 mM, about 25 mM, about 30 mM, about 35 mM, about 40 mM, about 45 mM, about 50 mM, about 55 mM or about 60 mM. In some embodiments, the buffer is a phosphate, a citrate, or a combination thereof. In some embodiments, the buffer includes sodium phosphate, sodium phosphate monobasic, sodium phosphate dibasic or a combination thereof.

In some embodiment, the pharmaceutical composition includes a freeze-drying stabilizer. In some embodiments the freeze-drying stabilizer is trehalose dihydrate. In some embodiments, the concentration of trehalose dihydrate is between about 20 to about 100 mM, between about 40 to about 80 mM, between about 50 to about 70 mM, or about 60 mM. In some embodiments, the concentration of the stabilizer is about 20 mM, about 30 mM, about 40 mM, about 50 mM, about 60 mM, about 70 mM, about 80 mM, about 90 mM, about 100 mM, about 110 mM or about 120 mM.

In some embodiments, the pharmaceutical composition includes a bulking agent. In some embodiments, the bulking agent is a poly-alcohol. In some embodiments, the poly-alcohol is mannitol. In further embodiments, the pharmaceutical composition includes a pharmaceutically acceptable carrier. In some embodiment, the carrier is polysorbate.

The pharmaceutical compositions described herein may be formulated for administration in a number of forms. For example, in some embodiments, the pharmaceutical compositions are prepared for oral, pulmonary, intravenous, intramuscular, subcutaneous, rectal, ophthalmic, colonic, parenteral, intracisternal, intravaginal, intraperitoneal, ocular, otic, local, buccal, nasal, or topical administration. Compositions may also be formulated for specific dosage forms. For example, in some embodiments, the pharmaceutical composition may be formulated as a liquid, gel, aerosol, ointment, cream, lyophilized formulation, powder, cake, tablet, or capsule. In other embodiments, the pharmaceutical composition is formulated as a controlled release formulation, fast melt formulation, delayed release formulation, extended release formulation, pulsatile release formulation, and mixed immediate release formulation. In some embodiments, the pharmaceutical composition is provided as a liquid. In other embodiments, the pharmaceutical composition is provided as a lyophilized powder. In still other embodiments, the pharmaceutical composition is provided as a lyophilized cake.

The pharmaceutical composition described herein may be stored in a variety of ways. In some embodiments, the pharmaceutical composition is stored in a vial; in other embodiments, the pharmaceutical composition is stored in a syringe.

In some embodiments, the pharmaceutical composition comprises recombinant human albumin-human granulocyte colony stimulating factor, at least one a buffer and/or pH adjusting agent, and optionally at least one additional pharmaceutically acceptable carrier, wherein the monomeric purity in solution of recombinant human albumin-human granulocyte colony stimulating factor decreases by less than 10% after incubation at 25° C. for 24 hours. In some embodiments, the buffer is the same as the pH adjusting agent. In some embodiments, the monomeric purity in solution after incubation at 25° C. for 24 hours decreases by less than about 1%, less than about 5%, less than about 15%, less than about 20% or less than about 25%.

In other embodiments, the pharmaceutical composition comprises recombinant human albumin-human granulocyte colony stimulating factor, about 20 mM sodium phosphate, about 180 mM mannitol, about 60 mM trehalose dihydrate, about 0.01% (w/v) polysorbate 80, and pH of about 6.0, wherein the concentration of the recombinant human albumin-human granulocyte colony stimulating factor is between about 2.5 mg/ml to about 120 mg/ml, or between about 30 mg/ml to about 60 mg/ml. In some embodiments, the concentration of the recombinant human albumin-human granulocyte colony stimulating factor is about 5, mg/ml, about 10 mg/ml, about 15 mg/ml, about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 70 mg/ml, about 80 mg/ml, about 90 mg/ml, about 100 mg/ml, about 120 mg/ml, about 150 mg/ml, about 100 mg/ml, about 150 mg/ml, about 200 mg/ml, about 240 mg/ml, or about 250 mg/ml.

In still other embodiments, the pharmaceutical composition includes recombinant human albumin-human granulocyte colony stimulating factor and PMTT20/6.0, wherein the concentration of the recombinant human albumin-human granulocyte colony stimulating factor is between about 2.5 and about 120 mg/ml, or between about 30 mg/ml to about 60 mg/ml. In some embodiments, the concentration of the recombinant human albumin-human granulocyte colony stimulating factor is about 5, mg/ml, about 10 mg/ml, about 15 mg/ml, about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 70 mg/ml, about 80 mg/ml, about 90 mg/ml, about 100 mg/ml, about 120 mg/ml, about 150 mg/ml, about 100 mg/ml, about 150 mg/ml, about 200 mg/ml, about 240 mg/ml, or about 250 mg/ml.

Both the foregoing general description and the following brief description of the drawings and the detailed description are exemplary and explanatory and are intended to provide further explanation of the invention as claimed. Other objects, advantages, and novel features will be readily apparent to those skilled in the art from the following detailed description of the invention.

BRIEF DESCRIPTION OF THE DRAWINGS

FIG. 9A-E. FIG. 9A-C shows the nucleic acid (SEQ ID NO: 3) and amino acid sequence (SEQ ID NO: 4) of the rHSA-G-CSF fusion polypeptide termed Neugranin™ ("NEUG"); FIG. 9D shows the amino acid sequence (SEQ ID NO: 5) of human G-CSF; FIG. 9E shows the amino acid sequence (SEQ ID NO: 6) of human serum albumin.

FIG. 10 is a table showing aggregation measured by SE-HPLC of rHSA-G-CSF incubated at different pHs, at a concentration of 48 mg/ml and at 25° C. for up to 3 days.

FIG. 11 is a table showing aggregation of rHSA-G-CSF at different pH, protein concentration and temperature measured by SE-HPLC. The top half of the table (first 3 entries) are at 15 mg/ml rHSA-G-CSF. The bottom half of the table (last three entries) are at 60 mg/ml rHSA-G-CSF.

FIG. 12 is a table showing the activity of rHSA-G-CSF after incubation at different pHs, temperature and concentrations.

FIG. 13 is a flow chart showing an exemplary overview of manufacture of NEUG.

FIGS. 17A-D provide tables summarizing test results of three different lots of NEUG-1 and five different lots of NEUG-2, prepared for clinical use in humans.

FIGS. 19A and 19B show chromatograms of SE-HPLC and RP-HPLC of Lot 2378-R NEUG-1 reference standard.

FIG. 20 summarizes the results of analysis performed on a representative, development lot of NEUG-2 final drug product.

FIG. 22 is a table showing the results of NEUG treated with hydrogen peroxide and TBO or TPB. Studies were performed to monitor the oxidation of NEUG.

FIG. 30A is a graph; the data from FIG. 30A is summarized in the table, 30B.

DETAILED DESCRIPTION

Figure 1:
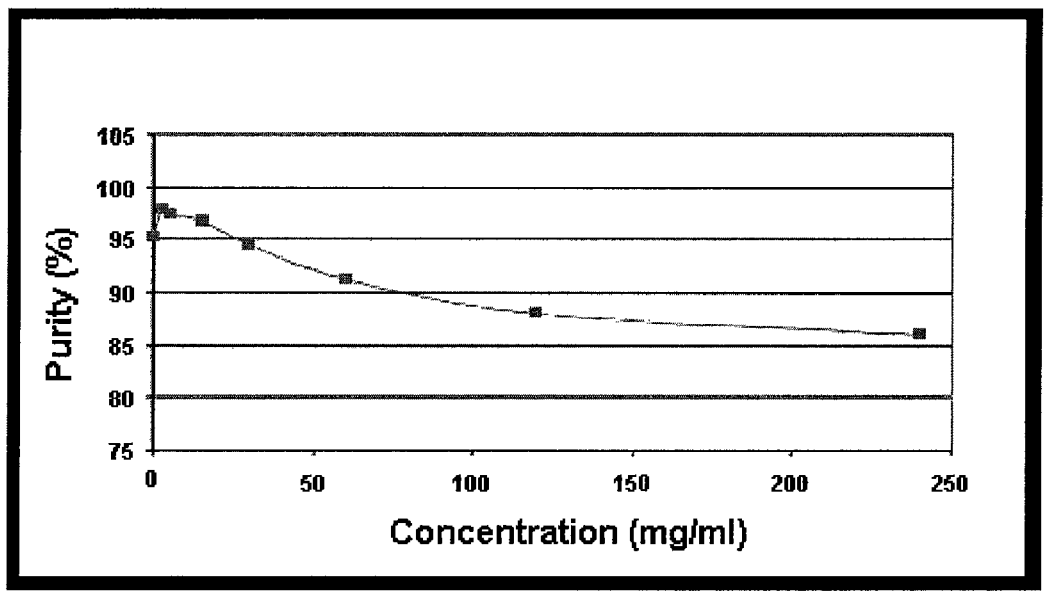
FIG. 1 is a graph showing that increasing rHSA-G-CSF concentration reduces monomer purity. Monomer purity of rHSA-G-CSF samples at concentrations ranging from 2.5 to 240 mg/ml was measured by size exclusion high performance liquid chromatography ("SE-HPLC") after incubation in PMTT10/7.2 at 25° C. for 24 hours.

Disclosed herein are compositions and methods for treating, preventing and ameliorating conditions and diseases characterized by a lowered white blood cell count. The compositions and method described herein include a fusion polypeptide formed from human serum albumin protein ("HSA") and human granulocyte-colony stimulating factor ("G-CSF"). In one embodiment of the invention, the fusion polypeptide is 759 amino acids in length; amino acids 1-585 of the fusion correspond to amino acids from the mature form of HSA, and amino acids 586-759 of the fusion correspond to amino acids of the mature form of human G-CSF. The amino acid sequences of the fusion protein is presented in FIG. 9A-9C.

Compositions and methods described herein also include therapeutic formulations and pharmaceutical compositions comprising the recombinant HSA-G-CSF polypeptide. In some embodiments, these formulations and compositions are configured for administration of lower doses of the polypeptide, while in other embodiments, the formulations are configured for administration of higher doses of the polypeptide.

The invention also encompasses fusion proteins comprising variants or fragments of G-CSF, and fusion proteins comprising albumin or fragments or variants of albumin. The invention also encompasses polynucleotides encoding the therapeutic albumin fusion proteins of the invention, therapeutic albumin fusion proteins, compositions, pharmaceutical compositions, formulations and kits. Host cells transformed with the polynucleotides encoding therapeutic albumin fusion proteins are also encompassed by the invention, as are methods of making the albumin fusion proteins of the invention using these polynucleotides, and/or host cells.

In one embodiment, an albumin fusion protein according to the present invention has extended shelf fife.

In a second embodiment, an albumin fusion protein according to the present invention is more stable than the corresponding unfused G-CSF molecule.

The present invention further includes transgenic organisms modified to contain the nucleic acid molecules of the invention, preferably modified to express an albumin fusion protein of the invention.

The present invention relates generally to polynucleotides encoding albumin fusion proteins; albumin fusion proteins; and methods of treating, preventing, or ameliorating diseases or disorders using albumin fusion proteins or polynucleotides encoding albumin fusion proteins. As used herein, "albumin fusion protein" refers to a protein formed by the fusion of at least one molecule of albumin (or a fragment or variant thereof) to at least one molecule of G-CSF (or fragment or variant thereof). An albumin fusion protein of the invention comprises at least a fragment or variant of a G-CSF and at least a fragment or variant of human serum albumin, which are associated with one another by genetic fusion (i.e., the albumin fusion protein is generated by translation of a nucleic acid in which a polynucleotide encoding all or a portion of G-CSF is joined in-frame with a polynucleotide encoding all or a portion of albumin). The G-CSF and albumin protein, once part of the albumin fusion protein, may each be referred to as a "portion," "region" or "moiety" of the albumin fusion protein (e.g., a "G-CSF protein portion" or an "albumin protein portion"). In a highly preferred embodiment, an albumin fusion protein of the invention comprises at least one molecule of G-CSF or fragment or variant of thereof (including, but not limited to a mature form of the G-CSF protein) and at least one molecule of albumin or fragment or variant thereof (including but not limited to a mature form of albumin).

In a further preferred embodiment, an albumin fusion protein of the invention is processed by a host cell and secreted into the surrounding culture medium. Processing of the nascent albumin fusion protein that occurs in the secretory pathways of the host used for expression may include, but is not limited to signal peptide cleavage; formation of disulfide bonds; proper folding; addition and processing of carbohydrates (such as for example, N- and O-linked glycosylation); specific proteolytic cleavages; and assembly into multimeric proteins. An albumin fusion protein of the invention is preferably in the processed form. In a most preferred embodiment, the "processed form of an albumin fusion protein" refers to an albumin fusion protein product which has undergone N-terminal signal peptide cleavage, herein also referred to as a "mature albumin fusion protein."

In one embodiment, the invention provides a polynucleotide encoding an albumin fusion protein comprising, or alternatively consisting of, G-CSF and a serum albumin protein. In a further embodiment, the invention provides an albumin fusion protein comprising, or alternatively consisting of, G-CSF protein and a serum albumin protein. In other embodiments, the invention provides an albumin fusion protein comprising, or alternatively consisting of, a biologically active and/or therapeutically active fragment of G-CSF protein and a serum albumin protein. In other embodiments, the invention provides an albumin fusion protein comprising, or alternatively consisting of, a biologically active and/or therapeutically active variant of G-CSF protein and a serum albumin protein. In preferred embodiments, the serum albumin protein component of the albumin fusion protein is the mature portion of serum albumin. The invention further encompasses polynucleotides encoding these albumin fusion proteins.

In further embodiments, the invention provides an albumin fusion protein comprising, or alternatively consisting of, G-CSF protein, and a biologically active and/or therapeutically active fragment of serum albumin. In further embodiments, the invention provides an albumin fusion protein comprising, or alternatively consisting of, G-CSF protein and a biologically active and/or therapeutically active variant of serum albumin. In preferred embodiments, the G-CSF protein portion of the albumin fusion protein is the mature portion of the G-CSF protein. In a further preferred embodiment, the G-CSF protein portion of the albumin fusion protein is the extracellular soluble domain of the G-CSF protein. In an alternative embodiment, the G-CSF protein portion of the albumin fusion protein is the active form of the G-CSF protein. The invention further encompasses polynucleotides encoding these albumin fusion proteins.

In further embodiments, the invention provides an albumin fusion protein comprising, or alternatively consisting of, a biologically active and/or therapeutically active fragment or variant of G-CSF protein and a biologically active and/or therapeutically active fragment or variant of serum albumin. In preferred embodiments, the invention provides an albumin fusion protein comprising, or alternatively consisting of, the mature portion of G-CSF protein and the mature portion of serum albumin. The invention further encompasses polynucleotides encoding these albumin fusion proteins.

I. DEFINITIONS

The present invention is described herein using several definitions, as set forth below and throughout the specification.

As used herein, "polynucleotide" refers to a nucleic acid molecule having a nucleotide sequence encoding a fusion protein comprising, or alternatively consisting of, at least one molecule of albumin (or a fragment or variant thereof) joined in frame to at least one molecule of Granulocyte-colony stimulating factor (G-CSF) (or fragment or variant thereof).

As used herein, "albumin fusion construct" refers to a nucleic acid molecule comprising, or alternatively consisting of, a polynucleotide encoding at least one molecule of albumin (or a fragment or variant thereof) joined in frame to at least one polynucleotide encoding at least one molecule of G-CSF (or fragment or variant thereof); and, further comprising, for example, one or more of the following elements: (1) a functional self-replicating vector (including but not limited to, a shuttle vector, an expression vector, an integration vector, and/or a replication system), (2) a region for initiation of transcription (e.g., a promoter region, such as for example, a regulatable or inducible promoter, a constitutive promoter), (3) a region for termination of transcription, (4) a leader sequence, and (5) a selectable marker. The polynucleotide encoding the G-CSF and albumin protein, once part of the albumin fusion construct, may each be referred to as a "portion," "region" or "moiety" of the albumin fusion construct.

By a G-CSF polypeptide displaying a "therapeutic activity" or a G-CSF protein that is "therapeutically active" is meant a G-CSF polypeptide that possesses one or more known biological and/or therapeutic activities associated with G-CSF protein. As a non-limiting example, a "G-CSF therapeutic protein" is a G-CSF protein that is useful to treat, prevent or ameliorate a disease, condition or disorder. As a non-limiting example, a "G-CSF therapeutic protein" may be one that binds specifically to a particular cell type (normal (e.g., lymphocytes) or abnormal e.g., (cancer cells)) and therefore may be used to target a compound (drug, or cytotoxic agent) to that cell type specifically.

As used herein, the term "subject" is refers to an animal, preferably a mammal, more preferably a human. The term "subject" and "patient" may be used interchangeably.

The term "pharmaceutically acceptable carrier" refers to any carrier that has substantially no long term or permanent detrimental effect when administered to an individual. Pharmaceutically acceptable carriers include diluents, fillers, salts, dispersion media, coatings, emulsifying agents, wetting agents, sweetening or flavoring agents, tonicity adjusters, absorption delaying agents, preservatives, antibacterial and antifungal agents, buffers, pH adjusting agent, anti-oxidants, stabilizers, solubilizers, bulking agents, cryoprotectant agents, aggregation inhibiting agents, or formulation auxiliary of any type. Suitable carriers are described in Remington's Pharmaceutical Sciences (Remington's Pharmaceutical Sciences, 2000, 20th Ed., Lippincott, Williams & Wilkins), incorporated herein by reference. Preferred examples of such carriers or diluents include, but are not limited to, water, sodium chloride, mannitol, trehalose dehydrate, polysorbate, such as polysorbate 80, various pharmaceutically acceptable buffers for adjusting pH (e.g. phosphate buffers, citrate buffers, acetate buffers, and borate buffers).

The term "pharmaceutically acceptable salts" include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The term "freeze-drying stabilizer" refers to a molecule that protects and reduces chemical and/or physical instability of freeze-dried material. Preferred examples of freeze-drying stabilizers include, but are not limited to, sucrose, trehalose, monosodium glutamate, histidine, betaine, magnesium sulfate, glycerin, erythritol, glycerol, arabitol, xylitol, sorbitol, mannitolpropylene glycol, polyethylene glycol, pluronics, and combinations thereof. The preferred freeze-drying stabilizer is a non-reducing sugar, such as trehalose dihydrate or sucrose.

The term "bulking agent" refers to a compound which adds mass to the lyophilized mixture and contributes to the physical structure of the lyophilized cake. Exemplary bulking agents include sorbitol, glycine, mannitol, and polyethylene glycol.

The term "PMTT20/6.0" refers to a composition comprising sodium phosphate monobasic (2.42 mg/mL, 17.4 mM), sodium phosphate dibasic (0.35 mg/mL, 2.5 mM), mannitol (32.79 mg/mL, 180 mM), trehalose dehydrate (22.70 mg/mL, 60 mM), polysorbate 80 (0.1 mg/mL, 0.01%), the composition at a final pH of 6.0. This is also referred to a "new buffer," "new PMTT" or "new formulation buffer," and is also described as comprising 20 mM phosphate, 180 mM mannitol, 60 mM trehalose dehydrate, 0.01% (w/v) polysorbate 80, pH 6.0

The term "PMTT10/7.2" refers to a composition comprising 10 mM phosphate, 190 mM mannitol, 60 mM trehalose dihydrate, 0.01% (W/V) polysorbate 80, the composition at a final pH of 7.2. This is also referred to as "old buffer," "old PMTT" or "old formulation buffer."

The term "PMTT" refers to a composition comprising phosphate, mannitol, trehalose dehydrate and polysorbate.

The term "CMTT10" refers to a composition comprising 10 mM sodium citrate, 190 mM mannitol, 60 mM trehalose dehydrate, 0.01% (WA') polysporbate 80, buffer at pH of 6.2.

II. GRANULOCYTE-COLONY STIMULATING FACTOR

Granulocyte-colony stimulating factor (G-CSF) is a hematopoietic growth factor that stimulates the production of neutrophils. Administration of G-CSF results in rapid induction of a neutrophilic leukocytosis. Another important in vivo activity of G-CSF is mobilization of hematopoietic progenitor cells into the peripheral blood (Duhrsen et al, 1988; Molineux et al, 1999; Roberts et al, 1994). This effect includes not only the neutrophil lineage but extends to other single lineage and multi-lineage progenitors and pluripotent hematopoietic stem cells (Molineux et al, 1999). G-CSF also increases the cellular events that are part of the defense mechanism against infections by priming neutrophils, thereby increasing both their phagocytic and anti-bacterial activities against opsonized *Staphylococcus aureus*. G-CSF also induces chemotaxis of neutrophils and monocytes and adhesion of neutrophils (Yuo et al, 1989; Wang et al, 1988).

Recombinant G-CSF products are currently approved for a number of clinical indications to stimulate the proliferation and differentiation of neutrophils. In clinical trials, filgrastim (recombinant methionyl human G-CSF; Neupogen®, Amgen, Thousand Oaks, Calif.) increased the number of peripheral neutrophils and thereby reduced the duration of neutropenia after myelosuppressive chemotherapy. Filgrastim is given by daily subcutaneous (SC) injection. Pegfilgrastim, a polyethylene glycol-conjugated rG-CSF, (Neulasta®), has proven safe and effective as a once-per-cycle alternative to daily rG-CSF therapy to decrease the incidence of febrile neutropenia in patients receiving myelosuppressive anti-cancer drugs (Holmes, O'Shaughnessy et al, 2002; Green et al, 2003; Neulasta® SmPC 2007).

III. HUMAN SERUM ALBUMIN

Human serum albumin (HSA) is the most prevalent naturally occurring blood protein in the human circulatory system, measured at approximately 40 grams of albumin/liter, persisting in the circulation for over 20 days. HSA lacks enzymatic or immunological function and is widely distributed in vivo and is known to be a carrier for therapeutic substances in the blood. Albumin is a carrier protein with minimal activity at physiological concentrations. Both HSA and recombinant human albumin (rHSA) have the same long circulating half-life in humans. Research has shown that therapeutic proteins genetically fused to human albumin are able to take on the circulating half-life characteristics of albumin (Syed et al, 1997). For example, a study in rabbits has shown that the half-life of CD4 fused to albumin is 140 fold greater than non-fused CD4 (Yeh et al, 1992).

Human serum albumin, a protein of 585 amino acids in its mature form (as shown in FIG. 1 of U.S. Pat. No. 7,592,010, is responsible for a significant proportion of the osmotic pressure of serum and also functions as a carrier of endogenous and exogenous ligands. At present, HSA for clinical use is produced by extraction from human blood. The production of recombinant HSA (rHSA) in microorganisms has been disclosed in EP 330 451 and EP 361 991.

IV. TREATMENT WITH G-CSF

Primary prophylaxis with granulocyte colony-stimulating factors (G-CSF) is recommended for the prevention of febrile neutropenia in patients who are at high risk based on age, medical history, disease characteristics, and myelotoxicity of the chemotherapy regimen. The American Society of Clinical Oncology (ASCO) and the European Organization for Research and Treatment of Cancer (EORTC) recommends the use of G-CSF when the risk of febrile neutropenia is approximately 20%. The U.S. National Comprehensive Cancer Center Network (NCCN) recommends an optional indication of G-CSF prophylaxis when the risk of febrile neutropenia is 10% to 20% and a definite indication of G-CSF prophylaxis when the risk of febrile neutropenia is at least 20% (Smith et al, 2006, Vogel et al 2005, Timmer-Bonte et al 2006, NCCN Guidelines).

Prophylaxis with colony-stimulating factors (CSFs) is recommended to alleviate the toxicity of certain chemotherapy regimens. However, the added cost of these treatments is a significant consideration both in the U.S. and especially in parts of the EU and may lead to under-use of prophylactic G-CSF treatment and may also limit patient eligibility for dose-intensive chemotherapy regimens (Timmer-Bonte et al, 2006; Adams et al, 2006, NCCN Guidelines).

V. POLYPEPTIDE AND POLYNUCLEOTIDE FRAGMENTS AND VARIANTS

A. Fragments

The present invention is further directed to fragments of G-CSF protein, albumin proteins, and/or albumin fusion proteins of the invention. The present invention is also directed to polynucleotides encoding fragments of the G-CSF protein, albumin proteins, and/or albumin fusion proteins of the invention. Even if deletion of one or more amino acids from the N-terminus of a protein results in modification or loss of one or more biological functions of the G-CSF protein, albumin protein, and/or albumin fusion protein of the invention, other therapeutic activities and/or functional activities (e.g., biological activities, ability to multimerize, ability to bind a ligand) may still be retained. For example, the ability of polypeptides with N-terminal deletions to induce and/or bind to antibodies which recognize the complete or mature forms of the polypeptides generally will be retained when less than the majority of the residues of the complete polypeptide are removed from the N-terminus. Whether a particular polypeptide lacking N-terminal residues of a complete polypeptide retains such immunologic activities can readily be determined by routine methods described herein and otherwise known in the art. It is not unlikely that a mutein with a large number of deleted N-terminal amino acid residues may retain some biological or immunogenic activities. In fact, peptides composed of as few as six amino acid residues may often evoke an immune response.

Accordingly, fragments of G-CSF protein corresponding to a G-CSF protein portion of an albumin fusion protein of the invention include the full length protein as well as polypeptides having one or more residues deleted from the amino terminus of the amino acid sequence of the reference polypeptide (i.e., a G-CSF protein, or a G-CSF protein portion of an albumin fusion protein encoded by a polynucleotide or albumin fusion construct). In particular, N-terminal deletions may be described by the general formula m to q, where q is a whole integer representing the total number of amino acid residues in a reference polypeptide (e.g., a G-CSF protein, or a G-CSF protein portion of an albumin fusion protein of the invention), and m is defined as any integer ranging from 2 to q minus 6. Polynucleotides encoding these polypeptides are also encompassed by the invention.

In addition, fragments of serum albumin polypeptides corresponding to an albumin protein portion of an albumin fusion protein of the invention, include the full length protein as well as polypeptides having one or more residues deleted from the amino terminus of the amino acid sequence of the reference polypeptide (i.e., serum albumin, or a serum albumin portion of an albumin fusion protein). In preferred embodiments, N-terminal deletions may be described by the general formula m to 585, where 585 is a whole integer representing the total number of amino acid residues in mature human serum albumin, and m is defined as any integer ranging from 2 to 579. Polynucleotides encoding these polypeptides are also encompassed by the invention. In additional embodiments, N-terminal deletions may be described by the general formula m to 609, where 609 is a whole integer representing the total number of amino acid residues in full length human serum albumin, and m is defined as any integer ranging from 2 to 603. Polynucleotides encoding these polypeptides are also encompassed by the invention.

Moreover, fragments of albumin fusion proteins of the invention, include the full length albumin fusion protein as well as polypeptides having one or more residues deleted from the amino terminus of the albumin fusion protein. In particular, N-terminal deletions may be described by the general formula m to q, where q is a whole integer representing the total number of amino acid residues in the albumin fusion protein, and m is defined as any integer ranging from 2 to q minus 6. Polynucleotides encoding these polypeptides are also encompassed by the invention.

Also as mentioned above, even if deletion of one or more amino acids from the N-terminus or C-terminus of a reference polypeptide (e.g., a G-CSF protein; serum albumin protein; or albumin fusion protein of the invention) results in modification or loss of one or more biological functions of the protein, other functional activities (e.g., biological activities, ability to multimerize, ability to bind a ligand) and/or therapeutic activities may still be retained. For example, the ability of polypeptides with C-terminal deletions to induce and/or bind to antibodies which recognize the complete or mature forms of the polypeptide generally will be retained when less than the majority of the residues of the complete or mature polypeptide are removed from the C-terminus. Whether a particular polypeptide lacking the N-terminal and/or C-terminal residues of a reference polypeptide retains therapeutic activity can readily be determined by routine methods described herein and/or otherwise known in the art.

The present invention further provides polypeptides having one or more residues deleted from the carboxy terminus of the amino acid sequence of a G-CSF protein corresponding to a G-CSF protein portion of an albumin fusion protein of the invention. In particular, C-terminal deletions may be described by the general formula 1 to n, where n is any whole integer ranging from 6 to q minus 1, and where q is a whole integer representing the total number of amino acid residues in a reference polypeptide (e.g., a G-CSF protein, or a G-CSF protein portion of an albumin fusion protein encoded by a polynucleotide or albumin fusion construct). Polynucleotides encoding these polypeptides are also encompassed by the invention.

In addition, the present invention provides polypeptides having one or more residues deleted from the carboxy terminus of the amino acid sequence of an albumin protein corresponding to an albumin protein portion of an albumin fusion protein of the invention. In particular, C-terminal deletions may be described by the general formula 1 to n, where n is any whole integer ranging from 6 to 584, where 584 is the whole integer representing the total number of amino acid residues in mature human serum albumin minus 1. Polynucleotides encoding these polypeptides are also encompassed by the invention. In particular, C-terminal deletions may be described by the general formula 1 to n, where n is any whole integer ranging from 6 to 608, where 608 is the whole integer representing the total number of amino acid residues in serum albumin minus 1. Polynucleotides encoding these polypeptides are also encompassed by the invention.

Moreover, the present invention provides polypeptides having one or more residues deleted from the carboxy terminus of an albumin fusion protein of the invention. In particular, C-terminal deletions may be described by the general formula 1 to n, where n is any whole integer ranging from 6 to q minus 1, and where q is a whole integer representing the total number of amino acid residues in an albumin fusion protein of the invention. Polynucleotides encoding these polypeptides are also encompassed by the invention.

In addition, any of the above described N- or C-terminal deletions can be combined to produce a N- and C-terminal deleted reference polypeptide. The invention also provides polypeptides having one or more amino acids deleted from both the amino and the carboxyl termini, which may be described generally as having residues m to n of a reference polypeptide (e.g., a G-CSF protein, or a G-CSF protein portion of an albumin fusion protein of the invention, or serum albumin, or an albumin protein portion of an albumin fusion protein of the invention, or an albumin fusion protein, or an albumin fusion protein encoded by a polynucleotide or albumin fusion construct of the invention) where n and m are integers as described above. Polynucleotides encoding these polypeptides are also encompassed by the invention.

The present application is also directed to proteins containing polypeptides at least about 80%, about 85%, about 90%, about 91%, about 92%, about 93%, about 94%, about 95%, about 96%, about 97%, about 98% or about 99% identical to a reference G-CSF polypeptide or a reference albumin polypeptide set forth herein, or fragments thereof. In preferred embodiments, the application is directed to proteins comprising polypeptides at least about 80%, about 85%, about 90%, about 91%, about 92%, about 93%, about 94%, about 95%, about 96%, about 97%, about 98% or about 99% identical to reference polypeptides having the amino acid sequence of N- and C-terminal deletions as described above. Polynucleotides encoding these polypeptides are also encompassed by the invention.

Preferred polypeptide fragments of the invention are fragments comprising, or alternatively, consisting of, an amino acid sequence that displays a therapeutic activity and/or functional activity (e.g. biological activity) of the polypeptide sequence of the G-CSF protein or serum albumin protein of which the amino acid sequence is a fragment.

Other preferred polypeptide fragments are biologically active fragments. Biologically active fragments are those exhibiting activity similar, but not necessarily identical, to an activity of the polypeptide of the present invention. The biological activity of the fragments may include an improved desired activity, or a decreased undesirable activity.

B. Variants

"Variant" refers to a polynucleotide or nucleic acid differing from a reference nucleic acid or polypeptide, but retaining essential properties thereof. Generally, variants are overall closely similar, and, in many regions, identical to the reference nucleic acid or polypeptide.

As used herein, "variant," refers to a G-CSF protein portion of an albumin fusion protein of the invention, albumin portion of an albumin fusion protein of the invention, or albumin fusion protein of the invention differing in sequence from a G-CSF protein, albumin protein, and/or albumin fusion protein, respectively, but retaining at least one functional and/or therapeutic property thereof as described elsewhere herein or otherwise known in the art. Generally, variants are overall very similar, and, in many regions, identical to the amino acid sequence of the G-CSF protein corresponding to a G-CSF protein portion of an albumin fusion protein, albumin protein corresponding to an albumin protein portion of an albumin fusion protein, and/or albumin fusion protein. Nucleic acids encoding these variants are also encompassed by the invention.

The present invention is also directed to proteins which comprise, or alternatively consist of, an amino acid sequence which is at least about 80%, about 85%, about 90%, about 91%, about 92%, about 93%, about 94%, about 95%, about 96%, about 97%, about 98%, about 99% or about 100%, identical to, for example, the amino acid sequence of a G-CSF protein corresponding to a G-CSF protein portion of an albumin fusion protein of the invention, albumin proteins corresponding to an albumin protein portion of an albumin fusion protein of the invention, and/or albumin fusion proteins. Fragments of these polypeptides are also provided. Further polypeptides encompassed by the invention are polypeptides encoded by polynucleotides which hybridize to the complement of a nucleic acid molecule encoding an albumin fusion protein of the invention under stringent hybridization conditions (e.g., hybridization to filter bound DNA in 6×. Sodium chloride/Sodium citrate (SSC) at about 45 degrees Celsius, followed by one or more washes in 0.2×SSC, 0.1% SDS at about 50-65 degrees Celsius), under highly stringent conditions (e.g., hybridization to filter bound DNA in 6× sodium chloride/Sodium citrate (SSC) at about 45 degrees Celsius, followed by one or more washes in 0.1×SSC, 0.2% SDS at about 68 degrees Celsius), or under other stringent hybridization conditions which are known to those of skill in the art (see, for example, Ausubel, F. M. et al., eds., 1989 Current protocol in Molecular Biology, Green publishing associates, Inc., and John Wiley & Sons Inc., New York, at pages 6.3.1-6.3.6 and 2.10.3). Polynucleotides encoding these polypeptides are also encompassed by the invention.

By a polypeptide having an amino acid sequence at least, for example, 95%-"identical" to a query amino acid sequence, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino- or carboxy-terminal positions of the reference amino acid sequence or anywhere between those terminal positions, interspersed either individually among residues in the reference sequence or in one or more contiguous groups within the reference sequence.

As a practical matter, whether any particular polypeptide is at least about 80%, about 85%, about 90%, about 91%, about 92%, about 93%, about 94%, about 95%, about 96%, about 97%, about 98% or about 99% identical to, for instance, the amino acid sequence of an albumin fusion protein of the invention or a fragment thereof (such as a G-CSF protein portion of the albumin fusion protein or an albumin portion of the albumin fusion protein), can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. 6:237-245 (1990)). In a sequence alignment the query and subject sequences are either both nucleotide sequences or both amino acid sequences. The result of the global sequence alignment is expressed as percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

The variant will usually have at least about 75% (in other embodiments at least about 80%, about 85%, about 90%, about 91%, about 92%, about 93%, about 94%, about 95%, about 96%, about 97%, about 98% or about 99%) sequence identity with a length of normal HA or G-CSF protein which is the same length as the variant. Homology or identity at the nucleotide or amino acid sequence level is determined by BLAST (Basic Local Alignment Search Tool) analysis using the algorithm employed by the programs blastp, blastn, blastx, tblastn and tblastx (Karlin et al., Proc. Natl. Acad. Sci. USA 87: 2264-2268 (1990) and Altschul, J. Mol. Evol. 36: 290-300 (1993), fully incorporated by reference) which are tailored for sequence similarity searching.

The approach used by the BLAST program is to first consider similar segments between a query sequence and a database sequence, then to evaluate the statistical significance of all matches that are identified and finally to summarize only those matches which satisfy a preselected threshold of significance. For a discussion of basic issues in similarity searching of sequence databases, see Altschul et al., (Nature Genetics 6: 119-129 (1994)) which is fully incorporated by reference. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., Proc. Natl. Acad. Sci. USA 89: 10915-10919 (1992), fully incorporated by reference). For blastn, the scoring matrix is set by the ratios of M (i.e., the reward score for a pair of matching residues) to N (i.e., the penalty score for mismatching residues), wherein the default values for M and N are 5 and −4, respectively. Four blastn parameters may be adjusted as follows: Q-10 (gap creation penalty); R=10 (gap extension penalty); wink=1 (generates word hits at every wink.sup.th position along the query); and gapw=16 (sets the window width within which gapped alignments are generated). The equivalent Blastp parameter settings were Q=9; R=2; wink=1; and gapw=32. A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

The polynucleotide variants of the invention may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, polypeptide variants in which less than 50, less than 40, less than 30, less than 20, less than 10, or 5-50, 5-25, 5-10, 1-5, or 1-2 amino acids are substituted, deleted, or added in any combination are also preferred. Polynucleotide variants can be produced for a variety of reasons, e.g., to optimize codon expression for a particular host (change codons in the human mRNA to those preferred by a bacterial host, such as, yeast or *E. coli*).

In a preferred embodiment, a polynucleotide of the invention which encodes the albumin portion of an albumin fusion protein is optimized for expression in yeast or mammalian cells. In a further preferred embodiment, a polynucleotide of the invention which encodes the G-CSF protein portion of an albumin fusion protein is optimized for expression in yeast or mammalian cells. In a still further preferred embodiment, a polynucleotide encoding an albumin fusion protein of the invention is optimized for expression in yeast or mammalian cells.

In an alternative embodiment, a codon optimized polynucleotide which encodes a G-CSF protein portion of an albumin fusion protein does not hybridize to the wild type polynucleotide encoding the G-CSF protein under stringent hybridization conditions as described herein. In a further embodiment, a codon optimized polynucleotide which encodes an albumin portion of an albumin fusion protein does not hybridize to the wild type polynucleotide encoding the albumin protein under stringent hybridization conditions as described herein. In another embodiment, a codon optimized polynucleotide which encodes an albumin fusion protein does not hybridize to the wild type polynucleotide encoding the G-CSF protein portion or the albumin protein portion under stringent hybridization conditions as described herein.

In an additional embodiment, a polynucleotide which encodes a G-CSF protein portion of an albumin fusion protein does not comprise, or alternatively consist of, the naturally occurring sequence of that G-CSF protein. In a further embodiment, a polynucleotide which encodes an albumin protein portion of an albumin fusion protein does not comprise, or alternatively consist of, the naturally occurring sequence of albumin protein. In an alternative embodiment, a polynucleotide which encodes an albumin fusion protein does not comprise, or alternatively consist of, the naturally occurring sequence of a G-CSF protein portion or the albumin protein portion.

Using known methods of protein engineering and recombinant DNA technology, variants may be generated to improve or alter the characteristics of the polypeptides of the present invention. For instance, one or more amino acids can be deleted from the N-terminus or C-terminus of the polypeptide of the present invention without substantial loss of biological function.

In preferred embodiments, the variants of the invention have conservative substitutions. By "conservative substitutions" is intended swaps within groups such as replacement of the aliphatic or hydrophobic amino acids Ala, Val, Leu and Ile; replacement of the hydroxyl residues Ser and Tar; replacement of the acidic residues Asp and Glu; replacement of the amide residues Asn and Gln, replacement of the basic residues Lys, Arg, and H is; replacement of the aromatic residues Phe, Tyr, and Trp, and replacement of the small-sized amino acids Ala, Ser, Thr, Met, and Gly.

Guidance concerning how to make phenotypically silent amino acid substitutions is provided, for example, in Bowie et al., "Deciphering the Message in Protein Sequences: Tolerance to Amino Acid Substitutions," Science 247:1306-1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. See Cunningham and Wells, Science 244:1081-1085 (1989). The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Be; replacement of the hydroxyl residues Ser and Thr; replacement of the acidic residues Asp and Glu; replacement of the amide residues Asn and Gln, replacement of the basic residues Lys. Arg, and His; replacement of the aromatic residues Phe, Tyr, and Trp, and replacement of the small-sized amino acids Ala, Ser, Thr, Met, and Gly. Besides conservative amino acid substitution, variants of the present invention include (i) polypeptides containing substitutions of one or more of the non-conserved amino acid residues, where the substituted amino acid residues may or may not be one encoded by the genetic code, or (ii) polypeptides containing substitutions of one or more of the amino acid residues having a substituent group, or (iii) polypeptides which have been fused with or chemically conjugated to another compound, such as a compound to increase the stability and/or solubility of the polypeptide (for example, polyethylene glycol), (iv) polypeptide containing additional amino acids, such as, for example, an IgG Fc fusion region peptide. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. See Pinckard et al., Clin. Exp. Immunol. 2:331-340 (1967); Robbins et al., Diabetes 36: 838-845 (1987); Cleland et al., Crit. Rev. Therapeutic Drug Carrier Systems 10:307-377 (1993).

In specific embodiments, the polypeptides of the invention comprise, or alternatively, consist of, fragments or variants of the amino acid sequence of an albumin fusion protein, the amino acid sequence of a G-CSF protein and/or human serum albumin, wherein the fragments or variants have 1-5, 5-10, 5-25, 5-50, 10-50 or 50-150, amino acid residue additions, substitutions, and/or deletions when compared to the reference amino acid sequence. In preferred embodiments, the amino acid substitutions are conservative. Nucleic acids encoding these polypeptides are also encompassed by the invention.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POST-TRANSLATIONAL COVALENT MODIFICATION OF PROTEINS, B. C. Johnson, Ed., Academic Press, New York, pgs. 1-12 (1983); Seifter et al., Meth. Enzymol. 182: 626-646 (1990); Rattan et al., Ann. N.Y. Acad. Sci. 663:4862 (1992)).

C. Functional Activity

"A polypeptide having functional activity" refers to a polypeptide capable of displaying one or more known functional activities associated with the full-length, pro-protein, and/or mature form of a G-CSF protein. Such functional activities include, but are not limited to, biological activity, antigenicity [ability to bind (or compete with a polypeptide for binding) to an anti-polypeptide antibody], immunogenicity (ability to generate antibody which binds to a specific polypeptide of the invention), ability to form multimers with polypeptides of the invention, and ability to bind to a receptor or ligand for a polypeptide.

"A polypeptide having biological activity" refers to a polypeptide exhibiting activity similar to, but not necessarily identical to, an activity of a G-CSF protein of the present invention, including mature forms, as measured in a particular biological assay, with or without dose dependency.

In preferred embodiments, an albumin fusion protein of the invention has at least one biological and/or therapeutic activity associated with the G-CSF protein portion (or fragment or variant thereof) when it is not fused to albumin.

The albumin fusion proteins of the invention can be assayed for functional activity (e.g., biological activity) using or routinely modifying assays known in the art, as well as assays described herein. Additionally, one of skill in the art may routinely assay fragments of a G-CSF protein corresponding to a G-CSF protein portion of an albumin fusion protein. Further, one of skill in the art may routinely assay fragments of an albumin protein corresponding to an albumin protein portion of an albumin fusion protein, for activity using assays known in the art and/or as described in the Examples section below.

For example, in one embodiment where one is assaying for the ability of an albumin fusion protein to bind or compete with a G-CSF protein for binding to an anti-G-CSF polypeptide antibody and/or anti-albumin antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In a preferred embodiment, where a binding partner (e.g., a receptor or a ligand) of a G-CSF protein is identified, binding to that binding partner by an albumin fusion protein which comprises that G-CSF protein as the G-CSF protein portion of the fusion can be assayed, e.g., by means well-known in the art, such as, for example, reducing and non-reducing gel chromatography, protein affinity chromatography, and affinity blotting. See generally, Phizicky et al., Microbiol. Rev. 59:94-123 (1995). In another embodiment, the ability of physiological correlates of an albumin fusion protein to bind to a receptor(s) of the G-CSF polypeptide corresponding to the G-CSF protein portion of the fusion can be routinely assayed using techniques known in the art.

In an alternative embodiment, where the ability of an albumin fusion protein to multimerize is being evaluated, association with other components of the multimer can be assayed, e.g., by means well-known in the art, such as, for example, reducing and non-reducing gel chromatography, protein affinity chromatography, and affinity blotting. See generally, Phizicky et al., supra.

Immunoassays which can be used to analyze binding and cross-reactivity and to confirm the identity of a HAS-G-CSF fusion include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety).

Antibodies that bind a G-CSF protein corresponding to the G-CSF protein portion of an albumin fusion protein may also be described or specified in terms of their binding affinity for a given protein or antigen, preferably the antigen which they specifically bind. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M. More preferred binding affinities include those with a dissociation constant or Kd less than $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M or $10^{-8}$ M. Even more preferred binding affinities include those with a dissociation constant or Kd less than $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M. In addition, assays described herein and otherwise known in the art may routinely be applied to measure the ability of albumin fusion proteins and fragments, variants and derivatives thereof to elicit biological activity and/or G-CSF activity (either in vitro or in vivo) related to either the G-CSF protein portion and/or albumin portion of the albumin fusion protein. Other methods will be known to the skilled artisan and are within the scope of the invention.

VI. HSA-G-CSF FUSION PROTEIN

Recombinant human albumin-human granulocyte colony stimulating factor (rHSA-G-CSF) is a G-CSF analogue.

Examples of rHSA-G-CSFs are described in U.S. Pat. No. 5,665,863 and in U.S. Pat. No. 7,041,478 hereby incorporated by reference.

Another example of rHSA-G-CSF is Neugranin™ which is being developed by Teva Biopharmaceuticals USA LTD. Neugranin™ ("NEUG") is a 759 amino acid fusion polypeptide with a molecular mass of approximately 85 kDa connected in a single chain. Residues 1-585 correspond to the mature form of HSA, and residues 586-759 correspond to the mature form of human G-CSF. The Neugranin™ fusion polypeptide is shown in FIG. 9.

VII. PRODUCING THE FUSION PROTEIN

Examples of the synthetic process of manufacture of rHSA-G-CSF are described in U.S. patent application Ser. No. 11/929,828 hereby incorporated by reference in its entirety. In some embodiments, NEUG is produced using a yeast host system (Saccharomyces cerevisiae) genetically engineered to express the NEUG fusion protein. NEUG is harvested from the fermentation medium of the yeast culture and purified using methods well known in the art (e.g., by a series of chromatography and filtration steps, such as affinity chromatography and ion exchange chromatography).

In one non-limiting example, a NEUG fusion construct was developed as follows. The full-length albumin cDNA was isolated from a human cDNA library in the laboratory of Dr. F. E. Baralle at the University of Oxford, UK. This clone was sent to Delta Biotechnology Limited, Nottingham, UK, as the plasmid pAT153ALB. In addition, the 6-amino acid HSA pro-peptide (RGVFRR (SEQ ID NO: 1)) was modified to facilitate more efficient processing in yeast (RSLDKR (SEQ ID NO: 2)).

The Neugranin production plasmid is based on the 2-µ plasmid found in wild type Saccharomyces cerevisiae. The pSAC35-based expression vector (patents EP 286 424 B, U.S. Pat. No. 5,637,504) contains the LEU2 gene from Saccharomyces cerevisiae as a selectable marker that complements the leucine-deficiency of the production host. This production plasmid also contains a strong yeast promoter, PRB1, and sequences from plasmid pUC9 that permit cloning and propagation in E. coli. In addition, the plasmid exhibits the unique attribute in which it eliminates the pUC9-derived sequences required for propagation in E. coli once transformed into yeast. This is accomplished by flanking FLP recognition targets and the expression of the yeast FLP recombinase from the plasmid once in yeast. Thus, no bacterial DNA is present in the organism used for production of NEUG. This is confirmed by rescue and sequence of the 2 µm plasmid from the yeast after the master cell bank is generated.

As described above, the NEUG production plasmid, termed CID1643 (pSAC35:HSA.GCSF(T31-P204)), was derived from the pSAC35-based expression vector. The region corresponding to T31-P204 of human G-CSF was amplified by PCR, while adding the appropriate 5' and 3' restriction sites to permit a seamless fusion to the 3'-end of the HSA open reading frame.

NEUG seed vials were used to prepare a cGMP master cell bank (MCB) at Human Genome Sciences, Inc., (HGS) in Rockville, Md. The testing and characterization of the NEUG MCB was undertaken at Charles River Laboratories (Malvern, Pa., USA) and Lark Technologies (Houston, Tex., USA) in compliance with the ICH guideline Q5D (Derivation and Characterization of Cell Substrates Used for Production of Biotechnological/Biologicals Products).

A cGMP working cell bank (WCB) derived from this MCB was subsequently generated and tested at Charles River Laboratories (Malvern, Pa., USA).

All media components used in the manufacture of the NEUG cell line banks were synthetic, biosynthetic or plant derived. No components of animal or human origin were used during cell line or cell bank preparation.

The cell banks is stored at <−135° C. in a cryopreservation media in pre-sterilized 1.8 mL Nunc polypropylene tubes with internally threaded caps.

Non-limiting, exemplary methods of isolating, purifying and preparing the rHSA-G-CSF fusion protein for pharmaceutical use are provided below, in the Experimental Examples.

VIII. PREPARATION OF THERAPEUTIC PROTEINS

Therapeutic proteins in their native state or when recombinantly produced, such as interferons and growth hormones, are typically labile molecules exhibiting short shelf-lives, particularly when formulated in aqueous solutions. The instability in these molecules when formulated for administration dictates that many of the molecules must be lyophilized and refrigerated at all times during storage, thereby rendering the molecules difficult to transport and/or store. Storage problems are particularly acute when pharmaceutical formulations must be stored and dispensed outside of the hospital environment. Albumin fusion proteins comprising a therapeutic protein have demonstrated extended shelf life compared to the shelf life of the same therapeutic protein when not fused to albumin. Shelf-life typically refers to the time period over which the therapeutic activity of a therapeutic protein in solution or in some other storage formulation, is stable without undue loss of therapeutic activity.

Nevertheless, aggregation and chemical instability are major obstacles in developing formulations for albumin fusion proteins comprising a therapeutic protein. Aggregation of pharmaceutical formulations can be very deleterious since it reduces activity, and increases drug clearance due to the aggregate's immunogenic activity (Pinckard et al. 1967; Robbins et al. 1987; Cleland et al., 1993).

Presented below are a number of non-limiting examples which illustrate various aspects of the methods and compositions described herein.

IX. EXPERIMENTAL EXAMPLES

The following examples are given to illustrate the present invention. It should be understood, however, that the invention is not to be limited to the specific conditions or details described in these examples. All publicly available documents referenced herein, including but not limited to US patents, are hereby incorporated by reference.

In Examples 1, 2, and 6, three different, non-limiting formulations of pharmaceutical Neugranin™ ("NEUG") compositions are presented. Each formulation comprises the NEUG fusion polypeptide shown in FIG. 9. The method and resulting composition described in section A are broadly referred to as "NEUG-0." The method and resulting composition described in section B are broadly referred to as "NEUG-1," and the method and resulting composition described in section E are broadly referred to as "NEUG-2."

NEUG is a fusion polypeptide with a molecular mass of approximately 85 kDa connected in a single chain comprising residues 1-585 corresponding to the mature form of HSA, and residues 586-759 corresponding to the mature form of human G-CSF. The amino acid sequence of NEUG fusion protein is shown in FIG. 9.

Example 1

Preparation of Therapeutic NEUG-0

NEUG-0 was manufactured for use in toxicology experiments. The formulation included NEUG at 4.0 mg/ml in 10 mM citrate, 75 mM sodium chloride, 100 mM sucrose, 0.01% polysorbate 80, and was buffered to pH 6.5.

Safety/Toxicology

The non-clinical safety of NEUG was assessed in monkeys. Repeat exposure (once-weekly for 4 weeks) at 100, 500, 1000 µg/kg NEUG was well tolerated, with no mortality, morbidity, or changes in body weight or food consumption. There were not gross or microscopic changes that were considered adverse toxicities. Treatment related observations were limited to expected pharmacology of G-CSF administration (e.g., neutrophilia, slight increase in spleen weight, myeloid hyperplasia) and were not considered toxicities. The NOAEL in monkey was >1 mg/kg/week, which was ~12 fold higher than observed following a dose of 0.45 mg/kg in humans. Treated animals also showed an increase in ANC and WBC. (Data not shown).

Example 2

Preparation of Therapeutic NEUG-1

NEUG-1 was manufactured for clinical studies in humans. The formulation included NEUG at 15.0 mg/ml, in PMMT10/7.2 (10 mM sodium phosphate, 200 mM mannitol, 60 mm trehalose dehydrate, 0.01% (W/V) polysorbate-80, at pH 7.2.

The composition of NEUG-1 is provided in Table 1, below.

TABLE 1

Composition of NEUG-1 Drug Product

| Ingredient | Concentration | Amount deliverable per vial[a] | Grade | Purpose |
|---|---|---|---|---|
| Neugranin | 15.0 mg/mL | 15.0 mg | | API |
| Sodium phosphate monobasic | 0.44 mg/mL (3 mM) | 2.42 mg | USP, multi-compendial | Buffering agent |
| Sodium phosphate dibasic | 0.97 mg/mL (7 mM) | 0.35 mg | USP, multi-compendial | Buffering agent |
| Mannitol | 36.4 mg/mL (200 mM) | 32.79 mg | USP, multi-compendial | Buffering agent |
| Trehalose dihydrate | 22.70 mg/mL (60 mM) | 22.7 mg | High purity | Cryoprotectant |
| Polysorbate 80 | 0.1 mg/mL (0.01%) | 0.1 mg | USP, multi-compendial | Inhibit aggregation |
| Sterile WFI | Reconstitute with 1.0 mL | 1.0 mL | USP | Diluent |

[a]A 0.16 mL overage is included in each vial to assure the 1.0 mL deliverable volume.

One exemplary method for the manufacture of bulk drug substance ("BDS") for NEUG-1 is shown by the non-limiting process steps of FIG. 13. The BDS is then stored at about −80° C. (nominal value, acceptable range of storage temperature is about −65° C.).

To improve the robustness of the formulation for shipping and storage at clinical sites, as well as to provide a stable product with an expected long shelf life, a lyophilized form of NEUG-1 has been developed. Methods of freeze-drying are well known in the art, and one exemplary method, which forms elegant, lyophilized cakes, was performed as described in the following steps.

Step 1: Thawing and Dilution of Bulk Drug Substance

Containers of NEUG bulk drug substance are thawed at 15 to 30° C. The bulk drug substance is pooled (if necessary), mixed, and protein concentration determined by absorbance at 280 nm. The bulk drug substance concentration is used to calculate the amount of dilution buffer required. Density and pH are also measured. Formulation buffer is used to dilute the bulk drug substance to the desired final concentration.

Step 2: Sterile Filtration

The diluted solution is transferred from the formulation area into a sterile receiving vessel through sterile filters that have been integrity tested. The filtration-train consists of two 0.2 µm PVDF filters in series. All filters are previously unused and are integrity tested and disposed of post-manufacturing.

Step 3: Filling and Partial Stoppering

Neugranin is filled into depyrogenated 3 mL USP Type I glass vials, partially stoppered, and trayed onto bottomless lyophilization trays. Weight checks are performed throughout the filling operation to verify fill volume.

Step 4: Lyophilization

The lyophilization cycle is controlled by chamber pressure and shelf temperature. Product temperature is monitored by product thermocouples placed throughout the lyophilization chamber. Partially stoppered vials are loaded onto pre-chilled shelves and frozen at a controlled rate. An annealing step is performed to promote crystallization of mannitol (bulking agent). Primary drying is then performed and verified by monitoring thermocouples. Secondary drying is performed to achieve the desired moisture content. At the end of secondary drying, the vacuum in the lyophilization chamber is released by venting 0.2 µm sterile-filtered nitrogen into the chamber.

Step 5: Sealing and Capping

The stoppers are seated into the vials under a partial vacuum (ca 11-12 psia). The product trays are unloaded and the vials are capped.

The initial lyophilized clinical material (NEUG-1) has proven quite stable, with a current shelf-life of 2 years (when stored at 2-8° C.) which will likely be further extended as data from continuing stability studies is reviewed.

Example 3

General Properties of a NEUG-1 Reference Standard, Lot 2378-R

A variety of methods have been developed to examine the physiochemical and biological characteristics of NEUG. One lot of NEUG termed reference standard Lot 2378-R, contains 21.3 mg/mL NEUG and was formulated in 10 mM sodium phosphate, 200 mM mannitol, 60 mM trehalose dehydrate, and 0.01% (w/v) polysorbate 80 at pH 7.2 (PMTT10/7.2). Physicochemical characterization was performed on the reference standard lot and the test attributes, analytical methods and a summary of results is provided in Table 2, below.

TABLE 2

Characterization of NEUG-1 lot 2378-R

| Attribute | Analytical Method | Lot 2378-R (NEUG-1) |
|---|---|---|
| Appearance | Visual inspection | Clear, pale yellow |
| pH | pH electrode | 7.3 |
| Protein concentration | $A_{280}$ | 21.3 mg/mL |
| Osmolality | Freezing Point | 313 mOsm/kg |
| Purity | SDS-PAGE (Reduced and Nonreduced, Coomassie blue stain) | Reduced: 99% Nonreduced: 98% |
| Purity | SEC-HPLC | 97.4% |
| Purity | RP-HPLC | 83.9% |
| Charge Heterogeneity | IEC-HPLC | 84.8% |
| Purity | SDS-PAGE (silver stain) | Established as reference standard (No bands present at >1% of main band) |
| Bioburden | Membrane filtration | 0 cfu/10 mL |
| Endotoxin | Kinetic turbidimetric | 0.293 EU/mg |
| Residual DNA | Threshold | <4 pg/mg |
| Identity | ELISA | Identity confirmed |
| Intact Mass (expected 85086) | ESI/MS | 85087 Da |
| Identity (Expected: DAHKS (Residues 1-5 of SEQ ID NO: 4)) | N-terminal sequencing | >95% DAHKS (Residues 1-5 of SEQ ID NO: 4) |
| Identity | Peptide Map (reducing) | Established as reference standard (>96% sequence covered) |
| Yeast Host Cell Protein | ELISA | 49 ng/mg |
| Potency | Bioassay (NFS60 cell proliferation) | $EC_{50}$ = 197.6 ± 41.6 pg/mL (established as ref. std.) |

SDS-PAGE analysis of NEUG-1 Lot 2378-R with Coomassie blue stain results in a single band (FIG. 19). A representative SEC-HPLC and RP-HPLC chromatogram of NEUG-1 Lot 2378-R is also shown in FIGS. 19A and 19B, respectively.

Example 4

Testing NEUG-0 and NEUG-1 Formulations

1. Effect of Protein Concentration on rHSA-G-CSF Monomer Purity

Recombinant human albumin-human granulocyte colony stimulating factor (rHSA-G-CSF) at concentrations ranging from 2.5 to 240 mg/ml was incubated in PMTT10/7.2 (10 mM Phosphate, 190 mM mannitol, 60 mM trehalose dihydrate, 0.01% (W/V) polysorbate 80, pH 7.2) at 25° C. for 24 hours. Subsequent to incubation, monomer purity was measured by SE-HPLC.

The results (FIG. 1) show that aggregation increased with increasing rHSA-G-CSF concentration.

2. Effect of pH on rHSA-G-CSF Aggregation

Recombinant human albumin-human granulocyte colony stimulating factor at a concentration of 15 mg/ml and 60 mg/ml was incubated at 25° C. for 7 days in PMTT10 (10 mM Phosphate, 190 mM Mannitol, 60 mM Trehalose Dihydrate, 0.01% (W/V) Polysorbate 80) at a pH of 6.0, 6.8, 7.2, and 8.0. Subsequent to incubation rHA-G-CSF monomer purity was measured by SE-HPLC.

Figure 2:
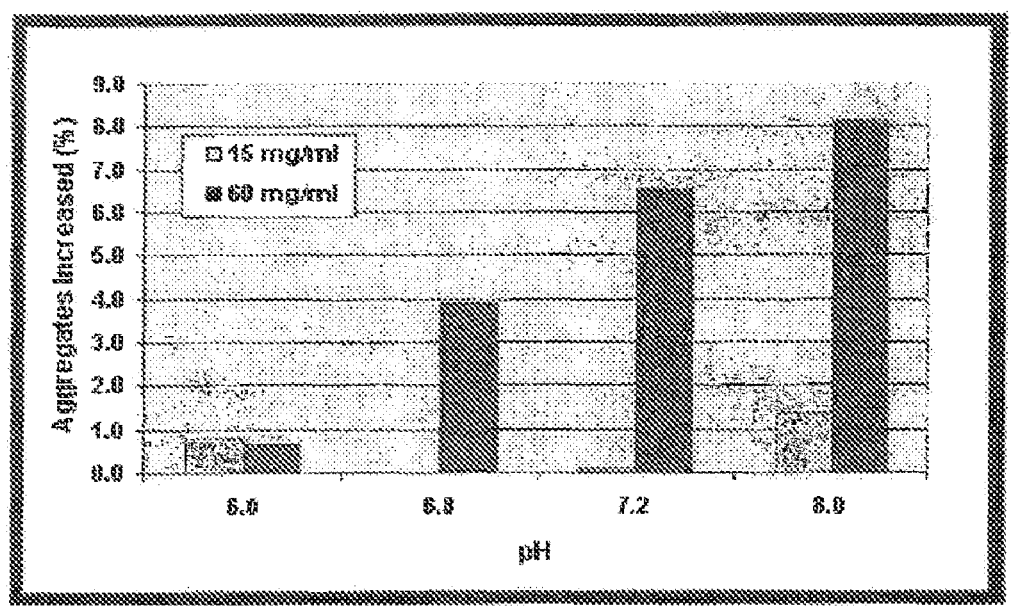
FIG. 2 is a graph showing that increasing pH increases rHSA-G-CSF aggregation. Aggregation of rHSA-G-CSF at a concentration of 15 mg/ml or 60 mg/ml was measured by SE-HPLC after incubation at 25° C. for 7 days in PMTT10 at a pH of 6.0, 6.8, 7.2, or 8.0.

The results (FIG. 2) demonstrate that aggregation increased with increasing pH, and accelerated by increased protein concentration.

3. Effect of Temperature on rHSA-G-CSF Aggregation

Recombinant human albumin-human granulocyte colony stimulating factor at a concentration of 60 mg/ml was incubated in PMTT10/7.2 buffer at 4° C., 25° C., or 40° C. for 24 hours. Subsequent to incubation rHSA-G-CSF monomer purity was measured by SE-HPLC.

Figure 3:
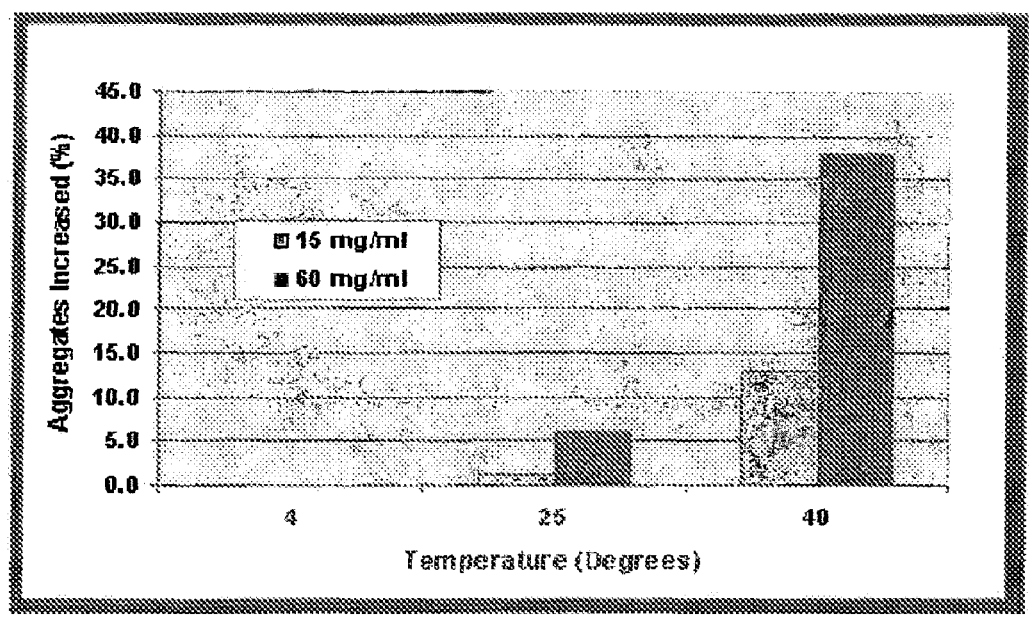
FIG. 3 is a graph showing that increasing temperature increases rHSA-G-CSF aggregation. Aggregation of rHSA-G-CSF at a concentration of 15 mg/ml or 60 mg/ml was measured by SE-HPLC after incubation at 4° C., 25° C., or 40° C. for 24 hours in PMTT10/7.2.

The results (FIG. 3) demonstrate that aggregation was accelerated with increasing temperature.

4. Effect of pH on rHSA-G-CSF Aggregation

Recombinant human albumin-human granulocyte colony stimulating factor at a concentration of 48 mg/ml was incubated at 25° C. for up to 3 days in PMTT10 (10 mM phosphate, 190 mM mannitol, 60 mM trehalose dihydrate, 0.01% (W/V) polysorbate 80) at a pH of 5.8, 6.3, 6.4, or 7.0, or in CMTT10 (10 mM sodium citrate, 190 mM mannitol, 60 mM trehalose dihydrate, 0.01% (W/V) polysorbate 80) buffer at a pH of 6.2. Recombinant human albumin-human granulocyte colony stimulating factor monomer purity was measured by SE-HPLC at day 0, 1, 2, and 3 after incubation.

Figure 4:
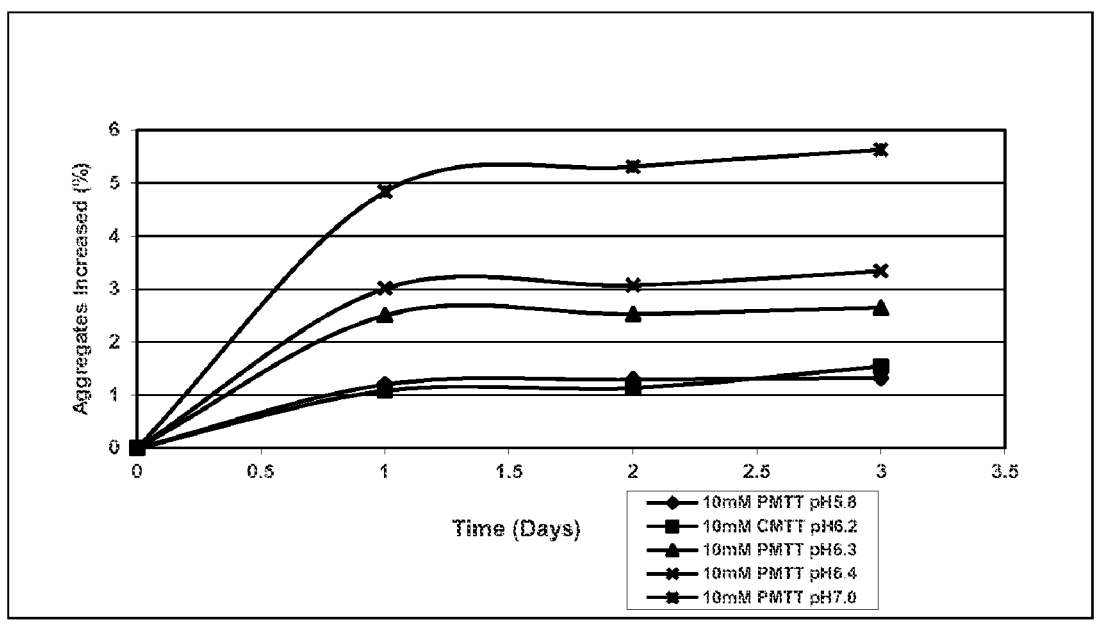
FIG. 4 is a graph showing that increasing pH increases rHSA-G-CSF aggregation. Aggregation of rHSA-G-CSF at a concentration of 48 mg/ml was measured by SE-HPLC after incubation at 25° C. for up to 3 days in PMTT10 at a pH of 5.8, 6.3, 6.4, or 7.0, or in CMTT10 at a pH of 6.2. The top line is 10 mM PMTT pH 7.0; the line second from the top is 10 mM PMTT pH 6.4; The third line from the top is 10 mm PMTT pH 6.3; the darker of the lowest lines is 10 mM PMTT pH 5.8; the lighter of the lowest lines is 10 mM CMTT pH 6.2.

The results (FIG. 4, and FIG. 10) demonstrate that most of the aggregation occurred in the first day of incubation and that the rate of aggregation increased due to increasing pH.

5. Effect of pH on rHSA-G-CSF Aggregation

Recombinant human albumin-human granulocyte colony stimulating factor at a concentration of 15 mg/ml or 60 mg/ml was incubated at 4° C., 25° C., or 40° C. for up to 10 days in PMTT10 at a pH of 6.0, 6.8, 7.2, or 8.0. Monomer purity was measured by SE-HPLC at day 0, 1, 7, and 10 after incubation.

The results (FIG. 11) demonstrate that aggregation increased with increasing pH, and accelerated by increased temperature and protein concentration.

6. Effect of pH on rHSA-G-CSF Bioactivity

Recombinant human albumin-human granulocyte colony stimulating factor at a concentration of 15 mg/ml or 60 mg/ml was incubated at 4° C., 25° C., or 40° C. for up to 10 days in PMTT10 at a pH of 6.0, 6.8, 7.2, or 8.0. Bioactivity was measured by Bioassay at day 0, and either day 7 or day 10 after incubation.

Briefly, NFS-60 cells proliferate in response to both G-CSF and NEUG. In this assay, 10,000 cell/well were plated in a 96 well microplate and were treated with NEUG proteins for 20 hours at 37° C. After a 20-hour incubation the NFS-60 cells were pulsed with 0.5 µCi/well of [3H]-Thymidine for 4 hours, and the level of DNA synthesis, as measured by [3H]-Thymidine incorporation, was determined. For statistical analysis, the measurement of [3H]-Thymidine incorporation as a function of NEUG concentration was modeled using a four-parameter logistic model and EC50 values (pg/mL) were determined. Results for test proteins are reported as a relative potency (RP %) value, generated by comparing EC50 value of reference standard to the EC50 of the test sample analyzed within the same assay [RP %=(EC50 reference/EC50 sample)*100].

The results (FIG. 12) demonstrate that activity of rHSA-G-CSF was better maintained when incubated in low pH.

7. Effects of Salt Concentration on Aggregation of rHSA-G-CSF

The ionic strength of the rHA-G-CSF 60 mg/ml solutions was controlled by altering the amount of sodium chloride in the solution. The formulation buffer was PMTT10/7.2. Samples were incubated for 1 day at 25° C./60% RH, at a sodium chloride concentration of 5 mM, 10 mM, 20 mM, or 50 mM, and subsequently tested by SE-HPLC.

Figure 5:
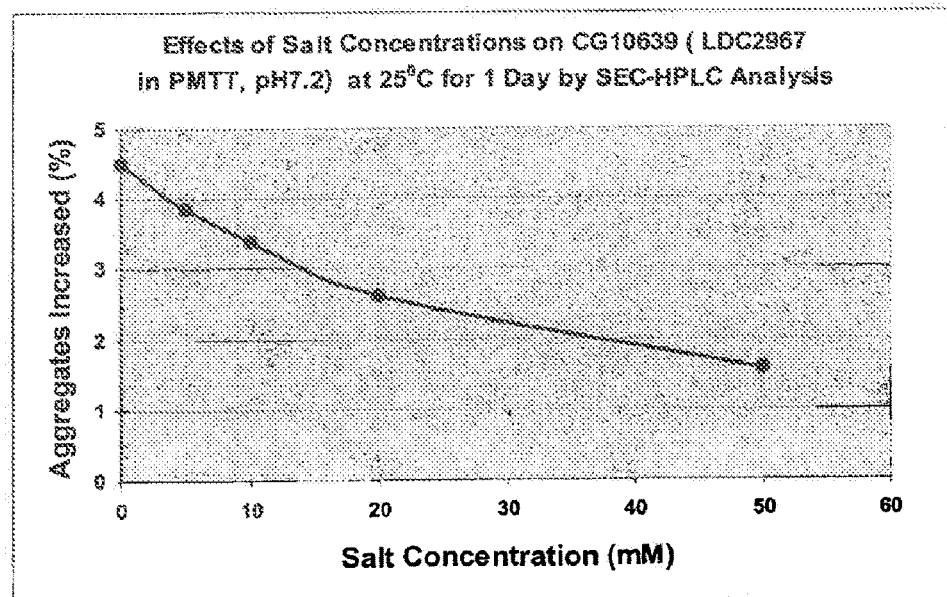
FIG. 5 is a graph showing that increasing salt concentration decreases rHSA-G-CSF aggregation. Aggregation of rHSA-G-CSF at a concentration of 60 mg/ml was measured by SE-HPLC after incubation for 1 day at 25° C./60% RH in PMTT10/7.2 and at a sodium chloride concentration of 5 mM, 10 mM, 20 mM, or 50 mM.

The results show that increasing the salt concentration decreased rHSA-G-CSF aggregation (FIG. 5).

8. Effects of Phosphate Concentration on Aggregation of rHSA-G-CSF

The ionic strength of the rHSA-60 mg/ml G-CSF solutions was controlled by altering the amount of phosphate in the solution. The formulation buffer was PMTT pH 7.2. Samples were incubated for 1 day at 25° C./60% RH, and at a phosphate concentration of 15 mM, 20 mM, 25 mM, 30 mM, 40 mM, or 50 mM and subsequently tested by SE-HPLC.

Figure 6:
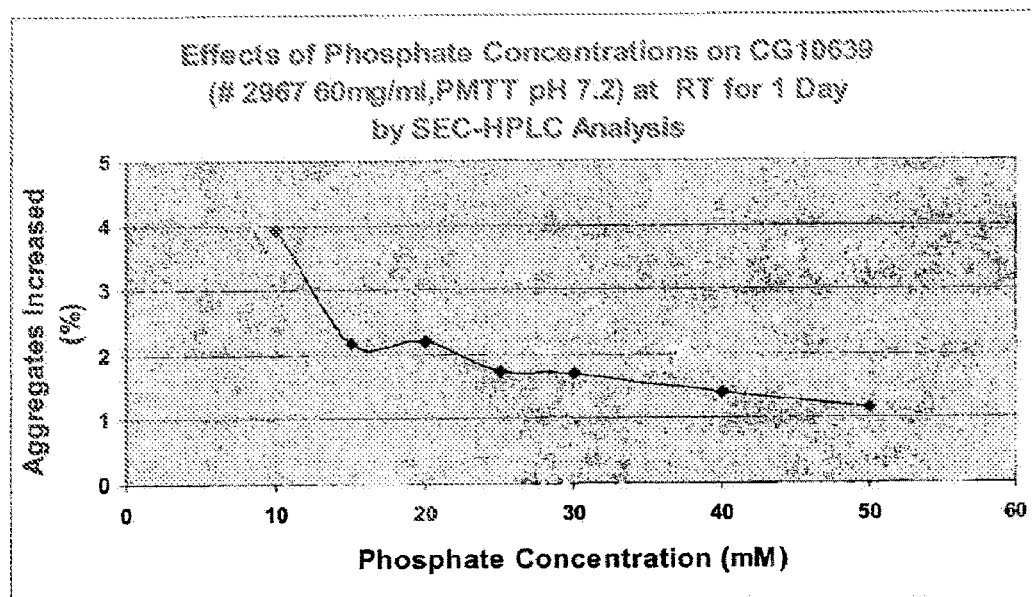
FIG. 6 is a graph showing that increasing phosphate concentration decreases rHSA-G-CSF aggregation. Aggregation of rHSA-G-CSF at a concentration of 60 mg/ml was measured by SE-HPLC after incubation for 1 day at 25° C./60% relative humidity ("RH") in PMTT/7.2 and at a phosphate concentration of 15 mM, 20 mM, 25 mM, 30 mM, 40 mM, or 50 mM.

The results show that increasing the phosphate concentration decreased rHSA-G-CSF aggregation (FIG. 6).

Example 5

Preparation of Therapeutic NEUG-2

NEUG-2 was manufactured for clinical studies for use and administration at higher concentrations. The formulation included NEUG at 50.0 mg/ml in PMMT20/6.0 (20 mM sodium phosphate, 180 mM mannitol, 60 mM trehalose, 0.01% polysorbate-80).

Essentially, the same process of fermentation and purification was followed as shown for NEUG-1 (see e.g., FIG. 13).

NEUG-2 was prepared both as a liquid and in lyophilized form. The lyophilized form was prepared to improve the robustness of the formulation for shipping and storage at clinical sites, as well as to provide a stable product with an expected long shelf life. NEUG-2 was freeze-dried using the identical freeze-dry cycle as described for NEUG-1. The NEUG-2 formulation also produced well-formed, pharmaceutically elegant cakes.

Example 6

Comparison of NEUG-0, NEUG-1 and NEUG-2 Formulations

Table 3 shows the physiochemical comparability of NEUG-0, the standard lot of NEUG-1 (reference standard 2378-R) and three different lots of NEUG-2. In the table, "CP" means clear, pale yellow. "ND" means not determined.

TABLE 3

Physiochemical comparability of NEUG-0, NEUG-1 and NEUG-2

| Attribute | Analytical Method | NEUG-0 Toxicology (lot 2579-092) | NEUG-1 Current ref std (2378-R) | NEUG-2 Clinical lot 071008005 | NEUG-2 Clinical lot 071025001 | NEUG-2 Clinical lot 071026004 |
|---|---|---|---|---|---|---|
| Appearance | Visual inspection | CP | CP | CP | CP | CP |
| pH | pH electrode | 6.5 | 7.3 | 6.0 | 6.0 | 6.0 |
| Protein concentration | $A_{280}$ | 4.7 mg/mL | 21.3 mg/mL | 64.5 | 61.4 | 62.0 |
| Osmolality | Freezing point depression | 316 mOsm/kg | 313 mOsm/kg | 305 mOsm/kg | 310 mOsm/kg | 313 mOsm/kg |
| Purity | SDS-PAGE (Reduced and Nonreduced, Coomassie blue stain) | Reduced: 97% Nonreduced: 92% | Reduced: 100% Nonreduced: 95% | Reduced: 100% Nonreduced: 100% | Reduced: 100% Nonreduced: 100% | Reduced: 100% Nonreduced: 100% |
| Purity | SEC-HPLC | 97.5% | 97.5% | 98.9% | 99.4% | 98.1% |
| Purity | RP-HPLC | 73.0% | 82.5% | 86.3% | 88.5% | 87.5% |
| Charge Heterogeneity | IEC-HPLC | 52.8% | 80.5% | 89.5% | 88.0% | 89.5% |
| Purity | SDS-PAGE (silver stain) | Comparable | Comparable | Comparable | Comparable | Comparable |
| Intact Mass (expected 85086) | ESI/MS | 85091 Da | 85087 Da | ND | ND | ND |
| Identity (expected: DAHKS (Residues 1-5 of SEQ ID NO: 4)) | N-terminal sequencing | 92% DAHKS (Residues 1-5 of SEQ ID NO: 4), 3% TYGEM (Residues 84-88 of SEQ ID NO: 4) | >95% DAHKS (Residues 1-5 of SEQ ID NO: 4) | >95% DAHKS (Residues 1-5 of SEQ ID NO: 4) | >95% DAHKS (Residues 1-5 of SEQ ID NO: 4) | >95% DAHKS (Residues 1-5 of SEQ ID NO: 4) |
| Identity | Peptide Map (reducing) | Comparable | Comparable | Comparable | Comparable | Comparable |
| Yeast Host Cell Protein | ELISA (ng yHCP/mg protein) | 198 ppm | 49 ppm | 39 ppm | 19 ppm | 20 ppm |

TABLE 3-continued

Physiochemical comparability of NEUG-0, NEUG-1 and NEUG-2

| Attribute | Analytical Method | NEUG-0 Toxicology (lot 2579-092) | NEUG-1 Current ref std (2378-R) | NEUG-2 Clinical lot 071008005 | NEUG-2 Clinical lot 071025001 | NEUG-2 Clinical lot 071026004 |
|---|---|---|---|---|---|---|
| Potency | Bioassay-NFS60 cell proliferation (% relative potency) | 80.9% | 100.0% | 113% | 80% | 87% |
| Endotoxin | Kinetic turbidimetric | 1.67 EU/mg | 0.293 EU/mg | <0.003 EU/mg | <0.003 EU/mg | <0.003 EU/mg |
| Residual DNA | Threshold | <4 pg/mg | <4 pg/mg | ND | ND | ND |

Process related impurities (e.g., yeast host cell proteins) and product related variants (SEC, RP, and IEC-HPLC) have been consistently reduced as the processes for manufacturing NEUG-0 through NEUG-2 have been developed.

Tables 4 and 5 provide a summary of the formulation history and formulation comparison of NEUG-0, NEUG-1 and NEUG-2.

TABLE 4

Formulation history

| Process | Form | Recommended storage temperature | Formulation |
|---|---|---|---|
| NEUG-0 (toxicology) | Frozen liquid | −20° C. | 2.94 mg/mL sodium citrate 4.38 mg/mL sodium chloride 34.23 mg/mL sucrose 0.01% polysorbate 80 pH 6.5 |
| NEUG-1 (initial clinical) | Lyophilized cake | 2-8° C. | 1.41 mg/mL sodium phosphate 36.4 mg/mL mannitol 22.7 mg/mL trehalose dihydrate 0.1 mg/mL polysorbate 80 pH 7.2 |
| NEUG-2 (current clinical) | Lyophilized cake | 2-8° C. | 2.77 mg/mL sodium phosphate 33.79 mg/mL mannitol 22.7 mg/mL trehalose dihydrate 0.1 mg/mL polysorbate 80 pH 6.0 |
| NEUG-2 (current clinical) | Liquid | 2-8° C. | 2.77 mg/mL sodium phosphate 33.79 mg/mL mannitol 22.7 mg/mL trehalose dihydrate 0.1 mg/mL polysorbate 80 pH 6.0 |

TABLE 5 cGMP formulation comparison

| Excipient Formulation Attribute | Initial Clinical (NEUG-1) | Current Clinical formulation (liquid or lyophilized form) (NEUG-2) | Rationale for change |
|---|---|---|---|
| API | 15.0 mg/mL | 50 mg/mL | Increased API concentration to reduce volume of injection |
| Sodium Phosphate | 10 mM | 20 mM | Higher ionic strength reduces concentration dependent aggregation |
| Mannitol | 200 mM | 180 mM | Reduced to provide iso-osmotic solution |
| Trehalose dihydrate | 60 mM | 60 mM | Unchanged-acts as robust cryo/lyo protectant. |
| Polysorbate 80 | 0.01% | 0.01% | Unchanged-inhibits nonspecific aggregation and adsorption |

TABLE 5-continued cGMP formulation comparison

| Excipient Formulation Attribute | Initial Clinical (NEUG-1) | Current Clinical formulation (liquid or lyophilized form) (NEUG-2) | Rationale for change |
|---|---|---|---|
| pH | 7.2 | 6.0 | Lower pH reduces concentration dependent aggregation |

Example 7

Testing NEUG-1 and NEUG-2

1. Effects of pH and Phosphate Concentration on Monomer Purity of rHSA-G-CSF

Figure 7:
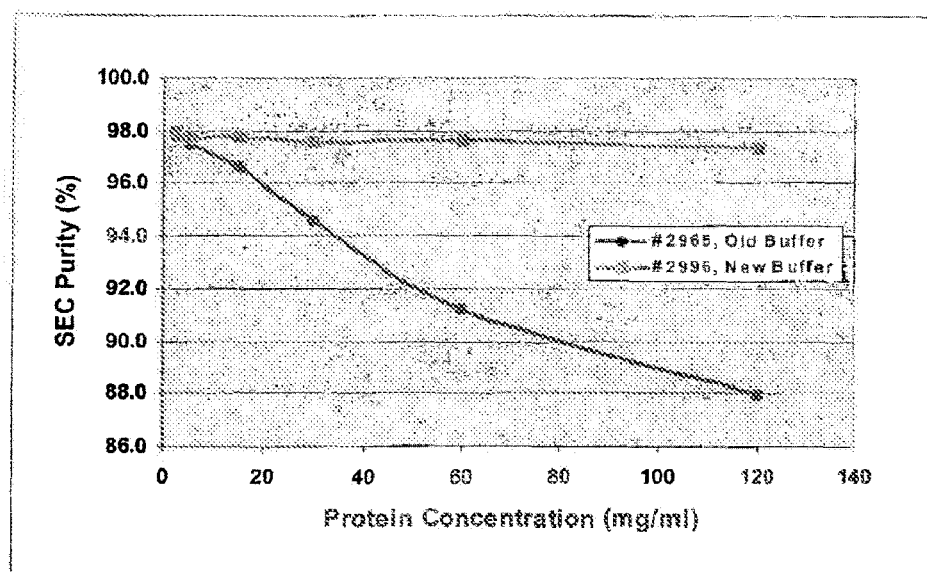
FIG. 7 is a graph showing that purity of rHSA-G-CSF is maintained at concentrations of up to 120 mg/ml in PMTT20/6.0 formulation buffer. Monomer purity of rHSA-G-CSF samples at concentrations ranging from 2.5 to 120 mg/ml was measured by SE-HPLC after incubation in PMTT10/7.2 (old buffer), or PMTT20/6.0 (new buffer) at 25° C. for 24 hours.

The results displayed in FIG. 7, show monomer purity measured by SE-HPLC of NEUG in PMTT10/7.2 and in PMTT20/6.0 (20 mM Phosphate, 180 mM Mannitol, 60 mM Trehalose Dihydrate, 0.01% (W/V) Polysorbate 80, pH 6.0) respectively. Samples contained different protein concentrations at a range of 2.5 to 120 mg/ml, and were incubated at 25° C. for 24 hours prior to purity analysis.

Results show no significant reductions of purity were observed with rHA-G-CSF at concentrations of up to 120 mg/ml in PMTT20/6.0 formulation buffer as measured by SE-HPLC, whereas in PMTT10/7.2 there was a 10% aggregation increase.

2. Effects of pH and Phosphate Concentration on Aggregation of rHA-G-CSF

Figure 8:
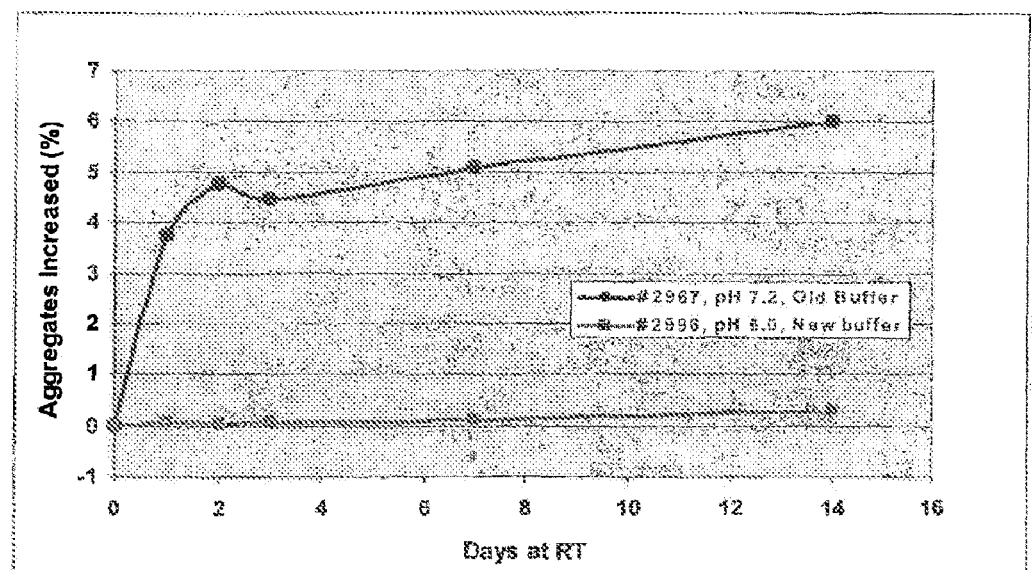
FIG. 8 is a graph showing how pH and phosphate concentration effect aggregation of rHSA-G-CSF. Aggregation of rHSA-G-CSF at a concentration of 60 mg/ml was measured by SE-HPLC after incubation at 4° C. or 25° C./60% RH for a maximal period of 14 days in PMTT10/7.2 (old buffer) or in PMTT20/6.0 (new buffer).

The results displayed in FIG. 8, show aggregation measured by SE-HPLC of 60 mg/ml rHA-G-CSF incubated at 4° C. or 25° C./60% RH for a maximal period of 14 days in PMTT20/6.0 or in PMTT10/7.2.

Results show no significant aggregation increase was observed after incubation at 25° C. for 14 days for samples incubated in PMTT20/6.0 formulation buffer whereas samples incubated under the same conditions in PMTT10/7.2 formulation buffer showed a 6% increase in aggregation.

3. HPLC Comparison of NEUG-1 Versus NEUG-2

Figure 14A:
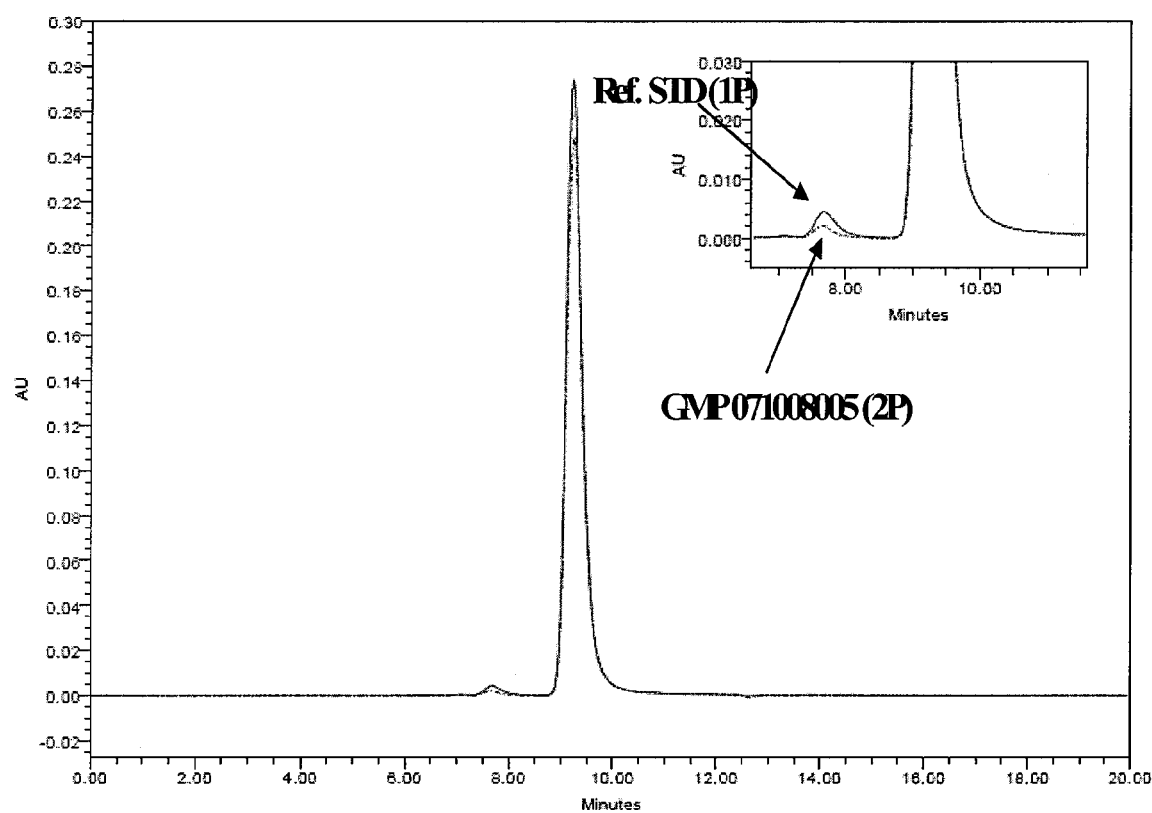
FIGS. 14A and 14B show the results of SEC-HPLC and RP-HPLC, respectively, comparing NEUG-1 ("1P") and NEUG-2 ("2P").
Figure 14B:
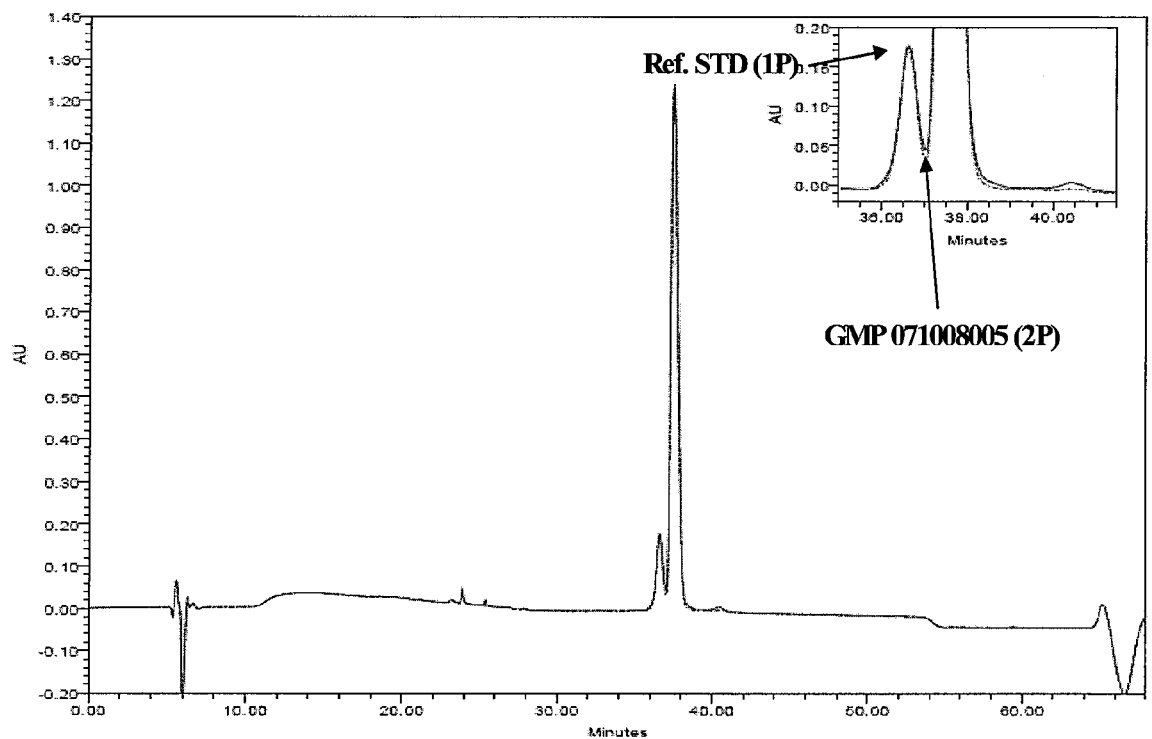

SEC-HPLC analysis and RP-HPLC analysis of NEUG-1 and NEUG-2 is shown in FIGS. 14A and 14B.

4. Charge Comparability, Peptide Mapping and Purity of NEUG-1 and NEUG-2

Figure 15A:
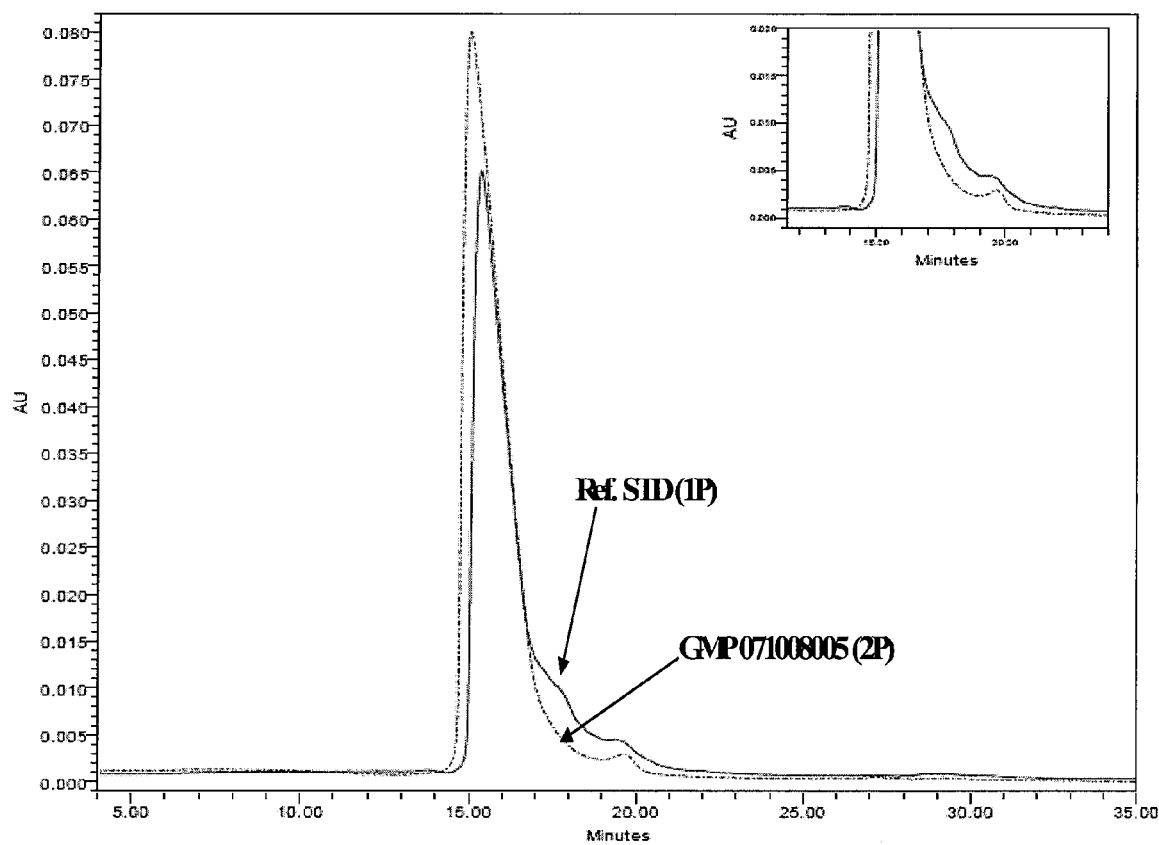
FIGS. 15A and 15B show the comparability of charge heterogeneity by IEC-HPLC and the comparability of identity by peptide mapping, respectively, of NEUG-1 ("1P") and NEUG-2 ("2P").
Figure 15B:
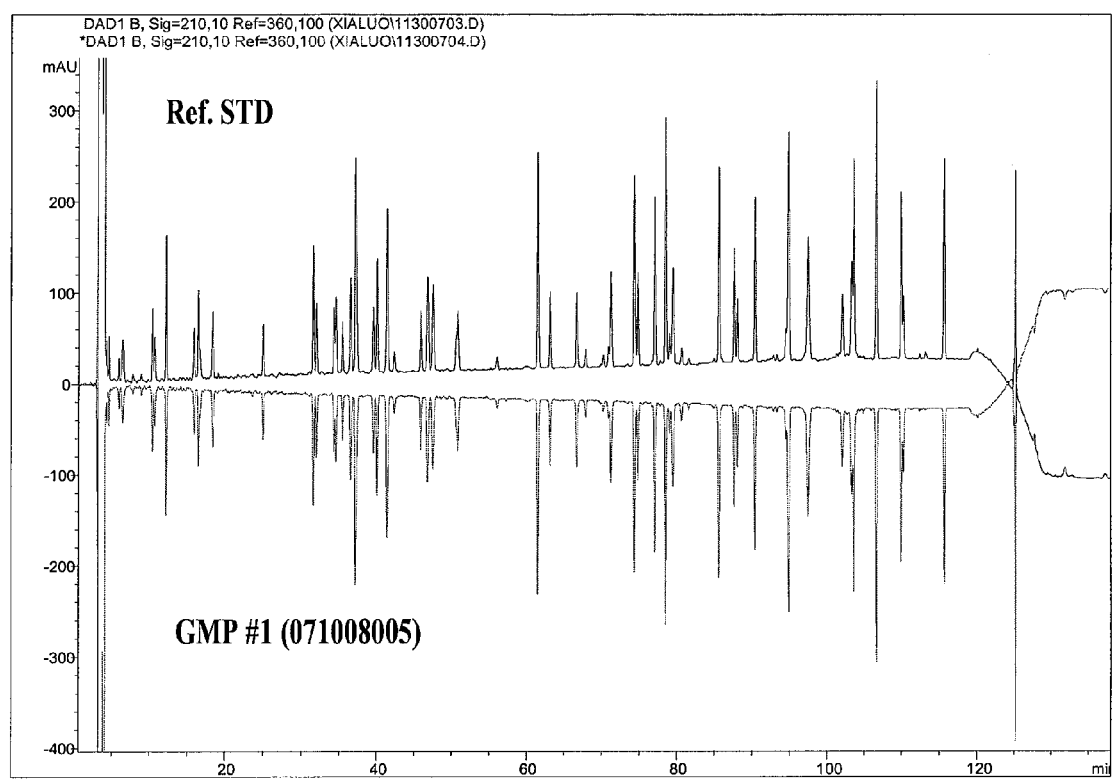

The charge heterogeneity of NEUG-1 (referred to as "1P" in the figure) and NEUG-2 (referred to as "2P" in the figure) were compared by IEC-HPLC. Results are shown in FIG. 15A. The identity of the two peptides (NEUG-1, "1P" and NEUG-2, "2P") was also compared by peptide mapping as shown in FIG. 15B.

Figure 16:
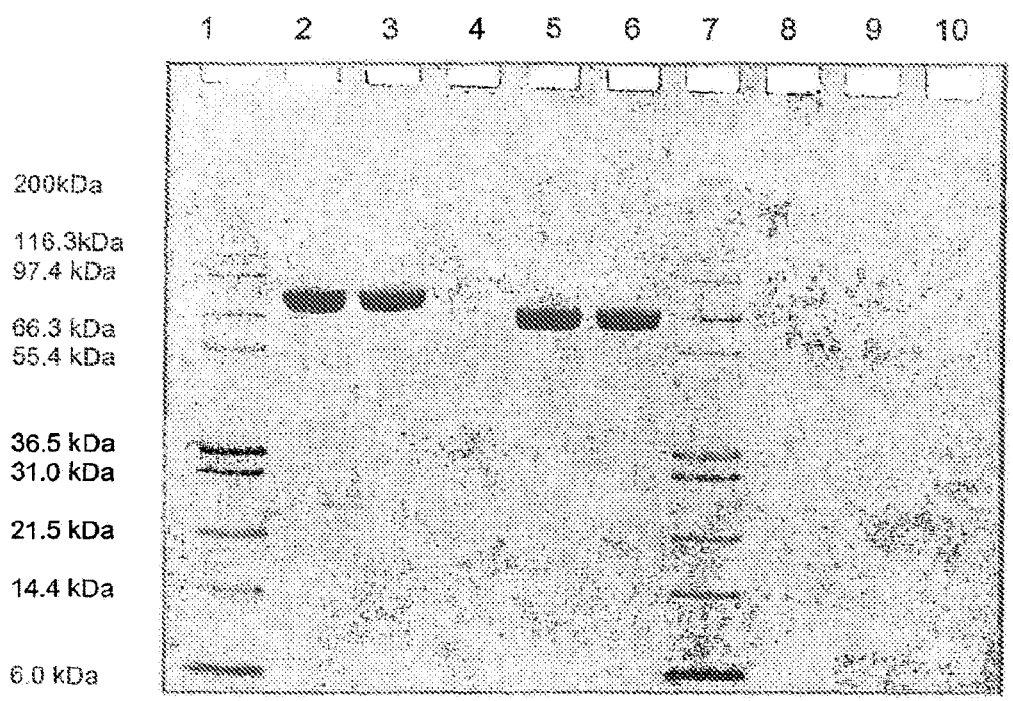
FIG. 16 shows the comparable purity of NEUG-1 versus NEUG-2 on an SDS-PAGE gel, stained with Coomassie blue.
Figure 18:
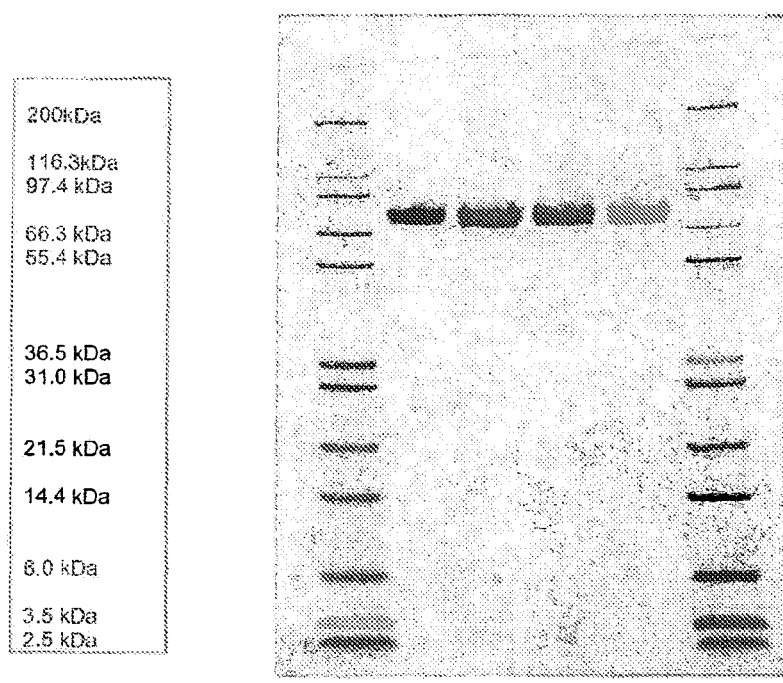
FIG. 18 shows Coomassie-stained SDS-PAGE analysis (reduced) of the Lot 2378-R NEUG-1 reference standard.

Purity of NEUG-1 and NEUG-2 was also compared by SDS-PAGE and Coomassie blue staining as shown in FIG. 16. The samples in each lane are shown in Table 6, below.

TABLE 6

Samples loaded onto SDS-PAGE of FIG. 16

| Lane # | Lot | Description | Conditions | Load (µg) |
|---|---|---|---|---|
| 1 | 1373336 | Size Marker 12 | NA | NA |
| 2 | (NEUG-1) LDC-2378-R | CG10639 Reference Standard | Reduced | 4 µg |
| 3 | (NEUG-2) 071025001 | CG10639 Bulk | Reduced | 4 µg |
| 4 | NA | NA | NA | NA |
| 5 | (NEUG-1) LDC-2378-R | CG10639 Reference Standard | Non-Reduced | 4 µg |
| 6 | (NEUG-2) 071025001 | CG10639 Bulk | Non-Reduced | 4 µg |
| 7 | 1373336 | Size Marker 12 | NA | NA |
| 8 | NA | NA | NA | NA |
| 9 | NA | NA | NA | NA |
| 10 | NA | NA | NA | NA |

5. Freeze-Thaw

The effects of Freeze-Thaw were evaluated with NEUG-2 (in PMTT20/6.0) buffer with concentration 15, 60, 120 mg/ml. Samples were frozen and thawed from 0 to 10 times, then analyzed via visual inspection and SEC, RP, IEC.

Results indicate that Neugranin does not appear to be sensitive to freeze-thaw induced degradation for both old (PMTT10/7.2) and new (PMTT20/6.0) formulation buffers. (Data not shown).

6. Short-Term Stability

Samples of NEUG (60 mg/ml) in old buffer (PMTT10/7.2) and new buffer (PMTT20/6.0) were kept at 4 and 25° C./60% RH for one month, then tested by visual inspection, SEC, RP, IEC and Bio-assay. Monomer purity was evaluated by SE-HPLC.

At 14 days, NEUG in the old buffer showed 6% aggregates increased, while NEUG in the new buffer showed no changes. There were no significant changes for one month by visual, RP, IEC and Bio-assay.

7. Shaking

The effect of shaking-induced aggregation was evaluated with NEUG in old formulation buffer (PMTT10/7.2) new formulation buffer (MPTT20/6.0) at three conditions (15, 60, 120 mg/ml), pH 6.0. Each sample was shaken horizontally at 120 rpm from 0 to 30 min at 25° C. Visual inspection and SE-HPLC were performed.

The Results of the SE-HPLC, RP-HPLC, IE-HPLC displayed no significant loss of monomer. (Data not shown). Furthermore, the results from visual inspection indicate no change in appearance as a result of shaking. This suggests that Neugranin may not be sensitive to shaking-induced aggregation for both old and new formulation buffers.

8. Oxidation

Figure 21:
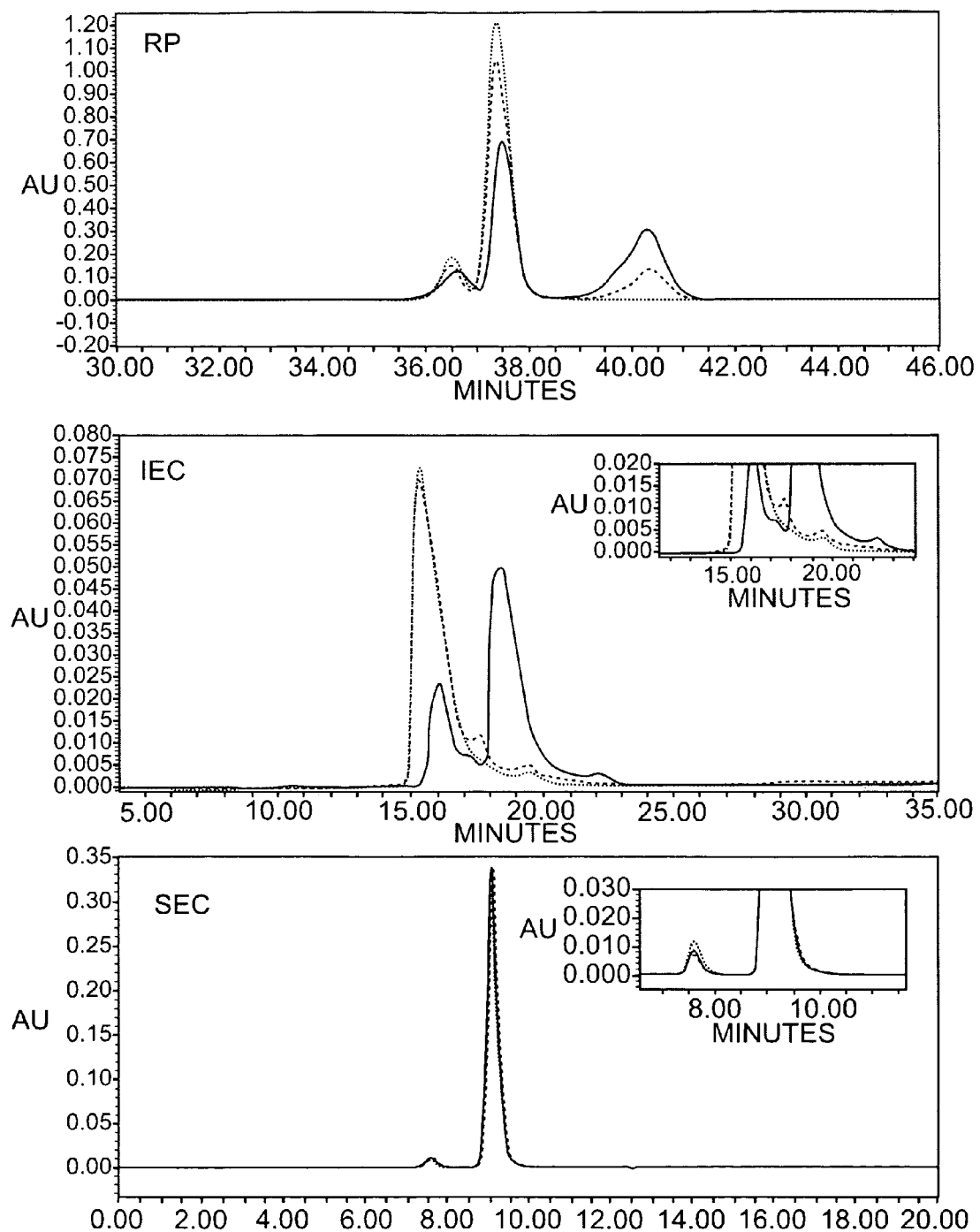
FIG. 21 shows chromatograms of reverse phase ("RP"), ion-exchange ("IE") and size exclusion ("SEC") chromatography of NEUG treated with hydrogen peroxide and TBO or TBP; studies were performed to monitor oxidation of NEUG. NEUG control=medium grey; NEUG treated with hydrogen peroxide=light grey; NEUG treated with TBP=black.

Ion-exchange high performance liquid chromatography ("IEC") and reversed phase-high performance liquid chromatography ("RPLC") can be used to monitor oxidation of Neugranin. The experimental conditions for the hydrogen-peroxide study are as follows. Neugranin at 8 mg/mL were exposed to 0.03% hydrogen peroxide and TBO. Samples were analyzed by size exclusion chromatography ("SEC"), reverse phase ("RP"), and IEC after incubation at 25° C. for 0, 1, 3, 5, 8, 20, and 24 hours. For assessment of hydrogen peroxide and TPB induced oxidation, RPLC, IEC were used. Chromatographs and data in tabular form are shown in FIGS. 21 and 22.

HSA has been shown to oxidize in the presence of hydrogen peroxide. The sites of oxidation identified include Cys-34, Met-123, Met-298, Met-446, and Met-548.

The chromatograms (FIG. 21) show the overlays for NEUG control (grey), after exposure to hydrogen peroxide (light grey), and TPB (black) for 1 hour at RT. A significant increase in a peak eluting 3 minutes after the main peak is shown in samples treated with $H_2O_2$ by RP and IEC; samples treated with TPB show a peak eluting 3 minutes after the main peak by RP and the peaks slightly increased and eluted 2, 3 minutes later than main peak by IEC.

In summary, the results suggest that RP and IEC can detect different oxidized forms, and both $H_2O_2$ and TBP could induce NEUG oxidations at which are methionine and cystein residues. The oxidation of NEUG does occur under stressed conditions, but there is no indication that it represents a major degradation pathway for NEUG upon storage and there are no significant changes on their activities.

Example 8

Exemplary Characterization of NEUG for Pharmaceutical Use

Three cGMP drug substance lots were produced using the NEUG-1 process and 5 lots were produced using the NEUG-2 process. In general, the NEUG-2 formulation yielded protein of equal or better quality relative to NEUG-0 and NEUG-1. The test results for all cGMP lots are provided in the tables in FIG. 17A-B. NEUG-1 lots are 060615001, 060628001, and 060707001. NEUG-2 lots are 071008005, 071025001, 071026004, 071106001, and 07116001. Testing of the lots was performed as follows.

1. Appearance by Visual Inspection

The appearance of Neugranin™ ("NEUG") was assessed by visual inspection using forward illuminating fluorescent light against a black and white background.

2. pH

The pH meter was standardized using buffer solutions at pH 4.0, 7.0, and 10.0. After standardization, the pH of a sample of NEUG was measured and recorded.

3. Osmolality by Freezing Point

The osmolality was determined by freezing point depression. Standardization was performed using a 290 mOsm/kg calibration standard prior to measurement.

4. Concentration by Measuring the Absorbance at 280 nm

The concentration of NEUG was determined by measuring the absorbance at 280 nm. Protein concentration was calculated using the empirically determined extinction coefficient of 0.54 $mg^{-1}$*mL*AU.

5. Identity by ELISA

The identity assay used a standard sandwich ELISA format using methods well known in the art. The assay was based on the specificity of antibodies for both the G-CSF and albumin portions of the NEUG molecule. Together this antibody pair can distinguish NEUG from G-CSF, HSA, or other albumin-linked proteins.

6. Purity by Coomassie Stained SDS-PAGE

The purity of NEUG under denaturing conditions was evaluated using SDS-PAGE with Coomassie stain. Samples were diluted in sample buffer with or without reducing agent prior to analysis. Molecular weight markers and a NEUG reference standard were also loaded onto each gel. After electrophoresis, the gel was stained with Coomassie and the purity determined using densitometry. This method is used primarily to detect product-related impurities such as dimers.

7. Purity by Silver Stained SDS-PAGE

The purity of NEUG under denaturing conditions was evaluated using overloaded SDS-PAGE with silver staining. Samples were diluted in sample buffer with or without reducing agent prior to analysis. Samples were loaded up to 10 μg/lane. Molecular weight markers and a NEUG reference standard were also loaded onto each gel. After electrophoresis, the gel was stained with silver. Comparisons between migration distances and band patterns are used to determine comparability between NEUG samples and reference standard. This method was used to detect low levels of product and process-related impurities.

8. Purity by Size Exclusion HPLC

The purity of NEUG under native conditions was evaluated using size exclusion HPLC. Samples were analyzed using a TosoHaas G3000SWXL column (7.8 mm×30 cm) with an isocratic mobile phase consisting of phosphate and sulfate. Purity of NEUG was determined by calculating the ratio of the area under the main peak to the total peak area at 280 nm. This assay detects product-related sizing impurities, including dimers and aggregates.

9. Purity by Reversed Phase HPLC

Reversed phase HPLC was used to measure the purity of NEUG. Samples were analyzed using an Agilent Zorbax reversed phase column (StableBond C8, 300 Å, 4 μm, 250× 4.6 mm) with an elution gradient of increasing acetonitrile concentration. Purity was determined by calculating the ratio of the main peak area to total relevant peak area at a detection wavelength of 215 nm.

The peak preceeding the main peak in the RP-HPLC assay has a mass consistent with a Neugranin variant containing a di-hexose modification at Thr-133 of the G-CSF moiety. This modification does not affect potency and was present at consistent levels in all development, toxicology, and cGMP batches manufactured to-date. Thr-133 is a known site for modification of G-CSF.

10. Potency by Bioassay (NFS-60 Cell Proliferation)

The NEUG potency assay is a cell based proliferation assay, based on the induction of NSF-60 cell proliferation. NFS-60 cells proliferate in response to both G-CSF and NEUG. In this assay, 10,000 cell/well were plated in a 96-well microplate and were treated with NEUG proteins for 20 hours at 37° C. After a 20-hour incubation the NFS-60 cells were pulsed with 0.5 μCi/well of [3H]-Thymidine for 4 hours, and the level of DNA synthesis, as measured by [3H]-Thymidine incorporation, was determined. For statistical analysis, the measurement of [3H]-Thymidine incorporation as a function of NEUG concentration was modeled using a four-parameter logistic model and EC50 values (pg/mL) are determined. Results for test proteins were reported as a relative potency (RP %) value, generated by comparing EC50 value of reference standard to the EC50 of the test sample analyzed within the same assay [RP %=(EC50 reference/EC50 sample)*100].

11. Residual DNA by Threshold Method

The method for measuring residual DNA in samples is based on a commercially available kit (Molecular Devices Total DNA Threshold DNA quantification kit). The sample was initially diluted, protein digested, and the DNA extracted. The concentration of DNA was then quantified using the Threshold kit. This kit immuno-labels, immobilizes, and electrochemically measures the concentration of DNA relative to a calf thymus DNA standard curve. The results were internally qualified by spike recovery of DNA standard within acceptable limits.

12. Endotoxin by Kinetic Turbidimetric Method

Endotoxin concentrations in NEUG solutions were determined using a standard automated kinetic turbidimetric endotoxin analysis system. The kinetic turbidimetric system is a refinement of the gel-clot method, and measures turbidity increases that precede gel-clot formation. *Limulus* amoebocyte lysate (LAL) was added to the standards and test articles and incubated at 37° C. During incubation, the turbidity of the reaction mixture was monitored spectrophotometrically. Turbidity was proportional to the endotoxin concentration. The rate of turbidity formation in the test article is compared with the turbidity formation in the standard curve of known standard concentrations.

13. Bioburden by Membrane Filtration

The membrane filtration method is similar to the United States Pharmacopoeia (USP <61>) Microbial Limits Test that estimates the number of viable organisms present in a sample. In the membrane filtration method, the organisms are captured out of the test solution on a membrane filter, which is then plated on a suitable growth medium. A sample volume of 10 mL of test article is diluted in 90 mL of sterile phosphate buffered saline (PBS) prior to testing. The entire 100 mL of diluted test article is filtered. After the filtration step, the filter membrane is transferred to Heterotrophic Plate Count (HPC) agar and incubated at 30 to 35° C. for 2 to 3 days. The HPC agar differs from the Soybean Casein Digest Agar (SCD, which is also called TSA) cited in USP <61>. HPC agar is designed to recover a broad range of aerobic, heterotrophic bacteria, as is TSA. However, HPC agar is also designed to maximize recovery of stressed organisms.

14. Tungsten Study

It is known that certain syringe brands contain tungsten as an excipient. Liquid NEUG samples were tested in the presence of various forms of tungsten (sodium tungstate dehydrate, sodium polytungstate, ammonium tungstate, and tungsten oxides WO3 and WO2) at various concentrations (500 ppb, 1000 ppb and 2500 ppb) at 2-8° C. and 25° C. for up to three months. Samples were analyzed by SE-HPLC, RP-HPLC and bioassay. There were no significant effects of tungsten on NEUG samples after three month stability studies.

15. Characterization Assays

The following analytical were also used for characterization information.

N-Terminal Sequence

The amino acid sequence at the N-terminus of Neugranin was identified using a PE Applied Biosystems Procise 494 cLC protein sequencer. The method incorporates Edman degradation chemistry and utilizes gas-phase blot cycles, an on-line PTH-amino acid HPLC analyzer, and SequencePro data analysis software.

Charge Heterogeneity by IE-HPLC

IEC-HPLC was used to measure the relative abundance of charge heterogeneity present in NEUG. Samples were analyzed using a Dionex Pro-Pac Wax 10-ion exchange column (250×4.6 mm) with mobile phases consisting of Bis-Tris and NaCl. This method has demonstrated sample-independent variability and at this point in development is used as a qualitative rather than quantitative assay.

Peptide Mapping

Peptide mapping is used to determine the structure integrity of NEUG. Peptide mapping was performed using Lys-C for digestion and reversed-phase HPLC with gradient elution for peptide separation. The protein sample was first reduced and denatured and then alkylated. A buffer exchange was carried out, followed by a 1 hour, then overnight, Lys-C digestion. The Lys-C peptide mixture resulting from the digestion was separated by reversed-phase HPLC to give a peptide profile using an YMC Pack ODS-A C18 column (4.6 mm×250 mm) with an Agilent 1100 HPLC system. The HPLC elution was monitored using a diode array UV detector and Finigan LCQ DUO-Ion Trap mass spectrometer with electrospray ionization. Mass spectrometry data were processed using Xcalibur V2.3 software. The mass accuracy of this method was less than 20 ppm. The identities of HPLC peaks were established by LC-MS.

Electrospray Ionization Mass Spectrometry

Mass analyses were performed using an Applied Biosystems QStar ESI-Quadrapole Time of Flight (QTOF) Pulsar-i mass spectrometer equipped with a PicoView nano-electrospray source. Samples were introduced into QStar by Hamiliton syringe and Harvard syringe pump. The electrospray ion source was operated at 2500V with a curtain gas value of 25. The instrument was calibrated with myoglobin. The mass to charge ratios were recorded by scanning the full mass range (500-3000 m/z) within the mass analyzer every second throughout the allotted time of analysis. The resulting total ion current was analyzed using Analyst v1.4 software. The mass accuracy of the instrument is less than 10 ppm.

Residual *S. cerevisiae* (Yeast) Host Cell Protein

The amount of yeast host cell protein (yHCP) present in the bulk was determined using an ELISA based on custom antibodies raised by immunization with host cell proteins derived from a null strain of the same yeast host used to express NEUG.

Free thiol by Ellman's Assay

Ellman's reagent, 5,5'-Dithio-bis-(2-nitrobenzoic acid) (DTNB) was used to determine the free thiol content in NEUG samples. DTNB reacts with free sulfhydryl groups to yield a mixed disulfide and 2-nitro-5-thiobenzoic acid (TNB). TNB absorbs strongly at 412 nm allowing the reaction to be easily quantitated by comparison to a N-acetyl Cysteine (NAC) standard curve. To increase the accuracy of the method, the reaction was carried out under partially denaturing conditions. This allows the DTNB access to free sulfhydryl groups that may not be fully exposed under native conditions.

16. Stability

Bulk drug substance ("BDS") is stored and shipped at −80° C. (nominal value, acceptable temperature is ≦−65° C.). BDS stability was studied by storing the product at the −80° C. and accelerated storage conditions. The reference standard (NEUG-1, Lot 2378-R) was placed on stability first to provide leading stability for GMP BDS and an understanding of the stability of the reference standard itself. Typically for each process (NEUG-1, NEUG-2) at least one development and one cGMP lot was placed on stability, with each study detailed in a study-specific protocol that follows ICH guidelines. Standard accelerated conditions were used to define assay suitability and likely degradation pathways, as well as help predict expiration. The stability was monitored by appearance, pH, protein concentration, osmolality, SEC-HPLC, RP-HPLC, SDS-PAGE, and bioassay.

A summary of the representative stability results for NEUG 1 reference standard lot 2378 is summarized below in Tables 7-9 below.

TABLE 7

Stability data for NEUG-1 Lot 2378-R (−80° C.)

| Attributes | Time (months) −80° C. | | | | | | | |
|---|---|---|---|---|---|---|---|---|
| | 0 | 3 | 6 | 9 | 12 | 18 | 24 | 36 |
| Appearance (Visual inspection) | CPF | CPF | CPF | CPF | CPF | CPF | CPF | CPF |
| pH | 7.3 | 7.2 | 7.4 | 7.3 | 7.2 | 7.3 | 7.3 | 7.2 |
| Osmolality (mOsm/kg) | 313 | 321 | 306 | 308 | 310 | 316 | 306 | 311 |
| Concentration (A280) (mg/mL) | 21.9 | 20.9 | 22.8 | 22.5 | 22.9 | 23.1 | 22.8 | 22.5 |
| Purity (SDS-PAGE), Reduced (%) | 99 | 100 | 100 | 100 | 100 | 100 | 100 | 100 |
| Purity (SDS-PAGE), Non-reduced (%) | 98 | 100 | 100 | 100 | 100 | 100 | 100 | 100 |
| Purity (SEC-HPLC) (%) | 97.4 | 97.3 | 97.5 | 97.7 | 97.9 | 98.4 | 97.7 | 97.0 |
| Purity (RP-HPLC) MP (%) | 83.9 | 84.1 | 85.4 | 85.2 | 84.7 | 84.0 | 83.5 | 82.5 |
| P-1 (%) | 12.5 | 12.8 | 12.2 | 12.4 | 12.5 | 12.6 | 12.1 | 12.5 |
| MP + P-1 (%) | 96.4 | 96.9 | 97.6 | 97.6 | 97.2 | 96.6 | 95.6 | 94.9 |
| Purity (IE-HPLC) (%) | 84.8 | 85.2 | 85.3 | 82.9 | 82.4 | 78.0 | 74.0 | 74.6 |
| Potency (relative potency, bioassay) (%) | 84.3 | 123 | 102 | 133 | 99 | 86 | 90.4 | 110 |
| Bioburden (CFU/10 mL) | 0 | | | | | | | 0 CFU/1 mL |

CPF = clear, pale yellow, essentially free from foreign particulate matter

TABLE 8

Stability data for NEUG-1 Lot 2378-R (−20° C.)

| Attributes | Time (months) −20° C. | | | | | |
|---|---|---|---|---|---|---|
| | 0 | 3 | 6 | 9 | 12 | 18 |
| Appearance (Visual inspection) | CPF | CPF | CPF | CPF | CPF | CPF |
| pH | 7.3 | 7.2 | 7.3 | 7.3 | 7.3 | 7.3 |
| Osmolality (mOsm/kg) | 313 | 323 | 291 | 306 | 300 | 306 |
| Concentration (A280) (mg/mL) | 21.9 | 21.1 | 22.4 | 22.9 | 22.4 | 22.5 |
| Purity (SDS-PAGE), Reduced (%) | 99 | 100 | 100 | 100 | 100 | 100 |
| Purity (SDS-PAGE), Non-reduced (%) | 98 | 100 | 100 | 100 | 100 | 100 |
| Purity (SEC-HPLC) (%) | 97.4 | 96.7 | 97.4 | 97.4 | 97.7 | 98.2 |
| Purity (RP-HPLC) MP (%) | 83.9 | 84.6 | 85.5 | 84.7 | 84.1 | 83.9 |
| P-1 (%) | 12.5 | 12.6 | 12.3 | 12.4 | 12.6 | 12.6 |
| MP + P-1 (%) | 96.4 | 97.2 | 97.8 | 97.2 | 96.7 | 96.4 |
| Purity (IE-HPLC) (%) | 84.8 | 84.8 | 84.0 | 84.4 | 82.2 | 76.9 |
| Potency (relative potency, bioassay) (%) | 84.3 | 112 | 101 | 98.8 | 90.6 | 97.6 |

TABLE 9

Stability data for NEUG-1 Lot 2378-R (2-8° C.)

| Attributes | Time (months) 2-8° C. | | | | |
|---|---|---|---|---|---|
| | 0 | 3 | 6 | 9 | 12 |
| Appearance (Visual inspection) | CPF | CPF | CPF | CPF | CPF |
| pH | 7.3 | 7.2 | 7.3 | 7.3 | 7.2 |
| Osmolality (mOsm/kg) | 313 | 326 | 307 | 315 | 323 |
| Concentration (A280) (mg/mL) | 21.9 | 22.4 | 23.2 | 21.8 | 22.7 |
| Purity (SDS-PAGE), Reduced (%) | 99 | 100 | 100 | 100 | 100 |
| Purity (SDS-PAGE), Non-reduced (%) | 98 | 100 | 100 | 100 | 100 |
| Purity (SEC-HPLC) (%) | 97.4 | 96.6 | 97.5 | 98.3 | 98.5 |
| Purity (RP-HPLC) MP (%) | 83.9 | 84.0 | 84.6 | 83.7 | 82.6 |
| P-1 (%) | 12.5 | 12.5 | 12.0 | 12.4 | 12.4 |
| MP + P-1 (%) | 96.4 | 96.5 | 96.6 | 96.0 | 94.9 |
| Purity (IE-HPLC) (%) | 84.8 | 84.4 | 80.4 | 77.8 | 68.6 |
| Potency (relative potency, bioassay) (%) | 84.3 | 98 | 107 | 128 | 99.9 |

No significant changes in any parameter were seen out to 36 months at the recommended storage condition, out to 18 months at −20° C. or out to 12 months at 2-8° C.

1 month data is shown for the NEUG-2. No significant changes under the recommended storage conditions, at −20° C. or at 2-8° C. are noted. Table 10.

TABLE 10

Stability data for NEUG-2

| Attributes | Time (months) −80° C. | | Time (months) −20° C. | | Time (months) 2-8° C. | |
|---|---|---|---|---|---|---|
| | 0 | 1 | 0 | 1 | 0 | 1 |
| Appearance (visual inspection) | CP | CP | CP | CP | CP | CP |
| Concentration (A280) (mg/ml) | 57.5 | 58.3 | 57.5 | 60.8 | 57.5 | 58.7 |
| pH | 6.0 | 6.0 | 6.0 | 6.0 | 6.0 | 6.0 |
| % Purity (SE-HPLC) | 99.2 | 98.5 | 99.2 | 98.6 | 99.2 | 98.7 |
| % Purity (SDS-PAGE) reduced (%) | 100 | 100 | 100 | 100 | 100 | 100 |
| % Purity (SDS-PAGE) non-reduced (%) | 100 | 100 | 100 | 100 | 100 | 100 |
| % Purity (RP-HPLC) (%) | 85.9 | 86.2 | 85.9 | 86.0 | 85.9 | 86.1 |
| Potency (bioassay) | 90 | 109 | 90 | 105 | 90 | 107 |
| Relative potency (%) | | | | | | |
| Bioburden (X CFU/ml) | 0 | | | | | |
| Osmolality (mOsm/kg) | 306 | 310 | 306 | 309 | 306 | 309 |

Stability data for two lots of NEUG-2 in liquid form at 2-8° C. are shown below in Tables 10.1 and 10.2.

TABLE 10.1

Stability of liquid NEUG-2 (Lot 3029) 1.2 ml in polypropylene tubes

| Attributes | | 0 | 1 | 3 | 6 | 9 | 12 | 18 |
|---|---|---|---|---|---|---|---|---|
| Appearance | Visual inspection | CP | CP | CP | CP | CP | CP | CP |
| pH | | 6.0 | 6.0 | 6.0 | 6.1 | 6.0 | 6.0 | 6.1 |
| Osmolality (Freezing point) (mOsm/kg) | | 306 | 303 | 300 | 305 | 308 | 308 | 313 |
| Concentration (A280) (mg/mL) | | 57.5 | 58.7 | 57.6 | 58.5 | 58.3 | 57.7 | 57.3 |
| Purity (SDS-PAGE), Reduced (%) | | 100 | 99 | 100 | 100 | 100 | 100 | 100 |
| Purity (SDS-PAGE), Non-reduced (%) | | 100 | 100 | 100 | 100 | 100 | 100 | 100 |
| Purity (SE-HPLC) (%) | | 99.2 | 98.7 | 99.1 | 99.0 | 98.6 | 98.7 | 98.6 |
| Purity (RP-HPLC) | MP | 85.9 | 86.2 | 86.3 | 85.4 | 86.4 | 85.7 | 85.5 |
| | RRT 0.98 (%) | 11.8 | 11.5 | 11.3 | 11.6 | 11.5 | 11.5 | 11.3 |
| | MP + RRT 0.98 (%) | 97.7 | 97.6 | 97.6 | 96.6 | 97.7 | 96.8 | 96.8 |
| Purity (IE-HPLC) (%) | | 85.2 | 87.8 | 88.6 | 86.4 | 80.4 | 84.9 | 84.8 |
| Potency (bioassay) (relative potency %) | | 90 | 107 | 117 | 115 | 116 | 106 | 125 |
| Free Thiol (ellman's Assay) (mol/mol) | | NT | NT | 2.0 | 2.0 | 1.7 | 1.6 | 1.6 |

TABLE 10.2

Stability of liquid NEUG-2 (cGMP lot 071026004) 1.0 ml in teflon vial

| Attributes | | 0 | 3 | 6 | 9 | 12 | 18 |
|---|---|---|---|---|---|---|---|
| Appearance | Visual inspection | CPF | CPF | CPF | CPF | CPF | CPF |
| pH | | 6.0 | 6.1 | 6.0 | 6.0 | 6.0 | |
| Osmolality (Freezing point) (mOsm/kg) | | 313 | 312 | 334 | 3556 | 411 | 416 |
| Concentration (A280) (mg/mL) | | 62.0 | 61.3 | 63.7 | 67.5 | 74.9 | 80.6 |
| Purity (SDS-PAGE), Reduced (%) | | 100 | 100 | 100 | 100 | 100 | 100 |
| Purity (SDS-PAGE), Non-reduced (%) | | 100 | 100 | 100 | 100 | 100 | 100 |
| Purity (SE-HPLC) (%) | | 98.1 | 97.9 | 98.1 | 98.0 | 97.9 | 97.7 |
| Purity (RP-HPLC) | MP | 87.5 | 87.3 | 87.2 | 87.3 | 86.2 | 85.6 |
| | P-1 (%) | 10.0 | 10.3 | 10.2 | 9.7 | 10.0 | 10.4 |
| | MP + P-1 (%) | 97.5 | 97.6 | 97.5 | 97.0 | 96.2 | 96.0 |
| Purity (IE-HPLC) (%) | | 89.5 | 86.8 | 82.2 | 85.4 | 84.9 | 85.0 |
| Potency (bioassay) (relative potency %) | | 87 | 84 | 115 | 108 | 112 | 80.3 |
| Free Thiol (Ellman's Assay) | | NT | 2.0 | 1.9 | 2.0 | 1.7 | 1.5 |

As described above, changes to the formulation were made from the NEUG-1 process to the NEUG-2 process. These changes were made to ensure product quality at a higher NEUG concentration and did not include any new excipients. Primary changes were an increase in the ionic strength (from 10 to 20 mM) and a reduction in the pH (from 7.2 to 6.0). The BDS formulation has been improved from the NEUG-1 to NEUG-2 process to reduce concentration dependent aggregation. It is thus expected that the NEUG-2 formulation will demonstrate improved stability relative to the already robust NEUG-1.

In addition, there were no significant effects of tungsten on NEUG-2 after three month stability studies either in lyophilized for or in liquid form at recommended storage condition as at 2-8° C. (analysis via SE-HPLC, RP-HPLC and potency; data not shown).

Example 9

Description and Composition of Exemplary Drug Product: NEUG-2

1. Description of Dosage Form

In one embodiment, Neugranin™ ("NEUG") is supplied as a sterile, lyophilized formulation in single-use Type 1 glass vials, which are sealed with a coated rubber stopper and a flip-off seal. NEUG can be stored at 2-8° C. Upon reconstitution with 1.0 mL of Sterile Water for Injection (WFI), each vial contains 50 mg/mL (50 mg/vial deliverable) NEUG in 20 mM sodium phosphate, 180 mM mannitol, 60 mM trehalose dihydrate, 0.01% (w/v) polysorbate 80, pH 6.0. After reconstitution the vial can be held at room temperature and should be used within 8 hours.

2. Quantitative Composition

The quantitative composition of one exemplary NEUG drug product (NEUG-2) is provided in Table 11, below. Note that the liquid form of NEUG-2 has the same quantitative composition as the lyophilized form. The liquid form can be provided in a prefilled syringe (see section 9, below).

TABLE 11

Quantitative composition of NEUG-2 drug product

| Ingredient | Concentration | Amount deliverable per vial[a] | Grade | Purpose |
|---|---|---|---|---|
| Neugranin | 50.0 mg/mL | 50.0 mg | | API |
| Sodium Phosphate monobasic | 2.42 mg/mL (17.4 mM) | 2.42 mg | USP, multi-compendial | Buffering agent |
| Sodium Phosphate dibasic | 0.35 mg/mL (2.5 mM) | 0.35 mg | USP, multi-compendial | Buffering agent |
| Mannitol | 32.79 mg/mL (180 mM) | 32.79 mg | USP, multi-compendial | Bulking agent |
| Trehalose dihydrate | 22.70 mg/mL (60 mM) | 22.70 mg | High Purity | Cryoprotectant |
| Poly-sorbate 80 | 0.1 mg/mL (0.01%) | 0.1 mg | USP, multi-compendial | Inhibit aggregation and adsorption |
| Sterile WFI | reconstitute with 1.0 mL | 1.0 mL | USP | Diluent |

[a] A 0.11 ml overage is filled into each vial to assure the 1.0 ml deliverable volume.

3. Reconstitution Buffer

Sterile Water For Injection (WFI) can be used for reconstitution of NEUG in lyophilized form.

4. Excipients

The composition of the exemplary NEUG formulation is 2.77 mg/mL sodium phosphate, 33.79 mg/mL mannitol, 22.7 mg/mL trehalose dihydrate, and 0.1 mg/mL polysorbate 80, pH 6.0 (see Table 5 above). The sodium phosphate is a buffering agent, mannitol is used as a bulking agent to provide good cake structure and to adjust tonicity, trehalose is used as a cryoprotectant, and polysorbate 80 is used to reduce the potential for aggregation and adsorption. At the concentration of active pharmaceutical ingredient ("API") in NEUG-2 of 50 mg/mL, the protein itself acts as a robust buffer. Compendial excipients used for the formulation comply with multiple-compendia (MC). The exception is trehalose dihydrate for which no compendia is currently available; however, it complies with a rigorous non-compendial set of specifications. Trehalose is GRAS listed at the US FDA and is used in the formulation of numerous commercial parenteral pharmaceuticals (for example, bevacizumab (Avastin) and trastuzumab (Herceptin)).

5. Formulation Development

The initial formulation used for toxicology studies was designed to support storage as a frozen liquid at −20° C. (NEUG-0). To improve the robustness of the formulation for shipping and storage at clinical sites, as well as to provide a stable product with an expected long shelf life, a lyophilized form has been used for all clinical material to date. The initial clinical material (NEUG-1) has proven quite stable, with a current shelf-life of 2 years, which will likely be further extended. Subsequent formulation development demonstrated that higher ionic strength and lower pH further stabilized the API at higher concentration (>25 mg/mL). To this end, one formulation (NEUG-2) has a lower pH (6.0 vs 7.2) and higher phosphate concentration (20 vs. 10 mM). Forced degradation studies demonstrate that this formulation protects the drug substance in the liquid state from vigorous shaking, repeated freeze-thawing, and concentration induced aggregation. The identical freeze dry cycle as described for NEUG-1 was used for the NEUG-2 formulation; both produced well-formed cakes.

6. Manufacturing Process Development

In some embodiments, NEUG final drug product is generated by diluting bulk drug substance with formulation buffer to the desired concentration (50 mg/mL), filling, and then freeze drying the product.

To support comparability between the toxicology and clinical material, a lot of final drug product ("FDP") from both processes (NEUG-1 and NEUG-2) was characterized physicochemically.

The results of the physicochemical comparability study are included in Table 12 below, and demonstrate that the quality of the NEUG-2 product is at least as good, if not better, than the NEUG-1 product. The freeze-drying process does not have any adverse product impact.

TABLE 12

Comparison of NEUG-1 and NEUG-2

| Attribute | Analytical Method | FDP Lot B060928DP (NEUG-1) | FDP Lot 3029DP (NEUG-2) |
|---|---|---|---|
| Appearance | Visual inspection | White cake | White cake |
| Reconstitution Time | Visual inspection | 20 sec | 29 sec |
| Appearance-post-recon | Visual inspection | Clear, pale yellow solution | Clear, pale yellow solution |
| pH | pH Electrode | 7.3 | 6.0 |
| Osmolality | Freezing point | 329 mOsm/kg | 293 mOsm/kg |
| Protein concentration | Absorbance at 280 nm | 16.1 mg/mL | 47.7 mg/mL |
| Purity | SDS-PAGE: Reduced and non-reduced with Coomassie Blue Stain | R: 100% NR: 100% | R: 100% NR: 100% |
| Purity | SDS-PAGE: Reduced and non-reduced with Silver stain | Comparable to Reference Standard | Comparable to Reference Standard |
| Purity | SEC-HPLC | 97.6% | 98.8% |
| Purity | RP-HPLC | 86.5% | 87.6% |
| Charge Herterogeneity | IEC-HPLC | 77.1% | 88.0% |
| Potency | Cell Proliferation | 134% | 95.2% |
| Residual Moisture | Karl Fischer | 0.4% | 0.2% |

The NEUG used for initial clinical studies (NEUG-1) is physicochemically comparable to the currently formulated NEUG (NEUG-2). The changes made to the manufacturing process and dosage form did not have an impact on clinical efficacy or safety (data not shown).

7. Batch Analysis

FIG. 20 summarizes the results of analysis performed on a representative, development lot of NEUG-2 final drug product. In the table, "ND" means the test was "not done" for development lots.

8. Stability of Final Drug Product

A stability study for a lot of the final drug product of NEUG-2 was initiated. At the one month time point, no significant changes were observed for any samples. (Data not shown). Stability conditions were as follows: NEUG-2 development lot at 50.0 mg/ml NEUG in PMTT10/6.0; 1.2 mls liquid in a 3 ml glass vial; storage at 2-8° C., 25° C./60% RH, or 40° C./75% RH.

9. Studies of NEUG-2 Liquid in Prefilled Syringes

To assess the feasibility of providing NEUG-2 (PMTT, pH 6.0) as a liquid in a prefilled syringe for commercial products, the following studies were performed.

It is known that the some syringes (e.g., from Becton Dickinson) contain two major excipients, tungsten and silicone, which might interact with the product and/or the buffer. To evaluate the interactions between the syringe excipients and the product, several studies were carried out including a silicone oil migration study, silicone-spiked-in and tungsten-spiked-in studies, as well as the long-term stability studies of the prefilled syringes. The methods used to assess the stability of CG10639 (NEUG-2) in a liquid state included visual inspection, SE-HPLC, RP-HPLC, IE-HPLC, Bioassay, etc.

To summarize the results, no significant changes were found in the samples spiked with five forms of tungsten (sodium tungsten dehydrate, sodium polytungstate, ammonium tungstate, WO3 and WO2) at three different doses (500, 1000 and 2500 ppb) and kept at either 2-8° C. or 25° C. over three months. Samples were analyzed via SE-HPLC, RP-HPLC, and bioassay (data not shown).

In the silicone compatibility study, there were no effects of silicone on the product quality observed when samples were in syringes coated with two different doses of silicone (0.4 mg or 0.8 mg) and kept at 2-8° C. for 4 weeks, or samples were spiked in with two different doses of silicone and kept at 2-8° C. for three months (data not shown). The silicone oil distribution in both formulation buffer and drug product solution were compatible and remained essentially even (data not shown). There were no gliding force changes on prefilled syringes after two months' storage (data not shown). Moreover, CG10639 appeared to be insensitive to agitation and needle-shear (data not shown).

The long-term stability studies for at least up to nine months demonstrate that liquid NEUG-2 is stable in the prefilled syringe at 2-8° C., is stable for at least up to 18 months at 4° C., and is compatible with the materials of product contact. Data for the long term stability of liquid NEUG-2 in prefilled syringes is shown in Table 13, below.

TABLE 13

Stability of liquid NEUG-2 in prefilled syringes 2-8° C.

| Attributes | | 0 | 1 | 2 | 3 | 6 | 9 |
|---|---|---|---|---|---|---|---|
| Appearance | Visual inspection | CPF | CPF | CPF | CPF | CPF | CPF |
| | Weight Check (g) | 1.0234 | 1.0233 | 1.0262 | 1.0243 | 1.028 | 1.027 |
| pH | | 6.0 | 6.0 | 6.0 | 6.1 | 6.0 | 6.0 |
| Osmolality (Freezing point) (mOsm/kg) | | 309 | 312 | 311 | 308 | 309 | 311 |
| Concentration (A280) (mg/mL) | | 50.5 | 50.5 | 50.4 | 50.5 | 50.8 | 50.6 |
| Purity (SDS-PAGE), Reduced (%) | | 100 | 99 | 100 | 100 | 100 | 100 |
| Purity (SDS-PAGE), Non-reduced (%) | | 100 | 100 | 100 | 100 | 100 | 100 |
| Purity (SE-HPLC) (%) | | 98.7 | 98.6 | 98.7 | 99.1 | 98.5 | 98.6 |
| Purity (RP-HPLC) | RRT0.98 (DMF) (%) | 11.1 | 11.3 | 11.0 | 10.5 | 11.3 | 11.4 |
| | Total (%) | 96.4 | 97.9 | 97.0 | 97.2 | 96.0 | 97.1 |
| Purity (IE-HPLC) (%) | | 84.7 | 87.3 | 83.2 | 86.8 | 87.7 | 87.2 |
| Potency (bioassay) (relative potency %) | | 109 | 109 | 89.7 | 107 | 85.8 | 90.6 |

Time (months) spans columns 0–9.

CPF = clear, pale yellow, essentially free from foreign particulate matter

Based on these studies, there are no significant interactions between tungsten or silicone and the NEUG product with PMTT formulation (20 mM Phosphate, 180 mM Mannitol, 60 mM Trehalose Dihydrate, 0.01% (W/V) Polysorbate 80, pH 6.0).

Clinical Evaluation of NEUG in Human Patients

The following examples are provided in two main sections entitled "Phase I" and "Phase II." Each phase includes two parts, Part A and Part B. The Phase I and Phase II examples are summarized in Table 14 below. Note that NEUG-1 was tested in Phase I, and NEUG-2 was tested in Phase II.

TABLE 14

Summary of human clinical NEUG studies

| Trial | (Part)/Tumor Type | Objective | Chemo. | No. of Subjects | Treatment Arms |
|---|---|---|---|---|---|
| Phase I | (A)/breast | Initial dose-finding in absence of chemotherapy | none | 13 | 50, 150, 300, 450 µg/kg NEUG |
|  | (B)/breast | Initial dose-finding in presence of chemotherapy | Doxorubicin Docetaxel 2 Cycles | 51 | 300 or 450 µg/kg NEUG vs. 6 mg pegfilgrastim |
| Phase II | (A)/breast | Dose-finding for fixed doses of Neugranin | Doxorubicin Docetaxel 4 Cycles | 78 | 30, 40, 50 mg NEUG vs. 6 mg pegfilgrastim |
|  | (B)/breast | Demonstration of non-inferiority of NEUG vs pegfilgrastim | Doxorubicin Docetaxel 4 Cycles | 256 | 40 and 50 mg NEUG vs. 6 mg pegfilgrastim |

Each Phase is divided into five sections: 1) objectives, 2) patient characteristics, 3) study agent, 4) study characteristics, and 5) results of Parts A and B.

Example 10

Phase I

1. Objective

The Phase IA/B, IIA/B study was performed to evaluate the safety, tolerability, immunogenicity, pharmacokinetics and pharmacodynamics of subcutaneously administered Neugranin™ ("NEUG") (recombinant human albumin-human granulocyte colony stimulating factor) in subjects receiving myelosuppressive chemotherapy (doxorubicin/docetaxel).

For Phase I, the primary study objectives were to assess the safety profile of NEUG given subcutaneously over a range of potential therapeutic doses compared to pegfilgrastim by measuring the frequency, severity, and duration of treatment-emergent adverse events and correlating them with the time and dose of NEUG administration.

Secondary study objectives were to assess the pharmacokinetics and immunogenicity of NEUG, and to compare the effect of NEUG administration on the incidence, severity and duration of neutropenia to pegfilgrastim in patients receiving doxorubicin/docetaxel.

Phase I was performed as two parts, Part A and Part B as noted in Table 2 above.

2. Patient Characteristics

For Phase I, patients were screened based on the following characteristics or parameters:

Inclusion:
1. Patients with histologically-confirmed breast cancer scheduled to receive doxorubicin and docetaxel.
2. 18 years of age or older.
3. Adequate hematologic function.
4. ANC>1500/mm$^3$
5. Platelets>100,000/mm$^3$
6. Adequate hepatic and renal function:
7. Serum creatinine<2.0×upper limit normal
8. Total bilirubin within normal limits (WNL) for local laboratory
9. Serum transaminases (SGOT/SGPT)<1.5×upper limit normal
10. Alkaline phosphatase<2.5×upper limit normal
11. ECOG performance status 0 or 1.
12. Eligible to receive doxorubicin based on a left ventricular ejection fraction (LVEF) within normal limits.
13. Have the ability to understand the requirements of the study, provide written informed consent (including consent for use and disclosure of research-related health information) and comply with the study protocol procedures.

Exclusion:
1. More than 1 prior chemotherapy regimen (including adjuvant therapy if given within the last 12 months); any chemotherapy/immunotherapy within 4 weeks prior to study entry; cumulative anthracycline dose that would preclude 2 full-dose cycles of doxorubicin in this study.
2. Prior use of any nitrosoureas (BCNU, CCNU) or mitomycin-C within 6 weeks of study chemotherapy.
3. Cardiac history, signs or symptoms that, in the Investigator's opinion, preclude the use of an anthracycline-based chemotherapy regimen.
4. Prior surgery or radiation therapy within 2 weeks of study chemotherapy.
5. Prior wide field irradiation to the pelvis or to greater than 20% of the marrow-bearing areas, or bone marrow involvement.
6. Prior high-dose chemotherapy with hematopoietic stem cell transplant.
7. Prior use of myeloid (G-CSF or GM-CSF) growth factors within 4 weeks of study chemotherapy.
8. Prior use of erythropoietin within 4 weeks of study chemotherapy.
9. History of myeloid malignancy or myelodysplasia.
10. Known brain metastases unless adequately treated (surgery or radiotherapy), no evidence of progression with a minimum of 3 weeks observation and neurologically stable off anticonvulsants and steroids.
11. Known sickle cell disease.

12. Diagnosis of adult respiratory distress syndrome (ARDS).
13. Current infection requiring intravenous or oral antibiotics.
14. Known history of allergies to yeast-derived products.
15. Known hypersensitivity to *E coli*-derived proteins, pegfilgrastim, filgrastim, or any other component of pegfilgrastim (phase 2 only).
16. Pregnant female or nursing mother (over the course of the study, all females must practice a method of contraception with greater than 90% reliability, or be sterile or postmenopausal).
17. Known HIV positive or active hepatitis (patients with unknown status will not be tested).
18. Males who do not agree to use effective contraception throughout the study and for a period of 30 days after the last dose of study agent.

Subjects were removed from further treatment for the following reasons:
1. Disease progression
2. Unacceptable toxicities despite optimal treatment
3. Intercurrent illness at the investigator's discretion
4. Doxorubicin regimen—Maximum lifetime permissible cumulative dose reached (see eligibility criteria)
5. Withdrawal of consent
6. Non-compliance/Loss to follow-up
7. Pregnancy If treatment with NEUG was stopped, subjects remained on study and were followed at least 30 days following the final dose of any study drug for scheduled safety and PK assessments.

3. Study Agent

NEUG (recombinant human albumin-human granulocyte colony stimulating factor, rHSA-G-CSF), is a fusion protein with a molecular mass of approximately 85 kDa connected in a single chain comprising residues 1-585 corresponding to the mature form of HSA and residues 586-759 corresponding to the mature form of human G-CSF. The therapeutic moiety of NEUG is recombinant human DNA-derived G-CSF.

NEUG was supplied as a sterile, lyophilized formulation in single-use Type 1 glass vials and stored at 2-8° C. Upon reconstitution with 1.1 ml of sterile water for injection, each vial contained 15 mg/ml (15 mg/vial deliverable) NEUG in 10 mM sodium phosphate, 200 mM mannitol, 60 mM trehalose dehydrate, 0.01% (w/v) polysorbate 80, pH 7.2.

The composition of the NEUG drug product used in Phase I is presented in Table 1.

Commercially available Neulasta® (pegfilgrastim) was supplied in 0.6 ml prefilled syringes for subcutaneous injection. Each syringe contains 6 mg pegfilgrastim (based on protein weight), in a sterile, clear, colorless, preservative-free solution (pH 4.0) containing acetate (0.35 mg), sorbitol (30.0 mg), polysorbate 20 (0.02 mg), sodium (0.102 mg) in water for injection. USP.

NEUG (50, 150, 300 or 450 µg) or Neulasta® (pegfilgrastim) (6 mg) was administered by subcutaneous administration.

4. Study Characteristics a. Study Schedule and Duration

This study was a first-in-man, multi-center, open-label non-controlled sequential dose escalation of a followed by a controlled, randomized trial conducted in 62 subjects with breast cancer scheduled to receive doxorubicin/docetaxel. The study consisted of 2 parts. Part A was a sequential dose escalation in 13 subjects, 4 dose cohorts (50, 150, 300, or 450 µg/kg) with 3 subjects in each of the 50, 150 and 450 µg/kg cohorts and 4 subjects in the 300 µg/kg cohort, to evaluate safety prior to the randomized, Part B of the trial.

In Part A, subjects received the first dose of NEUG at least 2 weeks prior to the start of chemotherapy (cycle 0) for an initial assessment of safety and effects on absolute neutrophil count ("ANC") in the absence of cytotoxic chemotherapy. After a minimum of 2 weeks follow-up, subjects received NEUG at the same dose following chemotherapy in cycles 1 and 2 if there were no dose-limiting adverse events considered related to NEUG in cycle 0 and the subject continued to meet all eligibility criteria.

In Part A, dose limiting toxicity (DLT) was defined as grade 2 or greater clinically significant adverse event(s) considered possibly, probably or definitely related to the study agent with the exception of grade 2 bone pain. Within each Part A cohort, the initial study drug administration to each subject entering the trial was separated by a minimum of 24 hours to monitor for acute adverse events.

The decision to escalate to the next dose level was based upon the review of the safety data for at least 7 days after the first dose administration of NEUG for all subjects in a given cohort. If none of the 3 subjects experienced a DLT, dose escalation continued with the enrollment of 3 subjects at the next dose level. If 1 of 3 subjects in a given cohort exhibited evidence of a DLT, another 3 subjects were recruited at that dose level for a total of 6 subjects per cohort. Dose escalation continued to occur if only 1 of 6 subjects experienced a DLT. If 2 of 6 subjects develop a DLT, dose escalation stopped and no further NEUG treatments were administered.

The remaining subjects completed their scheduled safety, pharmacokinetic and pharmacodynamic evaluations.

Following demonstration of safety in the initial Part A cohorts, Part B was performed. In Part B, subjects were randomized in a parallel fashion to 1 of 3 treatment groups: NEUG 300 µg/kg (n=20), NEUG 450 µg/kg (n=21), or pegfilgrastim (n=10) at the approved dose of 6 mg administered approximately 24 hours after study chemotherapy.

Figure 26:
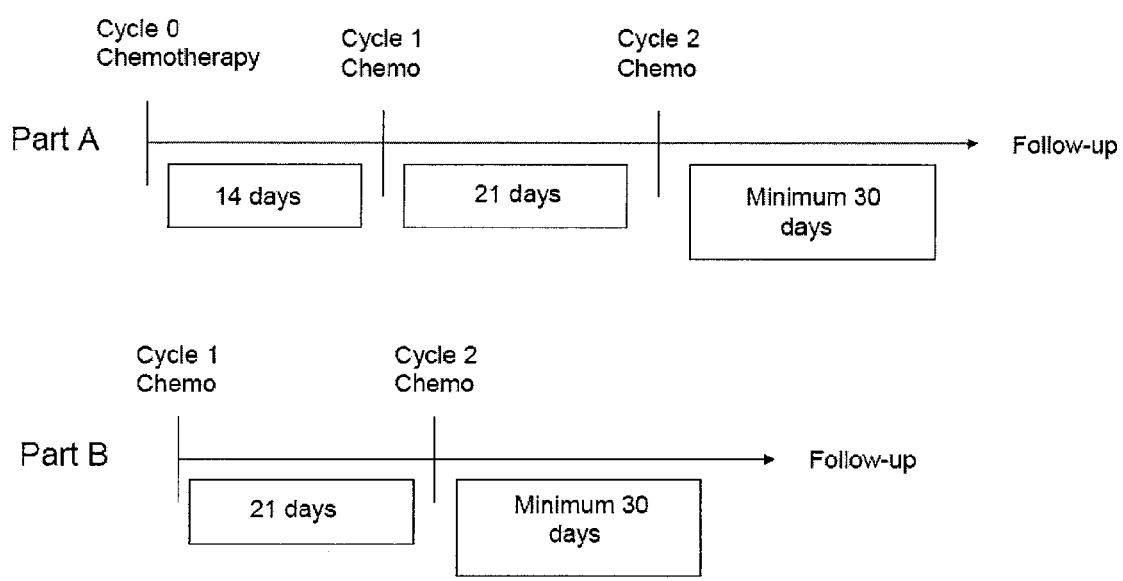
FIG. 26 illustrates the chemotherapy cycles for the Phase I studies.

Tables 15 and 16 below summarize the disposition of the subjects in Phase I, Parts A and B. FIG. 26 shows the chemotherapy cycles for Phase I study, Parts A and B.

TABLE 15

Disposition of Subjects in Phase I

| | Dose | N (NEUG/pegfilgrastim) |
|---|---|---|
| Part A | | |
| Sequential Dose Escalation | NEUG 50 µg/kg | 3/0 |
| | NEUG 150 µg/kg | 3/0 |
| | NEUG 300 µg/kg | 4/0 |
| | NEUG 450 µg/kg | 3/0 |
| Part B | | |
| Parallel Randomization | NEUG 300 µg/kg | 20/5 |
| | NEUG 450 µg/kg | 21/5 |

TABLE 16

| Disposition of Subjects in Phase I | | | |
|---|---|---|---|
| Treatment | Part A (N) | Part B (N) | Total |
| Neulasta ® (pegfilgrastim) | 0 | 10 | 10 |
| NEUG 50 | 3 | 0 | 3 |
| NEUG 150 | 3 | 0 | 3 |
| NEUG 300 | 4 | 20 | 23 |
| NEUG 450 | 3 | 21 | 24 |
| Total | 13 | 51 | 64 | b. Concomitant Therapy During Phase I, Parts A and B
Chemotherapy

The chemotherapy regimen for this trial consisted of doxorubicin 50 mg/m$^2$ and docetaxel 75 mg/m$^2$ administered sequentially by intravenous infusion on day 1 of treatment for up to two 21-day cycles.

Prior to receiving each cycle of therapy, subjects had to have an absolute neutrophil count (ANC)>1.5×10$^9$/L and platelets>100×10$^9$/L. Treatment could be delayed up to two weeks for hematologic recovery.

The combination of doxorubicin and docetaxel has been reported to have significant clinical activity in patients with breast cancer. However, the combination is highly myelosuppressive with higher rates of grade 3 or 4 neutropenia than other standard regimens.

Even with the addition of CSFs, the combination of doxorubicin and docetaxel has induced grade 4 neutropenia in 79% of patients and febrile neutropenia rates of 9-18%. This doxorubicin/docetaxel regimen has been used in studies of new agents to prevent neutropenia and its complications. Therefore, the combination of doxorubicin and docetaxel is an appropriate chemotherapy regimen to study the potential of a new agent like NEUG.

Doxorubicin
Pharmacologic Data

Doxorubicin hydrochloride is an anthracycline antibiotic obtained from *streptomyces peucetius* var *caesius* which inhibits DNA and DNA-dependent RNA synthesis, as well as protein synthesis. Doxorubicin is active in all phases of the cell cycle but maximally cytotoxic in S phase. Excretion of the drug is predominately by the liver; renal clearance is minor.

Pharmaceutical Data

The drug is marketed commercially in 10, 20 50, 100 or 200 mg vials. Lyophilized preparations may be reconstituted with sterile water for injection, dextrose 5% solution, or 0.9% saline for injection.

Side Effects and Toxicity

Myelosuppression, primarily leukopenia, with a nadir of approximately 10-14 days, and cardiotoxicity, including a rare, acute pericarditis-myocarditis syndrome and a delayed, cumulative dose related cardiomyopathy are the dose-limiting toxicities of doxorubicin. Marked alopecia and moderate nausea/vomiting are expected toxicities. Extravasation reactions producing local skin and tissue damage at the site of inadvertent extravasation, stomatitis, hyperpigmentation of the skin (particularly the nailbeds), and a "recall" phenomenon at sites of previous irradiation have been reported.

Docetaxel
Pharmacologic Data

Docetaxel is a semisynthetic taxoid that binds to free tubulin and promotes assembly of stable microtubules, interfering with mitosis and cell replication (cell cycle specific for M phase). Docetaxel is extensively protein-bound, extensively metabolized in the liver, with fecal excretion of approximately 75% of the dose within 7 days.

Pharmaceutical Data

Docetaxel (Taxotere™, Sanofi Aventis) is provided in 80 mg/2 mL or 20 mg/0.5 ml single-dose vials with an accompanying diluent (13% ethanol in Water for Injection) vial. Each ml of Taxotere contains 40 mg of docetaxel (anhydrous) and 1080 mg polysorbate 80.

Side Effects and Toxicity

Docetaxel should not be given to patients who have a history of severe hypersensitivity reactions to docetaxel or other drugs formulated with polysorbate 80 such as etoposide and vitamin E.

Patients who experience severe hypersensitivity reactions should not be rechallenged. Patients receiving docetaxel should be premedicated with corticosteroids as outlined below.

Mild to moderate liver impairment results in delayed metabolism by 27% and a 38% increase in systemic exposure (AUC). Docetaxel should not be given to patients with SGOT and/or SGPT>1.5 times normal limits and alkaline phosphatase>2.5 times normal limits. Fluid retention occurred in 17% (moderate) and 6% (severe retention) of patients in Phase III studies despite corticosteroid premedication. Severe neurosensory symptoms (paresthesia, dyesthesia, pain) have been observed.

Expected side effects include myelosuppression, primarily leukopenia, with a nadir of approximately 9 days with recovery by day 15-21. Alopecia, nail and cutaneous changes, stomatitis, myalgia/arthralgia, nausea/vomiting, and hypotension have been reported.

Chemotherapy Dosage, Administration and Dose Modifications

On day 1 of each treatment cycle, chemotherapy (doxorubicin followed by docetaxel) was administered.

Doxorubicin was administered at a dose of 50 mg/m$^2$ by IV bolus through the side arm of an infusing intravenous line or central venous catheter to avoid extravasation injury.

Docetaxel 75 mg/m$^2$ was diluted in 250 mL 0.9% saline or 5% dextrose solution and administered intravenously over approximately 1 hour via a polyethylene-lined infusion set. Vital signs were obtained immediately prior to and after the end of the docetaxel infusion.

Prior to receiving each cycle of therapy, subjects had to have an absolute neutrophil count (ANC)>1500/mm$^3$ and platelets>100,000/mm$^3$. Treatment could be delayed up to two weeks for hematologic recovery. A 25% dose reduction of chemotherapy doses was allowed for grade 3-4 non-hematologic toxicities, two grade 3-4 infectious episodes, or grade 4 thrombocytopenia.

Subjects experiencing severe hypersensitivity reactions or non-hematologic toxicities that preclude further cycles of chemotherapy were removed from study treatment but completed follow-up.

Chemotherapy Pre-Medication

Oral (IV as needed) corticosteroids (such as dexamethasone 8 mg BID) were administered for three days starting 1 day prior to docetaxel administration in order to reduce the incidence and severity of fluid retention and hypersensitivity reactions.

The use and selection of anti-emetic agents or other pre-medications (e.g. H$_2$ antagonists) was left to the discretion of the treating physician.

Prohibited Medications

Subjects should not have received any of the following medications and or procedures during this study and for the additional times specified below:

1. Other investigational agents within 30 days of initiating study agent and for the duration of the trial.
2. Subsequent cycles of chemotherapy should not be initiated until 14 days following dosing with NEUG.
3. Cytokines, other hematopoietic growth factors and prophylactic antibiotics for the duration of the trial unless prolonged or febrile neutropenia occurs. If the subject was treated with G-CSF at any time between the screening period and Day 0 they were not eligible to receive NEUG and were discontinued from the study.

Allowed Medications

Subjects were allowed to continue their baseline medications(s). The daily dose of each medication was maintained throughout the study if possible. If for any reason deemed necessary by the investigator, a subject required additional medication(s) or change of dose, the medication(s), route of administration, and the indication for which it was given was recorded on the appropriate pages of the CRF.

Antibiotics

All subjects received prophylactic oral antibiotics (e.g. ciprofloxacin) following each course of chemotherapy to reduce the likelihood of infection. If febrile neutropenia or persistent severe neutropenia (ANC<$0.5 \times 10^9$/L for ≥5 days) occurred, the subject was considered a treatment failure, removed from the study, completed study follow-up and received all standard supportive care, including growth factor support at the Investigator's discretion.

Subjects who experienced severe hypersensitivity reactions or non-hematologic toxicities that precluded further cycles of chemotherapy were also removed from study treatment and completed follow-up.

c. Safety Assessments

The safety of NEUG was assessed by evaluation of the type, frequency, and severity of adverse events ("AEs"), changes in clinical laboratory tests (hematology and clinical chemistry), immunogenicity, physical examinations, and the monitoring of vital signs over time. All AEs and laboratory toxicities were graded based on the National Cancer Institute Common Terminology Criteria for Adverse Events (NCI-CTCAE Version 3.0, 12 Dec. 2003). Adverse events (to include serious adverse events, "SAEs") were captured from the start of study drug administration through 30 days following the final dose of any study drug. Laboratory assessments were obtained as outlined in the Schedule of Assessments. In the event of any Grade 4 neutropenia toxicity, labs were obtained every day until ANC>500. If the subject's next cycle of therapy was delayed (and after the last cycle of treatment), complete blood count (CBC) with differential was obtained at least twice weekly until ANC>1500.

5. Results of Phase I, Parts A and B a. General

Statistical Methods:

The data related to safety, pharmacokinetics (PK), pharmacodynamics (PD) and immunogenicity parameters were analyzed using descriptive statistical methods.

For frequency and severity of adverse events, and for laboratory toxicity grading, counts and rates are presented.

Efficacy analyses included the incidence and duration of grade 4 and grade 3-4 neutropenia, nadir ANC, time to nadir ANC, time to recovery (to ANC>$0.5 \times 10^9$/L and ANC>$1.0 \times 10^9$/L) and the incidence of febrile neutropenia.

No strict statistical power requirement was used to select the sample size for this study. A study with a power of 80% to demonstrate non-inferiority of NEUG to pegfilgrastim at a significance level of 5% was calculated to require approximately 37 subjects per treatment arm. As this was a phase 1/2a study conducted primarily for safety, it was determined that the required sample size to be powered for effect was larger than appropriate. As such, efficacy trends were evaluated.

Disposition/Demographics:

A total of 13 subjects were enrolled in the Part A, sequential dose escalation portion of the trial. A total of 51 subjects were enrolled in the Part B portion, and randomized to NEUG 300 µg/kg (n=20), NEUG 450 µg/kg (N=21), or pegfilgrastim 6 mg (n=10).

b. Study Results

Figure 23:
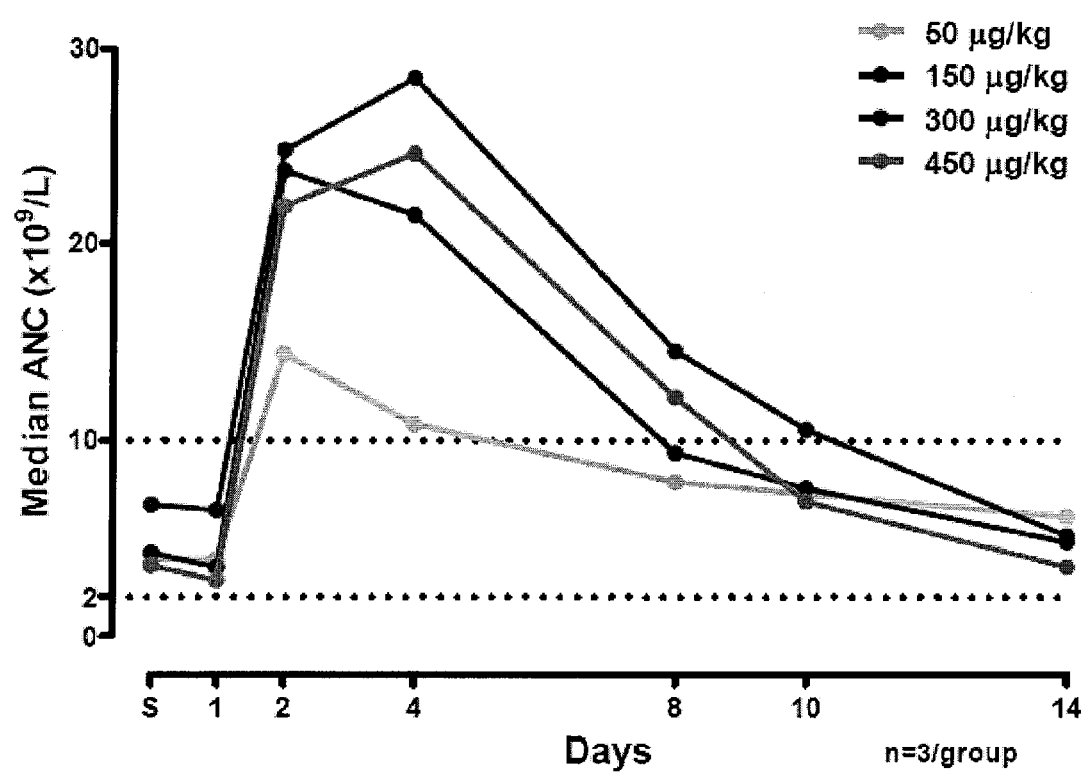
FIG. 23 is a graph showing the median absolute neutrophil count (ANC) for subjects receiving NEUG-1 before chemotherapy (Cycle 0) from treatment to day 14. At day 4, the lines from highest to lowest are: 300 μg/kg NEUG, 450 μg/kg NEUG 150 μg/kg and 50 μg/kg NEUG.

In initial dose-finding, in the absence of chemotherapy, NEUG was well tolerated and resulted in the expected rise in ANC, which peaked between days 2 and 4 and returned to normal by day 14 (FIG. 23).

In Part A, all three subjects in the 50 µg/kg NEUG dose group and 1 subject in the 450 µg/kg Neugranin dose group experienced febrile neutropenia or severe neutropenia lasting greater than 5 days. In Part B, one subject in the 300 pg/kg NEUG dose group and 2 subject in the 450 µg/kg NEUG dose group experienced febrile neutropenia or severe neutropenia lasting greater than 5 days. One subject in the pegfilgrastim group experienced febrile neutropenia or severe neutropenia lasting greater than 5 days.

c. Immunogenicity

Serum samples for antibodies to NEUG were obtained prior to dosing on Day 1 of every NEUG cycle and at the end of treatment visit (at least 15 days after the last dose) in subjects receiving NEUG. If at any time during the study a subject developed a positive anti-NEUG antibody response, a repeat sample was obtained approximately 6 months after the final NEUG dose.

Testing was completed on all subjects through the end of treatment for both Part A and B. All samples were negative for antibodies to NEUG.

d. Adverse Events

During Part A, dose-limiting toxicity (DLT) was defined as grade 2 or greater clinically significant adverse event(s), considered possibly, probably or definitely related to the study agent with the exception of grade 2 medullary bone pain. No DLT was encountered in cycle 0 in any of the Part A cohorts. Only 2 adverse event were reported as related to NEUG administration: bone pain and exacerbation of pre-existing hypertension, the latter occurring 7 days after NEUG administration. Both events resolved without sequeale.

Thirty one of the 41 NEUG-treated subjects experienced at least 1 adverse event. The incidence of AEs among NEUG- and pegfilgrastim-treated subjects was comparable (75.6% and 70% respectively).

A summary of commonly reported adverse events (AEs greater than or equal to 5% of all subjects) for Part B is provided in Table 17.

TABLE 17

Summary of Treatment-Emergent Adverse Events in the Phase 1, Part B Population

| Med DRA Preferred Term | NEUG 300 (N = 20) | NEUG 450 (N = 21) | Pegfilgrastim (N = 10) |
|---|---|---|---|
| Related AE[1]: | | | |
| Bone Pain | 1 (4.5%) | 3 (14.3%) | 0 (0%) |
| Unrelated AE[2]: | | | |
| Nausea | 3 (15%) | 3 (14.3%) | 3 (30%) |
| Vomiting | 1 (5%) | 3 (14.3%) | 3 (30%) |
| Diarrhea | 1 (5%) | 1 (4.8%) | 1 (10%) |
| Stomatitis | 0 (0%) | 3 (14.3%) | 0 (0%) |
| Fatigue | 0 (0%) | 0 (0%) | 1 (10%) |

TABLE 17-continued

Summary of Treatment-Emergent Adverse Events
in the Phase 1, Part B Population

| Med DRA Preferred Term | NEUG 300 (N = 20) | NEUG 450 (N = 21) | Pegfilgrastim (N = 10) |
|---|---|---|---|
| Pharyngitis | 2 (10%) | 0 (0%) | 1 (10%) |
| Alopecia | 4 (20%) | 7 (33%) | 2 (20%) |
| Thrombocytopenia | 0 (0%) | 0 (0%) | 1 (10%) |
| Headache | 0 (0%) | 1 (4.8%) | 1 (10%) |
| Hypokalaemia | 0 (0%) | 2 (10%) | 1 (10%) |
| Vitamin D Deficiency | 3 (15%) | 0 (0%) | 1 (10%) |
| Hypertension | 0 (0%) | 1 (4.8%) | 1 (10%) |

[1]Related = considered possibly, probably or definitely related
[2]Unrelated = considered probably not related or not related The most commonly reported adverse event considered related to NEUG was bone pain, a typical adverse reaction associated with all G-CSF products, which was reported in 5 patients 4 listed in the table above, plus one Part A subject receiving 450 µg/kg). In all cases, the bone pain was NCI-CTCAE grade 1-2 in intensity, transient in duration and resolved without sequelae. Grade 1 elevations in alkaline phosphatase and uric acid occurred following administration of NEUG in Cycle 0; these events were deemed to be not clinically significant by the Investigators and resolved without intervention. These are expected effects in patients receiving a G-CSF (e.g., Neulasta®).

Other commonly reported adverse events during chemotherapy cycles (nausea, vomiting, alopecia, stomatitis) were consistent with anticipated adverse events in patients receiving the doxorubicin/docetaxel regimen.

The majority of reported AEs were of NCI CTC Grade 1 or 2 severity. Four AEs were reported as serious adverse events. Two subjects, one receiving 150 µg/kg and one 450 µg/kg, experienced vomiting that caused hospitalization and one of these subjects experienced a second SAE in the following chemotherapy cycle; vomiting that was mild in intensity but caused or prolonged hospitalization. A third subject received 450 µg/kg was hospitalized for febrile neutropenia. The events were considered unrelated to NEUG.

e. Pharmacokinetics

All subjects receiving NEUG were sampled for serum NEUG concentrations over the course of the study. The drug was detected using a sandwich enzyme-linked immunosorbent assay (ELISA) specific for NEUG. The serum drug concentration-time data was subjected to PK analysis using WinNonlin Enterprise Edition, Version 4.1 or higher, using noncompartmental or model-based analysis.

The following PK parameters were obtained: area under the curve ($AUC_{0-\infty}$), clearance (CL/F), volume of distribution (Vz/F), maximum concentration (Cmax), absorption half-life (t1/2, abs), elimination half-life (t1/2, elim), and mean residence time (MRT). Pharmacokinetic data were assessed for linearity across the dose range employed in the protocol.

Figure 27:
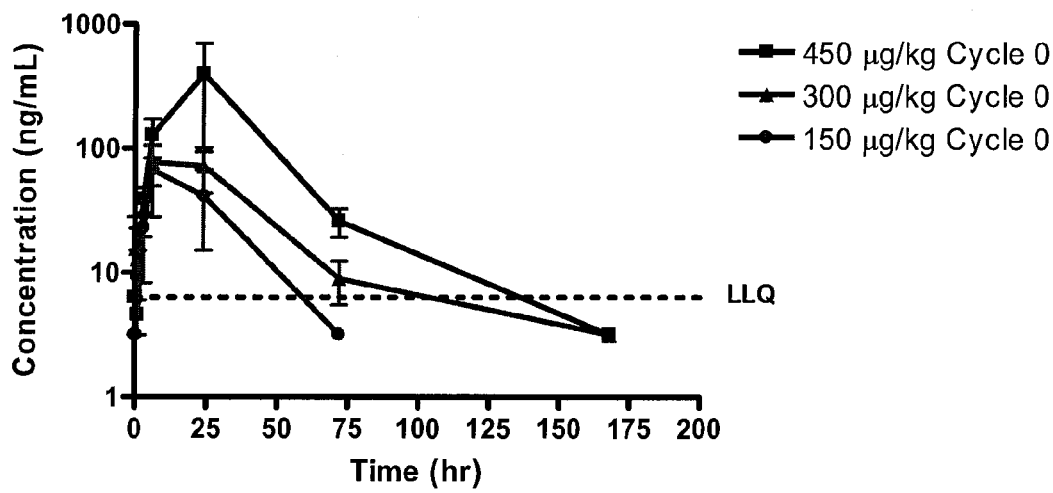
FIG. 27 is a graph showing the pharmacokinetics of NEUG in the Phase I study in human subjects. The serum concentration of NEUG administered subcutaneously at the indicated doses (450 μg/kg, 300 μg/kg or 150 μg/kg) was measured in subjects with breast cancer in the absence of chemotherapy. Squares: 450 μg/kg Cycle 0; triangles: 300 μg/kg Cycle 0; circles: 150 μg/kg Cycle 0.

Pharmacokinetic parameters from cycle 0 (pre-chemotherapy) are summarized in Table 18 and the cycle 0 PK profile is illustrated in FIG. 27.

TABLE 18

Neugranin Pharmacokinetics in Human Subjects
(Phase 1 Cycle 0)

| Parameter | NEUG | NEUG | NEUG |
|---|---|---|---|
| Dose (mcg/kg) | 150 µg/kg | 300 µg/kg | 450 µg/kg |
| Number of Subjects | 3 | 4 | 3 |
| AUC (hr * ng/mL) (mean ± SD) | 1758 ± 1675 | 3390 ± 2003 | 10131 ± 9563 |
| $t_{1/2,term}$ (hr) (mean ± SD) | 14.4 ± 4.0 | 23.5 ± 10 | 29 ± 9.3 |
| $C_{max}$ (ng/mL) (mean ± SD) | 72.7 ± 59.7 | 108.9 ± 50.5 | 294 ± 351 |
| $t_{max}$ (hr) (mean) | 12 | 15 | 18 |

Drug exposure as measured by maximum serum NEUG concentration and area under the time-concentration curve increased in a dose-dependent manner. Serum concentrations for subjects in the initial 50 µg/kg dose cohort were consistently below the lower limit of quantization (6.3 ng/mL). $T_{max}$ was in the range of 6-24 hours for all doses from 150 through 450 µg/kg. Cmax ranged from 72.7±59.7 (mean±SD) ng/mL at a dose of 150 µg/kg to 294±351 ng/mL, at a dose of 450 µg/kg. Correspondingly, $AUC_{0-\infty}$ ranged from 1758±1675 ng/mL*hr at a dose of 150 mcg/kg to 10131±9563 ng/mL*hr at a dose of 450 µg/kg. Cycle 1 ranges were similar. The mean elimination half-life of NEUG ranged from 14-30 hours.

Figure 24A:
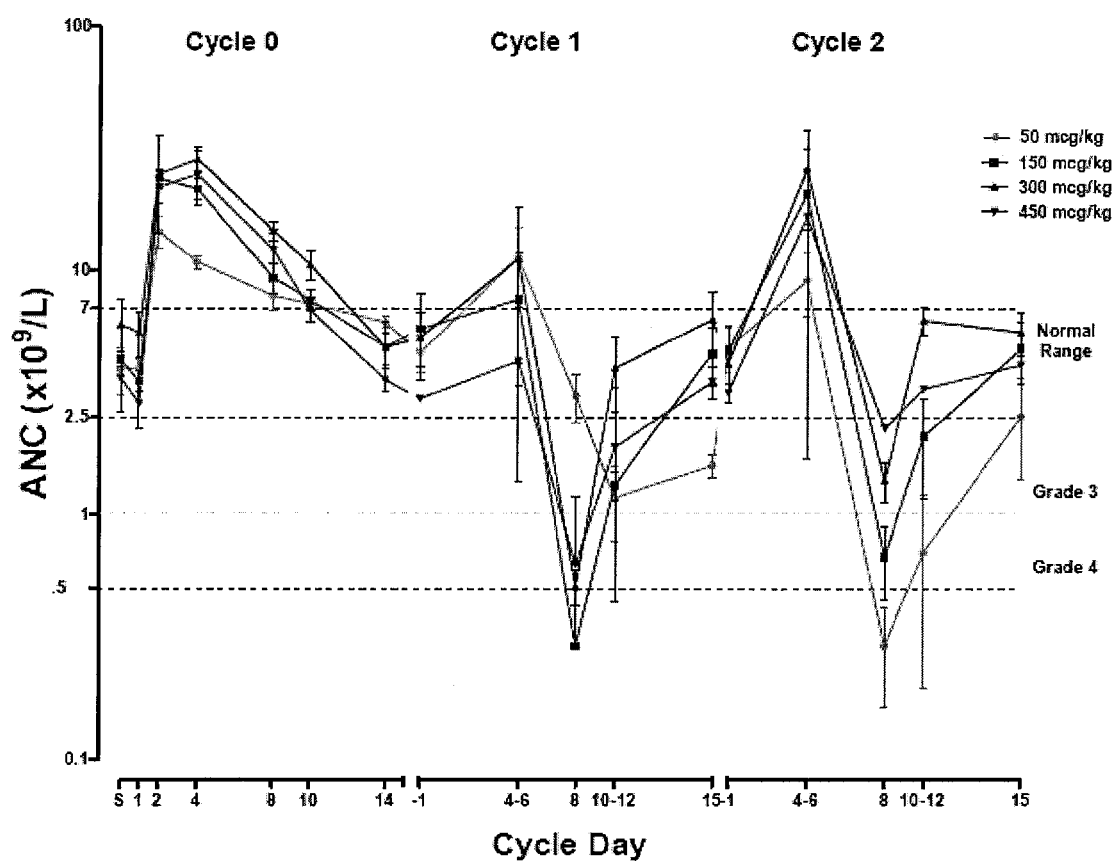
FIGS. 24A and 24B are graphs showing the ANC and white blood cell ("WBC") count for subjects who received NEUG-1 before and 24 hours after chemotherapy cycles. NEUG dosages were as follows: 50 μg/kg; 150 μg/kg; 300 μg/kg; or 450 μg/kg. The neutrophil cut-offs for grade 3 and 4 neutropenia are shown by dashed lines in 24A; the normal neutrophil range is also depicted in both 24A and 24B.
Figure 24B:
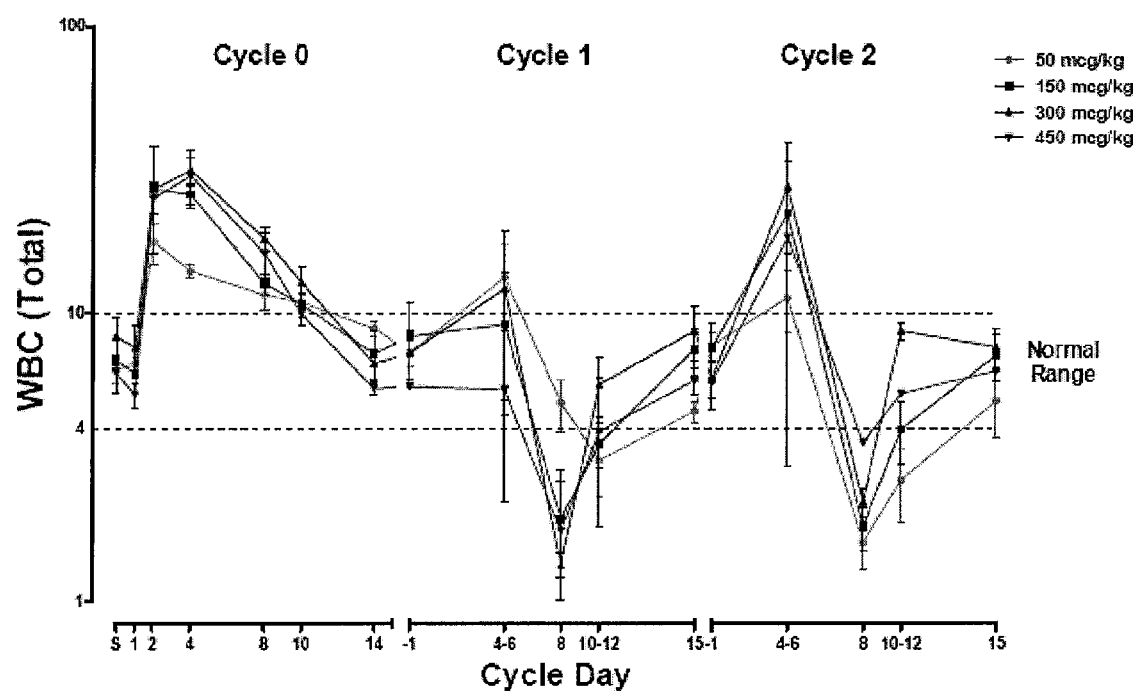
Figure 25:
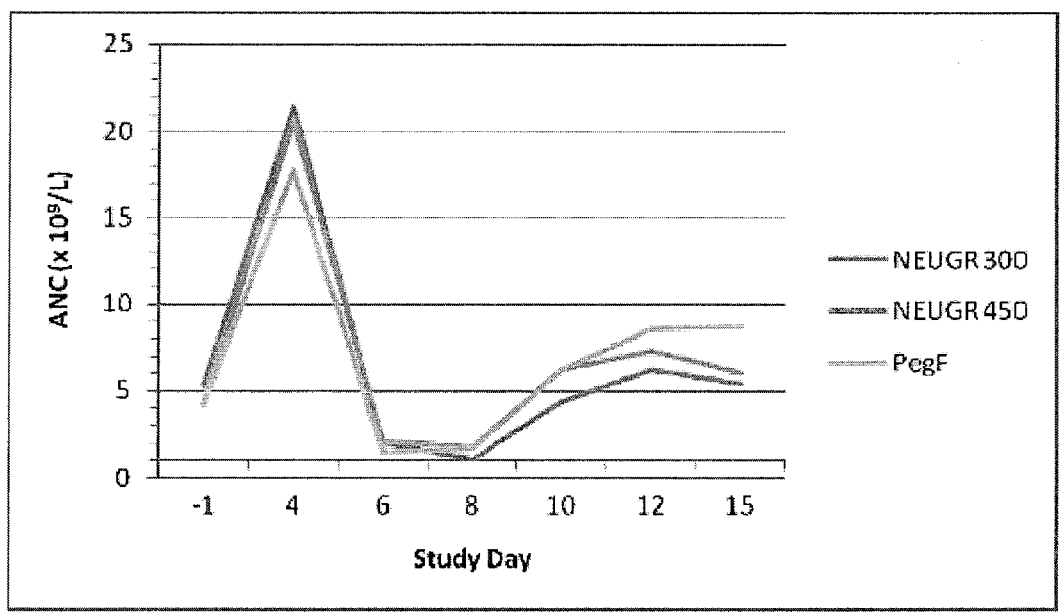
FIG. 25 is a graph showing the absolute neutrophil count (ANC) for subjects who received 300 μg/kg NEUG, 450 μg/kg NEUG or 6 mg pegfilgrastim (Neulasta®) approximately 24 hours following chemotherapy in cycle 1.

As noted in "Study Characteristics" (section 4, above), subjects in Part A received the first dose of NEUG at least 2 weeks prior to the start of chemotherapy (cycle 0) for an initial assessment of safety and effects on absolute neutrophil count ("ANC") in the absence of cytotoxic chemotherapy. After a minimum of 2 weeks follow-up, subjects received NEUG at the same dose following chemotherapy in cycles 1 and 2 if there were no dose-limiting adverse events considered related to NEUG in cycle 0 and the subject continued to meet all eligibility criteria. NEUG was administered 24 hours following chemotherapy administration. FIGS. 24A and 24B show the ANC and WBC count for subjects that received NEUG during cycles 1 and 2.

f. Pharmacodynamics and Establishment of Part B Dosages

Analysis of the data from Part A of Phase I of the study yielded the following observations:
1. NEUG induces a dose-dependent rise in WBC and ANC rise in Cycle 0 (prior to chemotherapy) (see cycle 0 data at FIGS. 24A and B).
2. ANC increases in Cycle 0 were comparable to historical data for pegfilgrastim at equimolar doses
3. As anticipated, WBC and ANC drop following chemotherapy
4. Recovery from Nadir ANC appears dose related
5. ANC and WBC returned to normal by day 15

Based on these observations and demonstration of safety at all dose levels in Part A, the doses chosen for the Part B evaluation were 300 and 450 µg/kg. As described above, subjects were randomized to NEUG 300 µg/kg, NEUG 450 µg/kg, or pegfilgrastim at the approved fixed dose of 6 mg. Subjects received the NEUG or pegfilgrastim one day following doxorubicin/docetaxel (administered for 2 cycles, 21 days apart). Data for Part B includes the cycle 1 ANC profiles of the population. Results are summarized in FIG. 28 and Table 18, below.

The incidence of grade 3 and 4 neutropenia, and the ANC profiles during Cycle 1 were determined in 48 of 51 treated subjects as show in Table 19. Note that 70-80% of patients treated with doxorubicin/docetaxel get Grade 4 neutropenia with durations average of 5 days in the absence of prophylactic G-CSF treatment.

TABLE 19

Incidence and duration of Grade 4 neutropenia in Phase I, Part B after cycle 1 of chemotherapy

| Treatment | NEUG | | Pegfilgrastim |
|---|---|---|---|
| Dose | 300 µg/kg | 450 µg/kg | 6 mg |
| Number of subjects | 20 | 21 | 10 |
| Grade 4 Neutropenia | 9 | 6 | 3 |
| % grade 4 neutropenia | 45.0% | 28.6% | 30.0% |
| Mean (days) | 1.1 | 1.0 | 0.7 |
| SD (days) | 1.33 | 1.67 | 1.16 |
| Range (days) | 0-4 | 0-5 | 0-3 |

Figure 28:
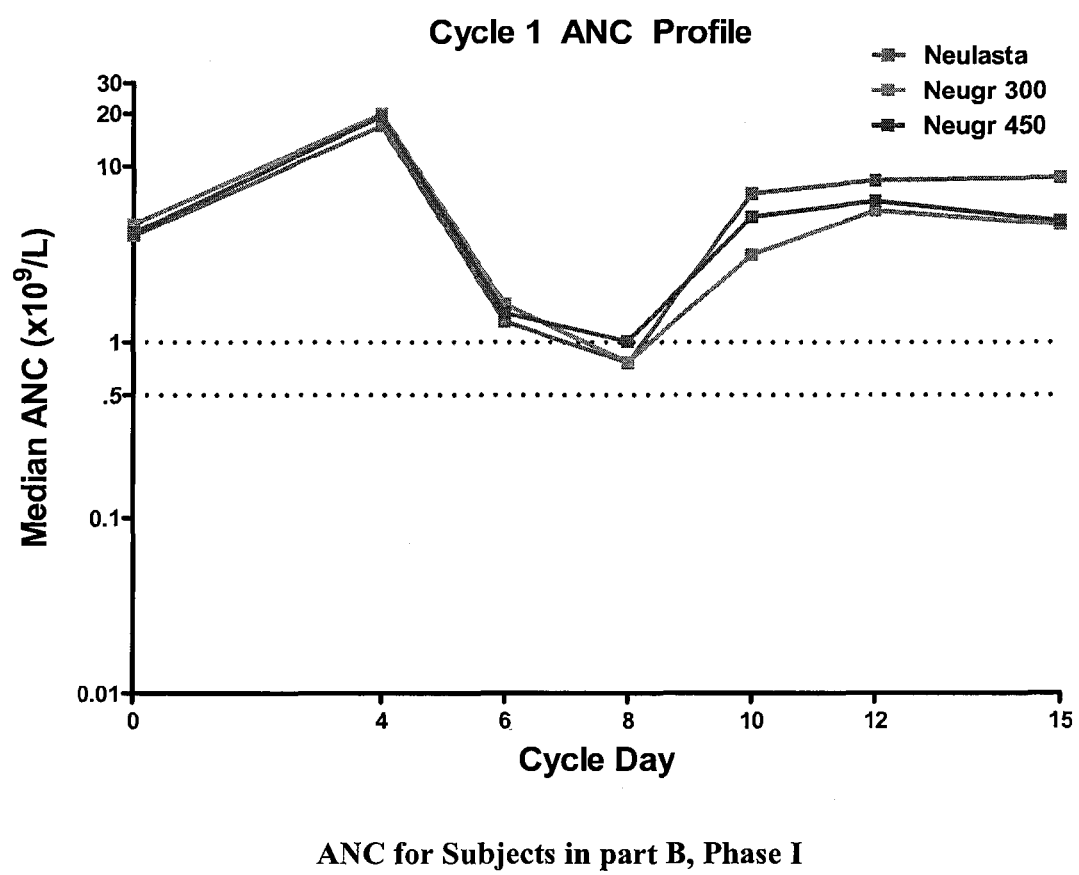
FIG. 28 is a graph showing the absolute neutrophil count ("ANC") for subjects in Phase I. Subjects received 300 μg/kg NEUG (n=19), 450 μg/kg NEUG (n=20) or 6 mg pegfilgrastim (Neulasta®) (n=9) in cycle 1 following study chemotherapy.

Mean ANC curves for the treatment groups are presented in FIG. 28.

NEUG is effective for treating grade 3, grade 4 and febrile neutropenia. In the absence of G-CSF treatment for this chemotherapy regimen, the incidence of febrile neutropenia is about 40%. A dose-related elevation in ANC and a lower rate of neutropenia than is expected with doxorubicin/docetaxel were observed following administration of NEUG. There were no unexpected or serious adverse events attributed to NEUG.

The incidence of grade 3 and grade 4 neutropenia was higher in patients receiving 300 µg/kg NEUG than those receiving pegfilgrastim (Neulasta®) and the rate of return to normal ANC also appeared slower in patients who received 300 µg/kg NEUG than in those subjects who received pegfilgrastim. The ANC profiles in patients who received NEUG at 450 µg/kg and those who received pegfilgrastim were similar, though the ANCs during recovery from neutropenia were generally lower in patients who received NEUG than in patients receiving pegfilgrastim. In summary, NEUG at these doses appears to provide similar effect as pegfilgrastim.

f. PK/PD Profile, Phase I, Part B

Figure 29:
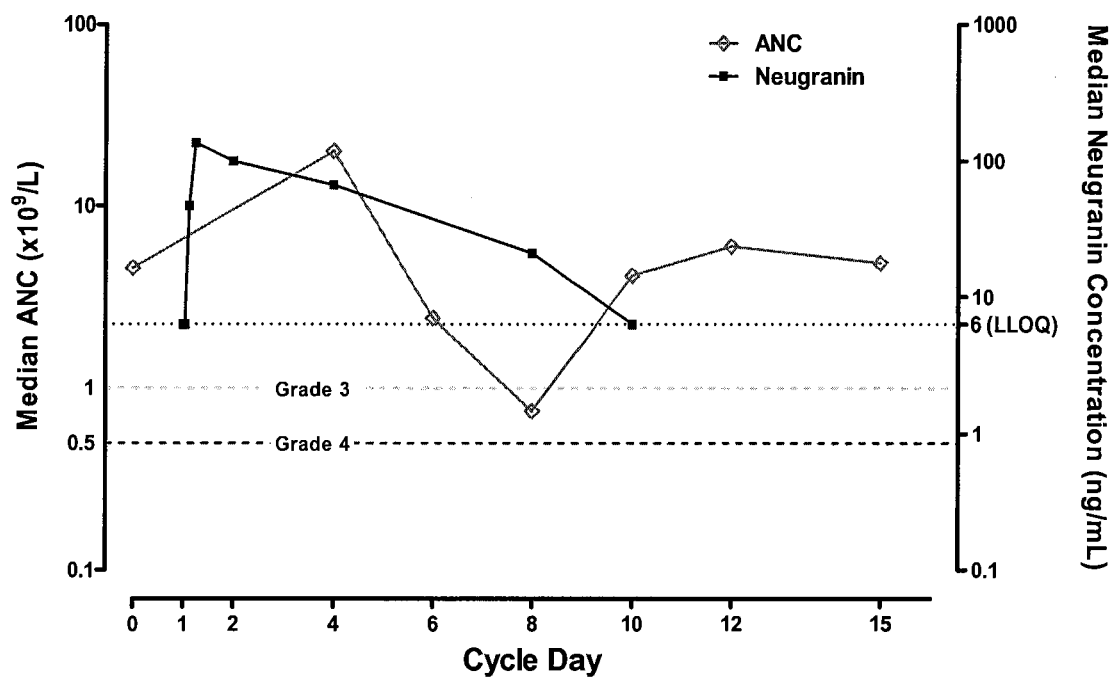
FIG. 29 is a graph showing the pharmacokinetics/pharmacodynamics ("PK/PD") of NEUG in cycle 1 of chemotherapy (Phase I study). Patients received 450 μg/kg of NEUG one day after doxorubicin/docetaxel administration in cycle 1. ANC is shown by the open diamonds; NEUG concentration is shown by closed squares. Cut-offs for neutropenia grades 3 and 4 are shown by the dashed lines. The Lower Limit of Quantitation ("LLOQ") for NEUG is shown as a dotted line at 6 ng/ml.

The PK/PD profile from patients receiving 450 µg/kg NEUG one day after doxorubicin/docetaxel administration in cycle 1 of treatment for breast cancer is shown in FIG. 29. Cmax for NEUG is achieved within one day of administration and gradually falls to undetectable levels by day 10. Following administration of NEUG, the ANC rises to a peak by day 4 and then, as expected in patients receiving doxorubicin/docetaxel and G-CSF treatment, the ANCs fall to a nadir on day 8 and return to normal on day 10. By day 12, ANC values are in the normal range and NEUG is undetectable. Note that in patients who do not receive prophylactic G-CSF treatment, the duration of nadir ANC and time to reach recovery ANC are much longer (e.g., 5-7 days). After a dose of 450 µg/kg, the NEUG median elimination half-life was approximately 30 hours, as compared to the 15-80 hours reported for a standard dose of pegfilgrastim.

g. Additional Differences Between NEUG and Pegfilgrastim

More detail of the differences between NEUG and pegfilgrastim at the tested doses in effectiveness in hastening the recovery form neutropenia is evident in comparison of the individuals ANC profiles in cycle 1 of treatment. The peak ANCs in all groups were very similar, nadir ANCs in subjects receiving NEUG at 300 µg/kg were lower than in subjects receiving NEUG at 450 µg/kg, and the ANC nadirs in subjects receiving pegfilgrastim were on average the highest. Recovery from nadir ANC to baseline occurred by day 14 in all treatment groups, but was slower for those receiving 300 µg/kg NEUG, than 450 µg/kg NEUG, and most rapid for subjects receiving pegfilgrastim.

Available published data for a pegfilgrastim trial with a similar prechemotherapy administration were compared to NEUG PK/PD data from patients who completed the Phase I through the scheduled cycle 0 (pre-chemotherapy). Results of this comparison were as follows:

1. Emax (maximum observed ANCs) at NEUG dose of 150 µg/kg matches the 30 µg/kg dose of pegfilgrastim in Cycle 0, a dose later demonstrated to be inferior for efficacy to the confirmed efficacious pegfilgrastim dose of 100 µg/kg.
2. Emax for 300 and 450 µg/kg Neugranin doses are more consistent with Cycle 0 levels for 100 µg/kg dose of pegfilgrastim.
3. At 300 and 450 µg/kg NEUG median Cmax and median Emax are nearly the same, thus Cmax continued to predict Emax.
4. ANC increases were comparable to published data for pegfilgrastim at equimolar doses.

As discussed above, PK/PD assessment in animals and in man was consistent with an estimate of NEUG and pegfilgrastim dose equivalence when dosed on an equimolar basis. In mice, equivalent $AUC_{ANC}$ were achieved with a 7.7 fold higher dose thane pegfilgrastim. Because albumin contributes significantly to the molecular weight of NEUG, and Neulasta® (pegfilgrastim) is dosed base on the weight of the rhG-CSF (not including the contribution of the polyethylene glycol in pegfilgrastim), a 4.5 fold greater dose of NEUG (based on weight) is predicted to be as effective as an equal dose of Neulasta® (pegfilgrastim). Efficacy data in animals were consistent with a 4.5-7.7 fold equivalence to pegfilgrastim (1 mg pegfilgrastim=4.5-7.7 NEUG). Non-clinical safety and effect data are consistent with this dose estimate and when considered with available clinical data, form the basis for the doses elected for clinical evaluation.

h. Results of Phase I

The Results from the Phase I pharmacokinetic evaluation are as follows.

NEUG was detected in serum samples from all subjects treated with NEUG at doses of 150 µg/kg, 300 µg/kg and 450 µg/kg on Cycle 0 and Cycle 1.

In Cycle 1, NEUG was detected uptown 144 hours in most subjects (45/50 sampled) in the 150 mg/kg, 300 µg/kg and 450 µg/kg dose groups. Virtually no cycle to cycle drug accumulation was observed.

Drug exposure was higher in Cycle 1 and in Cycle 0 (pre-chemotherapy) with each dose group. The increased exposure to NEUG in Cycle 1 is likely due to the decreased number of neutrophils, which plan a role in the receptor-mediated clearance of G-CSF.

The median elimination half-life of NEUG in Cycle 1 was about 36 hours for dose group 300 µg/kg and 30 hour for dose group 450 µg/kg. The elimination half-life is reported to be 3-4 hours for filgrastim and 42-67.5 hours, depending on dose, for pegfilgrastim.

Statistically significant differences across doses were observed in the time to maximal serum concentration ($t_{max}$) and the absorption half-life ($t_{1/2,abs}$). Both of these parameters increased with increasing NEUG dose. No other dose normalized PK parameters showed statistically significant differences across doses.

Example 11

Phase II

Phase II of the study was a controlled, randomized trial, conducted in 334 subjects with breast cancer who received up to 4 doses of doxorubicin/docetaxel. The study, was conducted at approximately 50 clinical sites, and consisted of a two-way randomized pilot phase to assess the safety and effect of subcutaneously administered NEUG versus pegfilgrastim, followed by a main phase in which subjects were randomized to pegfilgrastim and two, well-tolerated doses of NEUG (1:1:1) selected based on the pilot phase. The sample size for the main phase was powered to establish non-inferiority of NEUG to pegfilgrastim with regard to the primary endpoint, duration of sever (grade 4) neutropenia (DSN) during chemotherapy cycle 1. The study design is shown schematically below.

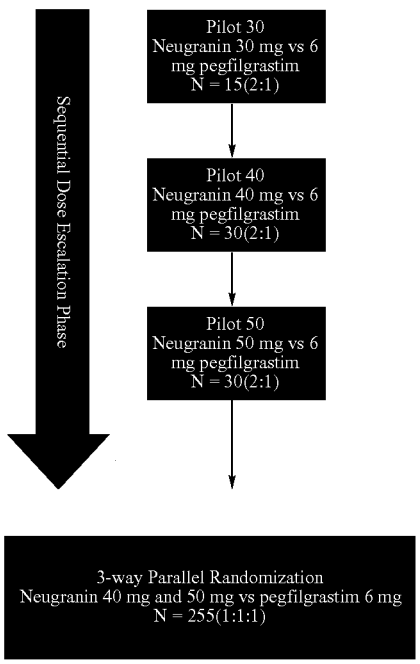

1. Objectives

The primary objectives of Phase II were to select doses of NEUG demonstrating a comparable effect to pegfilgrastim and to assess the duration of severe neutropenia (DSN) in cycle 1 of chemotherapy after treatment with NEUG. Secondary objectives were to assess the DSN in cycles 2-4, to assess the time to absolute neutrophil count recovery and rates of febrile entroopenia in cycles 1-4; and to assess the safety, tolerability, pharmacokinetics (in cycle 1), and immunogenicity of NEUG.

2. Patient Characteristics

For Phase II, patients were screened based on the following characteristics or parameters:

Inclusion:
1. Patients with histologically-confirmed breast cancer scheduled to receive doxorubicin 60 mg/m$^2$ and docetaxel 75 mg/m$^2$
2. 18 years of age or older
3. Adequate hematologic function:
4. ANC>1500/mm$^3$
5. Platelets>100,000/mm$^3$
6. Adequate hepatic and renal function:
7. Serum creatinine<1.5×upper limit normal
8. Total bilirubin within normal limits (WNL) for local laboratory
9. Serum transaminases (SGOT/SGPT)<1.5×upper limit normal
10. Alkaline phosphatase<2.5×upper limit normal
11. Eastern Cooperative Oncology Group ("ECOG") performance status 0-2
12. Eligible to receive doxorubicin based on a left ventricular ejection fraction (LVEF) within normal limits
13. Have the ability to understand the requirements of the study, provide written informed consent (including consent for use and disclosure of research-related health information) and comply with the study protocol procedures.

Exclusion:
1. More than 1 prior chemotherapy regimen (including adjuvant therapy if given within the last 12 months)
2. A cumulative anthracycline dose that would preclude 4 full-dose cycles of doxorubicin in this study
3. Prior chemotherapy/immunotherapy within 30 days prior of study chemotherapy (within 6 weeks of study chemotherapy for nitrosoureas (BCNU, CCNU) or mitomycin-C)
4. Concomitant trastuzumab (Herceptin)
5. Received any investigational agent in the past 30 days
6. Cardiac history, signs or symptoms that, in the Investigator's opinion, preclude the use of an anthracycline-based chemotherapy regimen
7. Prior surgery within 2 weeks of study chemotherapy
8. Prior radiation therapy within 4 weeks of study chemotherapy (except spot irradiation for bone metastases)
9. Prior high-dose chemotherapy with hematopoietic stem cell transplant
10. Prior use of G-CSF, GM-CSF or erythropoietin within 4 weeks of study chemotherapy
11. Received systemic antibiotics within 72 hours of study chemotherapy
12. History of myeloid malignancy or myelodysplasia
13. Known brain metastases unless adequately treated (surgery or radiotherapy), no evidence of progression with a minimum of 3 weeks observation and neurologically stable off anticonvulsants and steroids.
14. Known sickle cell disease
15. Diagnosis of adult respiratory distress syndrome (ARDS)
16. Known history of allergies to yeast-derived products
17. Known hypersensitivity to *E coli*-derived proteins, pegfilgrastim, filgrastim, or any other component of pegfilgrastim
18. Pregnant female or nursing mother. (All females with an intact uterus must have a negative serum pregnancy test at screening. All non-sterile or non-postmenopausal females must practice a medically accepted method of contraception over the course of the study and for 30 days after the last dose of study agent.)
19. Males who do not agree to use effective contraception throughout the study and for a period of 30 days after the last dose of study agent
20. Known HIV positive or active hepatitis (Patients with unknown status will not be tested)

Subjects were removed from further treatment for the following reasons:
1. Disease progression
2. Unacceptable toxicities despite optimal treatment
3. Intercurrent illness at the investigator's discretion
4. Doxorubicin regimen—Maximum lifetime permissible cumulative dose reached (see eligibility criteria)
5. Withdrawal of consent
6. Non-compliance/Loss to follow-up
7. Pregnancy If treatment with study drug was stopped, subjects remained on study were followed at least 30 days following the final dose of any study drug for scheduled safety and PK assessments.

3. Study Agent

NEUG (recombinant human albumin-human granulocyte colony stimulating factor, rHSA-GCSF), is a fusion protein with a molecular mass of approximately 85 kDa connected in a single chain comprising residues 1-585 corresponding to the mature form of HSA and residues 586-759 corresponding to the mature form of human G-CSF. The therapeutic moiety of NEUG is recombinant human DNA-derived G-CSF.

NEUG was supplied as a sterile, lyophilized formulation in single-use Type 1 glass vials and stored at 2-8° C. Upon reconstitution with 1.0 ml of sterile water for injection, each vial contains 50 mg/ml (50 mg/vial deliverable) NEUG in 20 mM sodium phosphate, 180 mM, mannitol, 60 mM trehalose dehydrate, 0.01% (w/v) polysorbate 80, pH 6.0.

The composition of the drug product used in Phase II is shown in Table 11. Difference between the NEUG formulations used in Phase I and Phase II are shown below in Table 20.

TABLE 20 cGMP formulation comparison

| Excipient Formulation Attribute | Phase I formulation | Phase II formulation | Rationale for change |
|---|---|---|---|
| API | 15.0 mg/mL | 50 mg/mL | Increased API concentration to reduce volume of injection |
| Sodium Phosphate | 10 mM | 20 mM | Higher ionic strength reduces concentration dependent aggregation |
| Mannitol | 200 mM | 180 mM | Reduced to provide iso-osmotic solution |
| Trehalose dihydrate | 60 mM | 60 mM | Unchanged-acts as robust cryo/lyo protectant. |
| Polysorbate 80 | 0.01% | 0.01% | Unchanged-inhibits nonspecific aggregation and adsorption |
| pH | 7.2 | 6.0 | Lower pH reduces concentration dependent aggregation |

The formulation used in Phase I was quite stable, with a shelf-life of at least 2 years. Studies demonstrated that higher ionic strength and lower pH further stabilized the API at higher concentration (>25 mg/mL) (data not shown). To this end, the Phase II formulation has a lower pH (6.0 vs 7.2) and higher phosphate concentration (20 vs. 10 mM). Forced degradation studies demonstrate that this formulation protects the drug substance in the liquid state from vigorous shaking, repeated freeze-thawing, and concentration induced aggregation. Freeze drying of the Phase II formulation also produces well-formed cakes.

Commercially available Neulasta® (pegfilgrastim) is supplied in 0.6 ml prefilled syringes for subcutaneous injection. Each syringe contains 6 mg pegfilgrastim (based on protein weight), in a sterile, clear, colorless, preservative-free solution (pH 4.0) containing acetate (0.35 mg), sorbitol (30.0 mg), polysorbate 20 (0.02 mg), sodium (0.102 mg) in water for injection. USP.

NEUG (30, 40, 50, or 60 mg) or Neulasta® (pegfilgrastim) (6 mg) was administered by subcutaneous administration.

Dose Rationale

Figure 30:
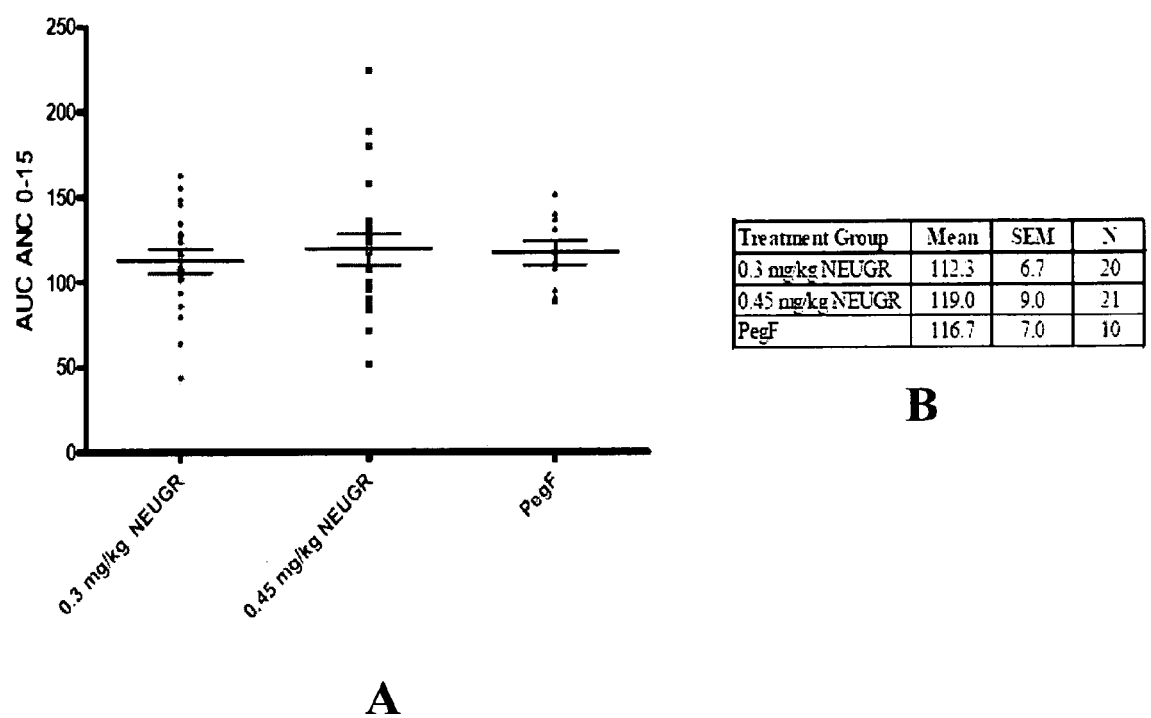
FIGS. 30A and 30B show the area the curve (AUC) for each subject treated in Phase I, Part B, based on the ANC values obtained for days 0 to 15.

The data from Phase I demonstrated that doses of NEUG of 300 and 450 µg/kg were safe and well tolerated. Moreover, compared to the approved fixed doses of pegfilgrastim, both doses of NEUG resulted in similar effects on ANC profiles in breast cancer patients receiving cytotoxic chemotherapy. The AUC for the ANC profiles serves as a single-point measure of effect. There was no statistically significant difference among these treatment groups in terms of $AUC_{ANC}$, however, the AUC for the 450 µg/kg group is slightly higher than that observed for the 300 µg/kg group and nearly identical to that observed for the pegfilgrastim group (FIG. 30). Based on available data, it was estimated that 300 µg/kg NEUG was less effective than pegfilgrastim and 450 µg/kg approximates a minimum necessary dose to provide equivalent effect to pegfilgrastim.

The intent of a fixed dose is to identify doses that will provide patients with a dose sufficient to provide efficacy and safety regardless of patient weight. Based on the results of Phase I, it as estimated that 450 µg/kg NEUG may be a minimum dose necessary to provide similar effect as pegfilgrastim, and >300 µg/kg was set as the minimum dose for further evaluation in Phase II. To select fixed doses of NEUG, the patient population (breast cancer) for Phase II was modeled. Using 40-100 kg weight range, a 30 mg fixed dose provides the heaviest patient with a minimum dose (300 µg/kg or 0.3 mg/kg), while approximately 75% of patients receive at least the target dose, 450 mg/kg, at a fixed dose of 40 mg. Thus, the doses selected for evaluation in Phase II were 30 mg, 40 mg and 50 mg. These provide an average 70 kg patient with 0.42, 0.57 and 0.71 mg/kg doses, respectively.

The equivalent dose per kilogram based on the fixed doses evaluated in this trial is provided in Table 21.

TABLE 21

Equivalent dose per kilogram for the anticipated subject weight range

| | 50 kg | 60 kg | 70 kg | 80 kg | 90 kg | 100 kg |
|---|---|---|---|---|---|---|
| 30 mg | 0.600 | 0.500 | 0.429 | 0.375 | 0.333 | 0.300 |
| 40 mg | 0.800 | 0.667 | 0.571 | 0.500 | 0.444 | 0.400 |
| 50 mg | 1.000 | 0.833 | 0.714 | 0.625 | 0.556 | 0.500 |
| 60 mg | 1.200 | 1.000 | 0.857 | 0.750 | 0.666 | 0.600 |

The nonclinical safety for NEUG provides additional support for the expectation of safety at these doses. Exposure in patients at these fixed doses (AUC and Cmax) is expected to be lower than exposure at well tolerated doses in monkeys. For example, Cmax and AUC in the monkey at the well-tolerated dose of 1 mg/kg was 12-fold higher than exposure in patients at 0.45 mg/kg suggesting a further margin of safety exists for higher dose evaluation in patients and in a repeat-dose toxicology study in monkey, doses up to and including 10 mg/kg were well tolerated. Doses of pegfilgrastim as high as 0.3 mg/kg have been demonstrated to be safe in patients.

4. Study Characteristics a. Study Schedule and Duration

This study was a controlled, randomized trial conducted in approximately 330 subjects with breast cancer scheduled to receive up to 4 doses of doxorubicin/docetaxel. The study, which was conducted at approximately 45 clinical sites, consisted of two phases, a pilot phase and a main phase.

The pilot phase, Part A, consisted of a two-way randomized study to assess the safety and effect of NEUG versus pegfilgrastim, with sequential enrollment to the following doses: NEUG 30 mg (N=10) vs. pegfilgrastim (N=5); NEUG 40 mg (N=20) vs. pegfilgrastim (N=10), and NEUG 50 mg (N=20) vs. pegfilgrastim (N=10). In a further study, NEUG 60 mg (N=20) vs. pegfilgrastim (N=10) could also be tested. In the Part A pilot phase, subjects were randomized in a 2:1 ratio of NEUG to pegfilgrastim with a total of 10 subjects in the 30 mg cohort and 20 subjects for each of the other cohorts. NEUG or pegfilgrastim was administered to subjects 24 hours after the chemotherapy treatment in each cycle. Subjects were assigned to treatment groups using a stratified randomization for balance among treatment groups based on weigh (<50 kg, $\geq$50 kg and <80 kg, or $\geq$80 kg), prior chemotherapy exposure and global location.

Following the pilot phase, 255 subjects were randomized (1:1:1) to pegfilgrastim and the two well tolerated doses of NEUG with the more comparable effect to pegfilgrastim in the pilot phase (a 3-arm, balanced parallel-randomized phase). NEUG or pegfilgrastim was administered 24 hours after the chemotherapy treatments in each cycle. Subjects were assigned to treatment groups using a stratified randomization for balance among treatment groups based on weight (<50 kg, $\geq$50 kg and <80 kg, or $\geq$80 kg).

During the pilot phase, adverse events were reviewed on an ongoing basis. Escalation of the dose from 30 through 50 mg occurs unless the ongoing review of data suggested a safety concern. If the Cycle 1 ANC profile for Neugranin at 40 mg appeared inferior to the profile observed from pegfilgrastim patients and 50 mg of Neugranin is safe, then an additional arm may be randomized in a 2:1 ratio of Neugranin at 60 mg to pegfilgrastim with a total of 30 patients in the cohort.

Each dose level of NEUG is compared to pegfilgrastim for safety and efficacy. Table 22 summarize the patient allocation for Phase II, Part A and Part B.

TABLE 22

Allocation of Subjects in Phase II, Parts A and B

| Phase | NEUG 30 mg | NEUG 40 mg | NEUG 50 mg | Pegfilgrastim 6 mg |
|---|---|---|---|---|
| Pilot 30 | 10 | — | — | 5 |
| Pilot 40 | — | 20 | — | 10 |
| Pilot 50 | — | — | 20 | 10 |
| 3-Arm Randomized | — | 85 | 85 | 85 |
| Total | 10 | 105 | 105 | 110 |

Safety Evaluation:

The safety of NEUG was assessed by evaluation of the type, frequency, and severity of AEs, changes in clinical laboratory tests (hematology and clinical chemistry), immunogenicity, physical examinations, and the monitoring of vital signs over time. All AEs and laboratory toxicities were graded based on the National Cancer Institute Common Terminology Criteria for Adverse Events (NCI-CTCAE Version 3.0, 12 Dec. 2003).

Adverse events were captured from the start of study drug administration through 30 days following the final dose of any study drug. Serious adverse events (SAE) were captured from the time of consent through 30 days following the final dose of any study drug. Laboratory assessments were obtained as outlined in the Schedule of Assessments.

c. Concomitant Therapy

Chemotherapy

The chemotherapy regimen for this trial consisted of doxorubicin 60 mg/m$^2$ and docetaxel 75 mg/m$^2$ administered sequentially by intravenous infusion on day 1 of treatment for up to four 21-day cycles.

Prior to receiving each cycle of therapy, subjects were required to have an absolute neutrophil count (ANC)>1000/mm$^3$ and platelets>100,000/mm$^3$. Treatment could be delayed up to two weeks for hematologic recovery. A 25% dose reduction of chemotherapy doses was allowed for grade 3-4 non-hematologic toxicities, two grade 3-4 infectious episodes, or grade 4 thrombocytopenia. The use of prophylactic antibiotics or other hematopoietic growth factors was prohibited during trial participation.

The combination of doxorubicin and docetaxel has been reported to have significant clinical activity in patients with breast cancer. However, the combination is highly myelosuppressive with higher rates of grade 3 or 4 neutropenia than other standard regimens.

Even with the addition of CSFs, the combination of doxorubicin and docetaxel has induced Grade 4 neutropenia in 79% of patients and febrile neutropenia rates of 9-18%. This doxorubicin/docetaxel regimen has been used in studies of new agents to prevent neutropenia and its complications. Therefore, the combination of doxorubicin and docetaxel is an appropriate chemotherapy regimen to study the potential of a new agent like NEUG.

Doxorubicin

Pharmacologic Data

Doxorubicin hydrochloride is an anthracycline antibiotic obtained from *streptomyces peucetius* var *caesius* which binds directly to DNA base pairs (intercalates) and inhibits DNA and DNA-dependent RNA synthesis, as well as protein synthesis. Doxorubicin is active in all phases of the cell cycle but maximally cytotoxic in S phase. Excretion of the drug is predominately by the liver; renal clearance is minor.

Pharmaceutical Data

The drug is marketed commercially in 10, 20 50, 100 or 200 mg vials. Lyophilized preparations may be reconstituted with sterile water for injection, dextrose 5% solution, or 0.9% saline for injection.

Side Effects and Toxicity

Myelosuppression, primarily leukopenia, with a nadir of approximately 10-14 days, and cardiotoxicity, including a rare, acute pericarditis-myocarditis syndrome and a delayed, cumulative dose related cardiomyopathy are the dose-limiting toxicities of doxorubicin.

Marked alopecia and moderate nausea/vomiting are expected toxicities. Extravasation reactions producing local skin and tissue damage at the site of inadvertent extravasation, stomatitis, hyperpigmentation of the skin (particularly the nailbeds), and a "recall" phenomenon at sites of previous irradiation have been reported.

Docetaxel

Pharmacologic Data

Docetaxel is a semisynthetic taxoid that binds to free tubulin and promotes assembly of stable microtubules, interfering with mitosis and cell replication (cell cycle specific for M phase). Docetaxel is extensively protein-bound, extensively metabolized in the liver, with fecal excretion of approximately 75% of the dose within 7 days.

Pharmaceutical Data

Docetaxel (Taxotere™, Sanofi Aventis) is provided in 80 mg/2 mL or 20 mg/0.5 ml single-dose vials with an accompanying diluent (13% ethanol in Water for Injection) vial. Each ml of Taxotere contains 40 mg of docetaxel (anhydrous) and 1080 mg polysorbate 80.

Side Effects and Toxicity

Docetaxel should not be given to patients who have a history of severe hypersensitivity reactions to docetaxel or other drugs formulated with polysorbate 80 such as etoposide and vitamin E.

Patients who experience severe hypersensitivity reactions should not be rechallenged. All patients receiving docetaxel should be premedicated with corticosteroids as outlined below.

Mild to moderate liver impairment results in delayed metabolism by 27% and a 38% increase in systemic exposure (AUC). Docetaxel should not be given to patients with SGOT and/or SGPT>1.5 times normal limits and alkaline phosphatase>2.5 times normal limits. Fluid retention occurred in 17% (moderate) and 6% (severe retention) of patients in phase III studies despite corticosteroid premedication. Severe neurosensory symptoms (paresthesia, dyesthesia, pain) have been observed.

Expected side effects include myelosuppression, primarily leukopenia, with a nadir of approximately 9 days with recovery by day 15-21. Alopecia, nail and cutaneous changes, stomatitis, myalgia/arthralgia, nausea/vomiting, and hypotension have been reported.

Chemotherapy Dosage, Administration and Dose Modifications

On day 1 of each treatment cycle, chemotherapy (doxorubicin followed by docetaxel) was to be administered.

Doxorubicin was administered at a dose of 60 mg/m$^2$ by IV bolus through the side arm of an infusing intravenous line or central venous catheter to avoid extravasation injury.

Docetaxel 75 mg/m$^2$ was diluted in 250 ml 0.9% saline or 5% dextrose solution and administered intravenously over approximately 1 hour via a polyethylene-lined infusion set. Vital signs were obtained immediately prior to and after the end of the docetaxel infusion.

Subjects experiencing severe hypersensitivity reactions or non-hematologic toxicities that preclude further cycles of chemotherapy were to be removed from study treatment and complete follow-up.

Chemotherapy Pre-Medication

Oral (IV as needed) corticosteroids (such as dexamethasone 8 mg BID) was administered for three days starting 1 day prior to docetaxel administration in order to reduce the incidence and severity of fluid retention and hypersensitivity reactions.

The use and selection of anti-emetic agents or other pre-medications (e.g. H$_2$ antagonists) was left to the discretion of the treating physician.

Prohibited Medications

Subjects were not to receive any of the following medications and or procedures during this study and for the additional times specified below:

1. Systemic antibiotics within 72 hours of cycle 1 chemotherapy.
2. Other investigational agents within 30 days of initiating study agent and for the duration of the trial
3. Subsequent cycles of chemotherapy should not be initiated until 14 days following dosing with NEUG.
4. Cytokines, other hematopoietic growth factors and prophylactic antibiotics for the duration of the trial unless prolonged or febrile neutropenia occurs. If the subject is treated with G-CSF at any time between the screening period and Day 0 they will not be eligible to receive NEUG and will be discontinued from the study.

Allowed Medications

Subjects were allowed to continue their baseline medications(s). The daily dose of each medication was maintained throughout the study if possible. If for any reason deemed necessary by the investigator, a subject required additional medication(s) or change of dose, the medication(s), route of administration, and the indication for which it was given was be recorded.

Subjects experiencing severe hypersensitivity reactions or non-hematologic toxicities that preclude further cycles of chemotherapy were removed from study treatment and completed follow-up.

d. Pharmacokinetics

All subjects receiving NEUG were sampled for serum NEUG concentrations during cycle 1. The drug was detected using a sandwich enzyme-linked immunosorbent assay (ELISA) specific for NEUG. The serum drug concentration-time data was subjected to PK analysis using WinNonlin Enterprise Edition, Version 5.0 or higher, using noncompartmental or model-based analysis. The following PK parameters were determined: area under the curve ($AUC_{0-\infty}$), clearance (CL/F), volume of distribution (Vz/F), maximum concentration (Cmax), absorption half-life (t1/2, abs), elimination half-life (t1/2, elim), and mean residence time (MRT).

e. Immunogenicity

Serum samples for antibodies to NEUG were obtained prior to dosing on Day 1 of every NEUG cycle and at the end of treatment visit (approximately 30 days after the last dose) in subjects receiving NEUG. If at any time during the study a subject developed a positive anti-NEUG antibody response, a repeat sample was obtained approximately 6 months after the final NEUG dose; if this sample was positive, a sample was obtained at 12 months. The protocol was later amended to require 6 and 12 month immunogenicity samples from all subjects.

5. Results a. General

Statistical Methods

The sample size of about 85 subjects per arm in the main phase of this trial (Part B) was chosen to provide 91% power to establish non-inferiority of NEUG to pegfilgrastim with regard to the primary endpoint of mean duration of severe neutropenia (DSN) in cycle 1, with a non-inferiority margin of 1 day and an overall 1-sided significance level adjusted for multiple testing (by the Hochberg method) of 0.025. Sample sizes were calculated based on the normal approximation for two independent groups, an estimate of 1.6 days as the within-treatment standard deviation of cycle 1 DSN, and a maximum rate of 20% not evaluable for the primary endpoint of cycle 1 DSN.

Efficacy comparison was made between the two selected NEUG doses (either 40 mg and 50 mg) and pegfilgrastim, based on subjects in the 3-arm randomized phase (Part A).

Secondary efficacy analyses include the DSN in each of chemotherapy cycles 2 through 4, depth of ANC nadir in each of the cycles 1 through 4, rates of FN (defined as ANC<0.5×10$^9$/L with coincidental oral equivalent temperature>38.2° C.) by cycle and across all cycles, and times to ANC recovery to >1.5×10$^9$/L in all cycles.

The data related to secondary efficacy analysis was analyzed using appropriate statistical methods. Safety, PK, and immunogenicity parameters were analyzed by descriptive statistical methods.

For frequency and severity of adverse events, and for laboratory toxicity grading, counts and rates are presented.

Efficacy Measures

Complete blood counts ("CBC") were obtained on day 1, 3 and daily from day 5 until ANC>$2.0 \times 10^9$/L after the nadir, then twice weekly, and at the end of treatment.

b. Efficacy of Phase II, Part A

Of the 78 subjects enrolled in the pilot phase of the study, 13 subjects did not complete the study, 3 (27.3%) treated with NEUG 30 mg, 3 (14.3%) treated with NEUG 40 mg, 3 (15.0%) treated with NEUG 50 mg, and 4 (15.4%) treated with pegfilgrastim. The most frequent reasons for early discontinuation were withdrawal of consent (7 subjects) and decision of the investigator (3 subjects). One NEUG 30 mg subject was withdrawn due to an adverse event (diabetic foot).

The incidence of sever neutropenia and the mean duration of severe neutropenia (DSN) were similar across treatment groups in each chemotherapy cycle; however, the time to ANC recovery and the incidence of febrile neutropenia suggested that NEUG 30 mg was not quite as effective as NEUG 40 mg, NEUG 50 mg, or pegfilgrastim.

During Cycle 1, the proportion of subjects experiencing febrile neutropenia was 20.0%, 9.5%, 10.0% and 8.0% for the NEUG 30 mg, 40 mg, 50 mg and pegfilgrastim group, respectively. Febrile neutropenia was observed for only three additional subjects during Cycles 2-4, one each in the NEUG 30 mg, NEUG 40 mg and pegfilgrastim groups. FIG. 5 shows the ANC profile of a subset of patients receiving either NEUG 30 or pegfilgrastim and who later presented with grade 4 neutropenia.

In Cycle 1, the mean DSN was similar for NEUG 30 mg (0.9 days), NEUG 50 mg (1.1 days), and pegfilgrastim (0.9 days). Although the mean DSN was slightly longer for NEUG 40 mg (1.6 days) than the other three treatments, the differences among treatments were all less than 1 day, the criterion to consider the treatments equivalent in the main phase. The median DSN was 0 or 1 day in all four treatment groups.

Summary statistics for the incidence and duration of Grade 3 or 4 neutropenia followed a similar pattern, i.e., the NEUG 30 mg, NEUG 50 mg, and pegfilgrastim groups had similar outcomes, while the incidence and duration of Grade 3 or 4 neutropenia were slightly higher for the NEUG 40 mg group than for the other treatment groups. The number of subjects in the pilot phase (Part A) was fairly small, and the observed differences were not statistically significant. NEUG 40 mg and NEUG 50 mg were selected for further evaluation in Part B, the 3-arm randomized phase of the study.

c. Efficacy of Phase II, Part B

Of the 256 subjects enrolled in the main phase of the study, 18 subjects did not complete the study; 10 (11.6%) treated with NEUG 40 mg, 5 (6.0%) treated with NEUG 50 mg, and 3 (3.5%) treated with pegfilgrastim. The most frequent reasons for early discontinuation were withdrawal of consent (7 subjects) and AEs (4 subjects), including 2 deaths. The investigator considered all of these AEs to be not related to study medication or chemotherapy. In the main phase, 1 (1.2%) NEUG 40 mg subject was withdrawn before being treated with study drug.

The incidence and duration of sever neutropenia in Cycle 1 are summarized in Table 23.

TABLE 23

Phase II, Part B: Incidence and duration of severe neutropenia in Cycle 1

| | Neugranin | | | Pegfilgrastim (N = 86) | |
|---|---|---|---|---|---|
| | 40 mg (N = 85) | 50 mg (N = 84) | All Neug. (N = 169) | | |
| | | | | | 95% CI 97.5% CI |
| Incidence of severe neutropenia | | | | | |
| n (%) | 50 (58.8%) | 55 (65.5%) | 105 (62.1%) | 50 (58.1%) | |
| NEUG 50 mg - NEUG 40 mg | | | | | (−7.94; 21.24) |
| NEUG 40 mg - Pegfilgrastim | | | | | (−14.09; 15.45) |
| NEUG 50 mg - Pegfilgrastim | | | | | (−7.23; 21.90) |
| Duration (days) of severe neutropenia | | | | | |
| n | 84 | 84 | 168 | 86 | |
| Mean (SD) | 1.0 (1.09) | 1.3 (1.22) | 1.2 (1.16) | 1.2 (1.34) | |
| Median | 1 | 1 | 1 | 1 | |
| Min/Max | 0/4 | 0/5 | 0/5 | 0/5 | |
| | | | | | 95% CI |
| NEUG 50 mg - NEUG 40 mg | | | | | (−0.07; 0.58) |
| NEUG 40 mg - Pegfilgrastim | | | | | (−0.57; 0.15) |
| NEUG 50 mg - Pegfilgrastim | | | | | (−0.31; 0.41) |
| | | | | | 97.5% CI |
| NEUG 50 mg - NEUG 40 mg | | | | | (−0.12; 0.63) |
| NEUG 40 mg - Pegfilgrastim | | | | | (−0.62; 0.21) |
| NEUG 50 mg - Pegfilgrastim | | | | | (−0.37; 0.46) |

The incidence of severe neutropenia ranged from 58.1% in the pegfilgrastim group to 65.5% in the NEUG 50 mg group. The treatment effect was not statistically significant (p=0.559). The treatment groups were comparable for Cycle 1 DSN, with mean values of 1.0, 1.3, and 1.2 days for the NEUG 40 mg, NEUG 50 mg, and pegfilgrastim groups, respectively. The 95% and 97.5% two-sided confidence intervals for differences between NEUG and pegfilgrastim were strictly less than 1 day for both NEUG doses. This analysis established non-inferiority of NEUG to pegfilgrastim. Across treatment cycles, the incidences of severe neutropenia and Grade 3 or 4 neutropenia were lower in Cycles 2-4 than in Cycle 1. The mean DSN and mean duration of Grade 3 or 4 neutropenia were smaller in Cycles 2-4 than in Cycle 1. Within treatment cycles, the treatments were similar, and treatment effect was not significantly different for any of these parameters in any chemotherapy cycle.

The DSN were compared in patients grouped into weight quartiles to determine if the fixed doses of NEUG provided adequate support for patients of all weights. These results show that all weight groups were adequately supported, as there is no significant difference in the mean DSN among weight subgroups (Table 24).

TABLE 24

Cycle 1 duration of sever neutropenia (in days), by weight
Baseline weight (kg)

| | | 40-62 | 63-71 | 72-80 | 81-127 |
|---|---|---|---|---|---|
| Pegfilgrastim 6 mg | Mean (SD) | 1.1 (1.3) | 1.3 (1.4) | 1.5 (1.6) | 1.0 (1.0) |
| | N | 16 | 21 | 26 | 23 |
| Neugranin 40 mg | Mean (SD) | 1.0 (1.0) | 1.0 (1.2) | 0.9 (1.0) | 1.4 (1.4) |
| | N | 22 | 21 | 21 | 21 |
| Neugranin 50 mg | Mean (SD) | 1.3 (1.1) | 1.0 (1.4) | 1.4 (1.3) | 1.5 (1.1) |
| | N | 15 | 26 | 20 | 23 |

Febrile neutropenia is summarized for all cycles in Table 25. During Cycle 1, the proportion of subjects experiencing febrile neutropenia was 2 subjects (3.5%), 5 subjects (6.0%), and 2 subjects (2.3%) in the NEUG 40 mg, NEUG 50 mg, and pegfilgrastim groups, respectively. Febrile neutropenia was observed for only three additional subjects during Cycles 2-4, 2 subjects in the NEUG 40 mg group and 1 subject in the pegfilgrastim group. The treatment effect was not statistically significant in any chemotherapy cycle.

TABLE 25

Incidence of febrile neutropenia in cycles 1-4

| Treatment | Overall | Cycle 1 | Cycle 2 | Cycle 3 | Cycle 4 |
|---|---|---|---|---|---|
| Neugranin 40 mg | 4.7% (4/85) | 3.5% | 0.0% | 2.4% | 0.0% |
| Neugranin 50 mg | 6.0% (5/85) | 6.0% | 0.0% | 0.0% | 0.0% |
| Pegfilgrastim | 3.5% (3/86) | 2.3% | 0.0% | 0.0% | 1.2% |

There were no significant differences between treatments for duration of sever neutropenia in cycles 2-4 (Table 26).

TABLE 26

Mean duration of severe neutropenia in cycles 2-4

| Treatment | Cycle 2 | Cycle 3 | Cycle 4 |
|---|---|---|---|
| Neugranin 40 mg | 0.5 | 0.4 | 0.4 |
| Neugranin 50 mg | 0.4 | 0.5 | 0.6 |
| Pegfilgrastim | 0.5 | 0.4 | 0.6 |

The mean time to ANC recovery ($>1.5 \times 10^9$/L) was 2.0, 2.1, and 2.6 days for the Neugranin 40 mg, NEUG 50 mg, and pegfilgrastim groups, respectively (Table 27). There were no significant differences between treatment groups for the depth of ANC nadir or time to nadir.

TABLE 27

ANC nadir, time to ANC nadir and time to recovery

| | Neugranin | | | | | |
|---|---|---|---|---|---|---|
| Parameter | 40 mg (N = 85) | 50 mg (N = 84) | All Neug. N = 169 | Pegfilgrastim (N = 86) | 95% CI | p-value |
| Nadir ANC ($10^9$/L) | | | | | | |
| n | 85 | 84 | 169 | 86 | | 0.423 |
| Mean (SD) | 0.7 (0.88) | 0.6 (0.68) | 0.6 (0.79) | 0.7 (1.04) | | |
| Median | 0 | 0 | 0 | 0 | | |
| Min/Max | 0/5 | 0/3 | 0/5 | 0/7 | | |
| Time (days) to Nadir ANC | | | | | | |
| n | 85 | 84 | 169 | 86 | | 0.610 |
| Mean (SD) | 604 (1.38) | 6.7 (2.62) | 6.5 (2.09) | 6.5 (2.05) | | |
| Median | 6 | 6 | 6 | 6 | | |
| Min/Max | 5/18 | 5/20 | 5/20 | 4/17 | | |
| Time (days to ANC recover >1500 | | | | | | |
| N | 71 | 73 | 144 | 72 | | 0.005 |
| Mean (SD) | 2.0 (0.94) | 2.1 (1.03) | 2.0 (0.98) | 2.6 (1.23) | | |
| Median | 2 | 2 | 2 | 2 | | |
| Min/Max | 1/6 | 1/6 | 1/6 | 1/6 | | |

TABLE 27-continued

ANC nadir, time to ANC nadir and time to recovery

| Parameter | Neugranin | | | Pegfilgrastim (N = 86) | 95% CI | p-value |
|---|---|---|---|---|---|---|
| | 40 mg (N = 85) | 50 mg (N = 84) | All Neug. N = 169 | | | |
| Treatment comparisons | | | | | | |
| NEUG 50 mg - NEUG 40 mg | | | | | (−0.31; 0.39) | |
| NEUG 40 mg - Pegfilgrastim | | | | | (−0.88; −0.17) | |
| NEUG 50 mg - Pegfilgrastim | | | | | (−0.84; −0.13) | | d. Pharmacokinetics of Phase II, Part B

Serum Neugranin concentrations were determined using a validated sandwich ELISA with a lower limit of quantification (LLQ) of 6.312 ng/mL. Pharmacokinetic parameters were calculated using noncompartmental modeling techniques, with the exception of the absorption half-life, which was determined using a first-order absorption, first-order elimination one-compartment model. Modeling was performed with WinNonlin Professional (version 5.0.1). Serum NEUG concentrations were determined in chemotherapy Cycle 1 in all subjects treated with NEUG in Phase II. In the Part A of Phase II, the median elimination half-life of NEUG was 33 hours in the 30 mg dose group, 46 hours in the 40 mg dose group, and 18 hours in the 50 mg dose group (Table 28). In Part B, the median elimination half-life of NEUG was 40 hours for 40 mg dose group, and 39 hours for the 50 mg dose group (Table 29). During the Part A, PK sampling was more frequent (pre-dose, 3 h, 6 h, 12 h, 24 h Day 3, Day 5-9, Day 11) than for Part B (pre-dose, Day 3, Day 5-8).

TABLE 28

Median elimination half-life by treatment, Phase II, Part A

| | NEUG 30 mg | NEUG 40 mg | NEUG 50 mg | Pegfilgrastim 6 mg |
|---|---|---|---|---|
| Number of subjects | 10 | 20 | 20 | 26 |
| Number of subjects evaluated for elimination half-life | 3 | 12 | 16 | 19 |
| Median half-life (hr) | 33 | 46 | 18 | 40 |

TABLE 29

Median elimination half-life by treatment, Phase II, Part B

| | NEUG 40 mg | NEUG 50 mg | Pegfilgrastim 6 mg |
|---|---|---|---|
| Number of subjects | 85 | 84 | 84 |
| Number of subjects evaluated for elimination half-life | 48 | 54 | 52 |
| Median half-life (hr) | 40 | 39 | 50 |

Serum pegfilgrastim concentrations were determined using a validated sandwich ELISA in chemotherapy Cycle 1 in all subjects treated with pegfilgrastim in Phase II. In Part A, the median elimination half-life of pegfilgrastim was about 40 hours. In Part B, the median elimination half-life of pegfilgrastim was about 50 hours. The elimination half-life is reported to be 3-4 hours for filgrastim and 42-67.5 hours (depending on dose) for pegfilgrastim.

e. Immunogenicity

Among the study participants, there was one confirmed anti-G-CSF/neoepitope antibody response in the Neugranin-treated subjects and one anti-G-CSF response in the pegfilgrastim-treated group, or 0.5% and 0.9%, respectively (Table 30). In both cases, the subjects had elevated non-specific binding in pre-dose samples.

TABLE 30

Summary of G-CSF specific treatment emergent immune responses to NEUG and Pegfilgrastim

| | NEUG Positive response/number of subjects | Pegfilgrastim Positive response/ number of subjects |
|---|---|---|
| Phase II, Part A (4 cycles maximum) | 0/50 | 0/26 |
| Phase II, Part B (4 cycles maximum) | 1/169 | 1/86 |
| Total number of subjects | 1/219 | 1/112 |

After NEUG treatment, very low levels of confirmed positive antibodies were seen in the patient, with no apparent increase in the magnitude of the response after repeated doses (data not shown). In the pegfilgrastim-treated patient, an unusually high non-specific background binding was observed; however, only a transient confirmed antibody response was seen after Cycle 2 treatment (data not shown). No antibody response was neutralizing.

Anti-HSA antibodies were naturally occurring at a low level in this population, with 6.9% of the subjects testing positive for HSA antibodies in the pre-dose evaluation. Treatment emergent anti-HSA antibodies were observed in four NEUG-treated subjects, 1.8% (Table 31). All responses were transient and weak. Three responses emerged after the first treatment cycle and were undetectable after Cycles 2, 3 and 4. One response occurred after the third treatment but was undetectable at the 30 day follow-up after the 4th treatment (data not shown).

TABLE 31

Summary of HSA-specific treatment emergent immune responses to NEUG

| | NEUG Positive response/number of subjects |
|---|---|
| Phase II, Part A (4 cycles maximum) | 0/50 |

TABLE 31-continued

Summary of HSA-specific treatment emergent immune responses to NEUG

| | NEUG Positive response/number of subjects |
|---|---|
| Phase II, Part B (4 cycles maximum) | 4/169 |
| Total number of subjects | 4/219 | f. Treatment-Emergent Adverse Events in Phase II, Part B

In Phase II, Part B, ≧90% of subjects in each treatment group experienced at least one treatment-emergent adverse event (TEAE), and the percent of subjects with at least one TEAE related to study medication ranged from 23.1% in the pegfilgrastim group to 35.0% in the Neugranin 50 mg group. The percent of subjects with at least one SAE was highest in the NEUG 30 mg group (30%), but was approximately 15% in the other three treatment groups. None of the SAEs were related to study medication. One patient (NEUG 30 mg) was withdrawn from the study due to diabetic foot, which was considered to be not related to study medication. In the Part B, all except 8 subjects (2 NEUG 40 mg, 3 NEUG 50 mg, 3 pegfilgrastim) had at least one TEAE. The percent of subjects with at least one TEAE related to study medication was 20.2% in the NEUG 50 mg group, 22.4% in the NEUG 40 mg group and 22.1% in subjects receiving pegfilgrastim. Two subjects (1 NEUG 40 mg, 1 pegfilgrastim) died during the study, and 6-8 subjects in each treatment group experienced at least one SAE. No deaths or SAEs were considered to be related to study medication.

The total number of TEAEs was similar across treatment groups in Part A, when sample size is taken into consideration for the NEUG 30 mg dose, and in Part B. In both Parts A and B, the percent of TEAEs with CTC Grade 3 or higher was similar for NEUG and pegfilgrastim as was the percent of TEAEs related to study medication.

g. Dose Response

The results of Phase II demonstrated that both 40 and 50 mg fixed doses of NEUG provided equivalent safety and efficacy to 6 mg of pegfilgrastim in breast cancer subjects treated with myelotoxic chemotherapy. While the mean DSN for the 40 mg treatment group was slightly lower than the mean DSN of the 50 mg group, these differences were not statistically significant. A dose response was observed for $AUC_{ANC}$ (Days 0-15 in cycle 1) both when weight-adjusted dose was considered and for fixed dose cohorts (FIG. 24). The $AUC_{ANC}$ for the 30 mg cohort was slightly lower than that of pegfilgrastim, indicating that the 30 mg fixed dose was less effective in this study, whereas $AUC_{ANC}$ for the 40 mg and the 50 mg cohorts were dose-related and higher (although not significantly) than the $AUC_{ANC}$ for pegfilgrastim treated subjects. From the above analysis, a dose response is apparent when NEUG is administered on a weight adjusted basis (mg/kg). However, comparison of DSN in cycle 1 for Phase II, Part B suggested that patients of all weight quartiles were adequately supported as DSN did not vary significantly among the treatment arms (40 and 50 mg NEUG and pegfilgrastim) nor with weight-adjusted dose (mg/kg). Further, there was no evidence that a fixed dose might result in an altered safety profile in lighter patients as the incidence and severity of related adverse events (bone pain in particular; data not shown) did not correlate with dose received per kilogram body weight, nor were they different from those with pegfilgrastim.

Example 12

Additional Exemplary NEUG Formulations

Development of additional NEUG formulations was undertaken to analyze and determine the effects of pH (4-7), buffer species (L-histidine, citrate, acetate), tonicifiers (sorbitol vs. NaCl), and protein concentration (concentrated up to 70-90 mg/ml). Samples were analyzed/monitored via SEC (monomer %), RH-HPLC (purity %), Ellman's assay (—SH amount), A280 (protein), and IE-HPLC (charge isoforms). The formulations examined are presented in Table 32, below.

After testing, formulations A40S, A45S, C55N and C55S appeared the most stable (in explored aspects).

TABLE 32

Additional NEUG formulations

| Code | Buffer | pH | Tonicifier (q.s. to isotonic) |
|---|---|---|---|
| H60N | 25 mM L-Histidine | 6.0 | NaCl |
| H60S | 25 mM L-Histidine | 6.0 | Sorbitol |
| H55N | 25 mM L-Histidine | 5.5 | NaCl |
| H55S | 25 mM L-Histidine | 5.5 | Sorbitol |
| C55N | 25 mM citrate | 5.5 | NaCl |
| C55S | 25 mM citrate | 5.5 | Sorbitol |
| C50N | 25 mM citrate | 5.0 | NaCl |
| C50S | 25 mM citrate | 5.0 | Sorbitol |
| C45N | 25 mM citrate | 4.5 | NaCl |
| C45S | 25 mM citrate | 4.5 | Sorbitol |
| A45N | 25 mM acetate | 4.5 | NaCl |
| A45S | 25 mM acetate | 4.5 | Sorbitol |
| A40N | 25 mM acetate | 4.0 | NaCl |
| A40S | 25 mM acetate | 4.0 | Sorbitol |

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

SEQUENCE LISTING

<160> NUMBER OF SEQ ID NOS: 6

<210> SEQ ID NO 1
<211> LENGTH: 6
<212> TYPE: PRT
<213> ORGANISM: Unknown
<220> FEATURE:
<223> OTHER INFORMATION: Description of Unknown: HSA pro-peptide sequence

```
<400> SEQUENCE: 1

Arg Gly Val Phe Arg Arg
1               5

<210> SEQ ID NO 2
<211> LENGTH: 6
<212> TYPE: PRT
<213> ORGANISM: Unknown
<220> FEATURE:
<223> OTHER INFORMATION: Description of Unknown: Yeast sequence

<400> SEQUENCE: 2

Arg Ser Leu Asp Lys Arg
1               5

<210> SEQ ID NO 3
<211> LENGTH: 2277
<212> TYPE: DNA
<213> ORGANISM: Homo sapiens
<220> FEATURE:
<221> NAME/KEY: CDS
<222> LOCATION: (1)..(2277)

<400> SEQUENCE: 3 gat gca cac aag agt gag gtt gct cat cgg ttt aaa gat ttg gga gaa      48
Asp Ala His Lys Ser Glu Val Ala His Arg Phe Lys Asp Leu Gly Glu
1               5                   10                  15 gaa aat ttc aaa gcc ttg gtg ttg att gcc ttt gct cag tat ctt cag      96
Glu Asn Phe Lys Ala Leu Val Leu Ile Ala Phe Ala Gln Tyr Leu Gln
            20                  25                  30 cag tgt cca ttt gaa gat cat gta aaa tta gtg aat gaa gta act gaa     144
Gln Cys Pro Phe Glu Asp His Val Lys Leu Val Asn Glu Val Thr Glu
        35                  40                  45 ttt gca aaa aca tgt gtt gct gat gag tca gct gaa aat tgt gac aaa     192
Phe Ala Lys Thr Cys Val Ala Asp Glu Ser Ala Glu Asn Cys Asp Lys
    50                  55                  60 tca ctt cat acc ctt ttt gga gac aaa tta tgc aca gtt gca act ctt     240
Ser Leu His Thr Leu Phe Gly Asp Lys Leu Cys Thr Val Ala Thr Leu
65                  70                  75                  80 cgt gaa acc tat ggt gaa atg gct gac tgc tgt gca aaa caa gaa cct     288
Arg Glu Thr Tyr Gly Glu Met Ala Asp Cys Cys Ala Lys Gln Glu Pro
                85                  90                  95 gag aga aat gaa tgc ttc ttg caa cac aaa gat gac aac cca aac ctc     336
Glu Arg Asn Glu Cys Phe Leu Gln His Lys Asp Asp Asn Pro Asn Leu
            100                 105                 110 ccc cga ttg gtg aga cca gag gtt gat gtg atg tgc act gct ttt cat     384
Pro Arg Leu Val Arg Pro Glu Val Asp Val Met Cys Thr Ala Phe His
        115                 120                 125 gac aat gaa gag aca ttt ttg aaa aaa tac tta tat gaa att gcc aga     432
Asp Asn Glu Glu Thr Phe Leu Lys Lys Tyr Leu Tyr Glu Ile Ala Arg
    130                 135                 140 aga cat cct tac ttt tat gcc ccg gaa ctc ctt ttc ttt gct aaa agg     480
Arg His Pro Tyr Phe Tyr Ala Pro Glu Leu Leu Phe Phe Ala Lys Arg
145                 150                 155                 160 tat aaa gct gct ttt aca gaa tgt tgc caa gct gct gat aaa gct gcc     528
Tyr Lys Ala Ala Phe Thr Glu Cys Cys Gln Ala Ala Asp Lys Ala Ala
                165                 170                 175 tgc ctg ttg cca aag ctc gat gaa ctt cgg gat gaa ggg aag gct tcg     576
Cys Leu Leu Pro Lys Leu Asp Glu Leu Arg Asp Glu Gly Lys Ala Ser
            180                 185                 190 tct gcc aaa cag aga ctc aag tgt gcc agt ctc caa aaa ttt gga gaa     624
Ser Ala Lys Gln Arg Leu Lys Cys Ala Ser Leu Gln Lys Phe Gly Glu
```

-continued

```
            195                 200                 205
aga gct ttc aaa gca tgg gca gta gct cgc ctg agc cag aga ttt ccc      672
Arg Ala Phe Lys Ala Trp Ala Val Ala Arg Leu Ser Gln Arg Phe Pro
    210                 215                 220 aaa gct gag ttt gca gaa gtt tcc aag tta gtg aca gat ctt acc aaa      720
Lys Ala Glu Phe Ala Glu Val Ser Lys Leu Val Thr Asp Leu Thr Lys
225                 230                 235                 240 gtc cac acg gaa tgc tgc cat gga gat ctg ctt gaa tgt gct gat gac      768
Val His Thr Glu Cys Cys His Gly Asp Leu Leu Glu Cys Ala Asp Asp
            245                 250                 255 agg gcg gac ctt gcc aag tat atc tgt gaa aat caa gat tcg atc tcc      816
Arg Ala Asp Leu Ala Lys Tyr Ile Cys Glu Asn Gln Asp Ser Ile Ser
    260                 265                 270 agt aaa ctg aag gaa tgc tgt gaa aaa cct ctg ttg gaa aaa tcc cac      864
Ser Lys Leu Lys Glu Cys Cys Glu Lys Pro Leu Leu Glu Lys Ser His
275                 280                 285 tgc att gcc gaa gtg gaa aat gat gag atg cct gct gac ttg cct tca      912
Cys Ile Ala Glu Val Glu Asn Asp Glu Met Pro Ala Asp Leu Pro Ser
290                 295                 300 tta gct gct gat ttt gtt gaa agt aag gat gtt tgc aaa aac tat gct      960
Leu Ala Ala Asp Phe Val Glu Ser Lys Asp Val Cys Lys Asn Tyr Ala
305                 310                 315                 320 gag gca aag gat gtc ttc ctg ggc atg ttt ttg tat gaa tat gca aga     1008
Glu Ala Lys Asp Val Phe Leu Gly Met Phe Leu Tyr Glu Tyr Ala Arg
            325                 330                 335 agg cat cct gat tac tct gtc gtg ctg ctg aga ctt gcc aag aca         1056
Arg His Pro Asp Tyr Ser Val Val Leu Leu Leu Arg Leu Ala Lys Thr
    340                 345                 350 tat gaa acc act cta gag aag tgc tgt gcc gct gca gat cct cat gaa     1104
Tyr Glu Thr Thr Leu Glu Lys Cys Cys Ala Ala Ala Asp Pro His Glu
355                 360                 365 tgc tat gcc aaa gtg ttc gat gaa ttt aaa cct ctt gtg gaa gag cct     1152
Cys Tyr Ala Lys Val Phe Asp Glu Phe Lys Pro Leu Val Glu Glu Pro
370                 375                 380 cag aat tta atc aaa caa aat tgt gag ctt ttt gag cag ctt gga gag     1200
Gln Asn Leu Ile Lys Gln Asn Cys Glu Leu Phe Glu Gln Leu Gly Glu
385                 390                 395                 400 tac aaa ttc cag aat gcg cta tta gtt cgt tac acc aag aaa gta ccc     1248
Tyr Lys Phe Gln Asn Ala Leu Leu Val Arg Tyr Thr Lys Lys Val Pro
            405                 410                 415 caa gtg tca act cca act ctt gta gag gtc tca aga aac cta gga aaa     1296
Gln Val Ser Thr Pro Thr Leu Val Glu Val Ser Arg Asn Leu Gly Lys
    420                 425                 430 gtg ggc agc aaa tgt tgt aaa cat cct gaa gca aaa aga atg ccc tgt     1344
Val Gly Ser Lys Cys Cys Lys His Pro Glu Ala Lys Arg Met Pro Cys
435                 440                 445 gca gaa gac tat cta tcc gtg gtc ctg aac cag tta tgt gtg ttg cat     1392
Ala Glu Asp Tyr Leu Ser Val Val Leu Asn Gln Leu Cys Val Leu His
450                 455                 460 gag aaa acg cca gta agt gac aga gtc acc aaa tgc tgc aca gaa tcc     1440
Glu Lys Thr Pro Val Ser Asp Arg Val Thr Lys Cys Cys Thr Glu Ser
465                 470                 475                 480 ttg gtg aac agg cga cca tgc ttt tca gct ctg gaa gtc gat gaa aca     1488
Leu Val Asn Arg Arg Pro Cys Phe Ser Ala Leu Glu Val Asp Glu Thr
            485                 490                 495 tac gtt ccc aaa gag ttt aat gct gaa aca ttc acc ttc cat gca gat     1536
Tyr Val Pro Lys Glu Phe Asn Ala Glu Thr Phe Thr Phe His Ala Asp
    500                 505                 510 ata tgc aca ctt tct gag aag gag aga caa atc aag aaa caa act gca     1584
Ile Cys Thr Leu Ser Glu Lys Glu Arg Gln Ile Lys Lys Gln Thr Ala
```

```
                515                 520                 525
ctt gtt gag ctc gtg aaa cac aag ccc aag gca aca aaa gag caa ctg      1632
Leu Val Glu Leu Val Lys His Lys Pro Lys Ala Thr Lys Glu Gln Leu
    530                 535                 540 aaa gct gtt atg gat gat ttc gca gct ttt gta gag aag tgc tgc aag      1680
Lys Ala Val Met Asp Asp Phe Ala Ala Phe Val Glu Lys Cys Cys Lys
545                 550                 555                 560 gct gac gat aag gag acc tgc ttt gcc gag gag ggt aaa aaa ctt gtt      1728
Ala Asp Asp Lys Glu Thr Cys Phe Ala Glu Glu Gly Lys Lys Leu Val
                565                 570                 575 gct gca agt caa gct gcc tta ggc tta acc ccc ctg ggc cct gcc agc      1776
Ala Ala Ser Gln Ala Ala Leu Gly Leu Thr Pro Leu Gly Pro Ala Ser
            580                 585                 590 tcc ctg ccc cag agc ttc ctg ctc aag tgc tta gag caa gtg agg aag      1824
Ser Leu Pro Gln Ser Phe Leu Leu Lys Cys Leu Glu Gln Val Arg Lys
        595                 600                 605 atc cag ggc gat ggc gca gcg ctc cag gag aag ctg tgt gcc acc tac      1872
Ile Gln Gly Asp Gly Ala Ala Leu Gln Glu Lys Leu Cys Ala Thr Tyr
    610                 615                 620 aag ctg tgc cac ccc gag gag ctg gtg ctg ctc gga cac tct ctg ggc      1920
Lys Leu Cys His Pro Glu Glu Leu Val Leu Leu Gly His Ser Leu Gly
625                 630                 635                 640 atc ccc tgg gct ccc ctg agc agc tgc ccc agc cag gcc ctg cag ctg      1968
Ile Pro Trp Ala Pro Leu Ser Ser Cys Pro Ser Gln Ala Leu Gln Leu
                645                 650                 655 gca ggc tgc ttg agc caa ctc cat agc ggc ctt ttc ctc tac cag ggg      2016
Ala Gly Cys Leu Ser Gln Leu His Ser Gly Leu Phe Leu Tyr Gln Gly
            660                 665                 670 ctc ctg cag gcc ctg gaa ggg atc tcc ccc gag ttg ggt ccc acc ttg      2064
Leu Leu Gln Ala Leu Glu Gly Ile Ser Pro Glu Leu Gly Pro Thr Leu
        675                 680                 685 gac aca ctg cag ctg gac gtc gcc gac ttt gcc acc acc atc tgg cag      2112
Asp Thr Leu Gln Leu Asp Val Ala Asp Phe Ala Thr Thr Ile Trp Gln
    690                 695                 700 cag atg gaa gaa ctg gga atg gcc cct gcc ctg cag ccc acc cag ggt      2160
Gln Met Glu Glu Leu Gly Met Ala Pro Ala Leu Gln Pro Thr Gln Gly
705                 710                 715                 720 gcc atg ccg gcc ttc gcc tct gct ttc cag cgc cgg gca gga ggg gtc      2208
Ala Met Pro Ala Phe Ala Ser Ala Phe Gln Arg Arg Ala Gly Gly Val
                725                 730                 735 ctg gtt gcc tcc cat ctg cag agc ttc ctg gag gtg tcg tac cgc gtt      2256
Leu Val Ala Ser His Leu Gln Ser Phe Leu Glu Val Ser Tyr Arg Val
            740                 745                 750 cta cgc cac ctt gcc cag ccc                                          2277
Leu Arg His Leu Ala Gln Pro
        755

<210> SEQ ID NO 4
<211> LENGTH: 759
<212> TYPE: PRT
<213> ORGANISM: Homo sapiens

<400> SEQUENCE: 4

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
```

```
            50                  55                  60
Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480
```

-continued

Leu Val Asn Arg Arg Pro Cys Phe Ser Ala Leu Glu Val Asp Glu Thr
            485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
            565                 570                 575

Ala Ala Ser Gln Ala Ala Leu Gly Leu Thr Pro Leu Gly Pro Ala Ser
            580                 585                 590

Ser Leu Pro Gln Ser Phe Leu Leu Lys Cys Leu Glu Gln Val Arg Lys
            595                 600                 605

Ile Gln Gly Asp Gly Ala Ala Leu Gln Glu Lys Leu Cys Ala Thr Tyr
            610                 615                 620

Lys Leu Cys His Pro Glu Glu Leu Val Leu Leu Gly His Ser Leu Gly
625                 630                 635                 640

Ile Pro Trp Ala Pro Leu Ser Ser Cys Pro Ser Gln Ala Leu Gln Leu
            645                 650                 655

Ala Gly Cys Leu Ser Gln Leu His Ser Gly Leu Phe Leu Tyr Gln Gly
            660                 665                 670

Leu Leu Gln Ala Leu Glu Gly Ile Ser Pro Glu Leu Gly Pro Thr Leu
            675                 680                 685

Asp Thr Leu Gln Leu Asp Val Ala Asp Phe Ala Thr Thr Ile Trp Gln
            690                 695                 700

Gln Met Glu Glu Leu Gly Met Ala Pro Ala Leu Gln Pro Thr Gln Gly
705                 710                 715                 720

Ala Met Pro Ala Phe Ala Ser Ala Phe Gln Arg Arg Ala Gly Gly Val
            725                 730                 735

Leu Val Ala Ser His Leu Gln Ser Phe Leu Glu Val Ser Tyr Arg Val
            740                 745                 750

Leu Arg His Leu Ala Gln Pro
            755

<210> SEQ ID NO 5
<211> LENGTH: 204
<212> TYPE: PRT
<213> ORGANISM: Homo sapiens

<400> SEQUENCE: 5

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
            35                  40                  45

Glu Gln Val Arg Lys Ile Gln Gly Asp Gly Ala Ala Leu Gln Glu Lys
            50                  55                  60

Leu Cys Ala Thr Tyr Lys Leu Cys His Pro Glu Glu Leu Val Leu Leu
65                  70                  75                  80

Gly His Ser Leu Gly Ile Pro Trp Ala Pro Leu Ser Ser Cys Pro Ser
            85                  90                  95

```
Gln Ala Leu Gln Leu Ala Gly Cys Leu Ser Gln Leu His Ser Gly Leu
            100                 105                 110

Phe Leu Tyr Gln Gly Leu Leu Gln Ala Leu Glu Gly Ile Ser Pro Glu
            115                 120                 125

Leu Gly Pro Thr Leu Asp Thr Leu Gln Leu Asp Val Ala Asp Phe Ala
130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala Ser Ala Phe Gln Arg
                165                 170                 175

Arg Ala Gly Gly Val Leu Val Ala Ser His Leu Gln Ser Phe Leu Glu
            180                 185                 190

Val Ser Tyr Arg Val Leu Arg His Leu Ala Gln Pro
            195                 200
```

<210> SEQ ID NO 6
<211> LENGTH: 609
<212> TYPE: PRT
<213> ORGANISM: Homo sapiens

<400> SEQUENCE: 6

```
Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
            115                 120                 125

His Lys Asp Asp Asn Pro Asn Leu Pro Arg Leu Val Arg Pro Glu Val
            130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
            195                 200                 205

Leu Arg Asp Glu Gly Lys Ala Ser Ser Ala Lys Gln Arg Leu Lys Cys
210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270
```

```
Asp Leu Leu Glu Cys Ala Asp Arg Ala Asp Leu Ala Lys Tyr Ile
        275                 280                 285

Cys Glu Asn Gln Asp Ser Ile Ser Ser Lys Leu Lys Glu Cys Cys
        290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
                340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
        370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
                420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
        450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
                500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
        530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
                580                 585                 590

Ala Glu Glu Gly Lys Lys Leu Val Ala Ala Ser Gln Ala Ala Leu Gly
        595                 600                 605

Leu
```

What is claimed is:

1. A pharmaceutical composition comprising recombinant human albumin-human granulocyte colony stimulating factor, and at least one pharmaceutically acceptable carrier, wherein the composition has a pH of between 4 and 6.4, wherein the concentration of recombinant human albumin-human granulocyte colony stimulating factor is between 30 and 120 mg/ml and wherein the monomeric purity in solution of the recombinant human albumin-human granulocyte colony stimulating factor decreases by less than 5% after incubation at 25° C. for 24 hours.

2. The pharmaceutical composition of claim 1 wherein the composition has a pH of about 6.0.

3. The pharmaceutical composition of claim 1 wherein the concentration of recombinant human albumin-human granulocyte colony stimulating factor is about 50 mg/ml.

4. The pharmaceutical composition of claim 1 comprising at least one pharmaceutically acceptable salt.

5. The pharmaceutical composition of claim 4 wherein the concentration of salt is between about 5 and about 50 mM.

6. The pharmaceutical composition of claim 1 comprising a pharmaceutically acceptable buffer.

7. The pharmaceutical composition of claim 6 wherein the concentration of buffer is between about 15 and about 50 mM.

8. The pharmaceutical composition of claim 6 wherein the concentration of buffer is about 20 mM.

9. The pharmaceutical composition of claim 6 wherein the buffer is a phosphate or a citrate.

10. The pharmaceutical composition of claim 9 wherein the buffer is sodium phosphate.

11. The pharmaceutical composition of claim 10 wherein the buffer comprises sodium phosphate monobasic or sodium phosphate dibasic.

12. The pharmaceutical composition of claim 1 comprising a freeze-drying stabilizer.

13. The pharmaceutical composition of claim 12 wherein the freeze-drying stabilizer comprises trehalose dihydrate.

14. The pharmaceutical composition of claim 13 wherein the concentration of trehalose dihydrate is about 60 mM.

15. The pharmaceutical composition of claim 1 comprising a bulking agent.

16. The pharmaceutical composition of claim 15 wherein the bulking agent comprises a poly-alcohol.

17. The pharmaceutical composition of claim 16 wherein the poly-alcohol comprises mannitol.

18. The pharmaceutical composition of claim 1 in the form of a lyophilized powder.

19. The pharmaceutical composition of claim 18 wherein the powder is stored in a vial.

20. The pharmaceutical composition of claim 1 wherein the composition is in the form of a liquid.

21. The pharmaceutical composition of claim 20, wherein the liquid is stored in a syringe.

22. The pharmaceutical composition according to claim 1 comprising:
(a) recombinant human albumin-human granulocyte colony stimulating factor,
(b) 20 mM sodium phosphate,
(c) 180 mm mannitol,
(d) 60 mM trehalose dihydrate, and
(e) polysorbate 80,
wherein the composition has a pH of about 6.0.

23. The pharmaceutical composition according to claim 1 comprising recombinant human albumin-human granulocyte colony stimulating factor and PMTT.

24. The pharmaceutical composition according to claim 1 comprising:
(a) recombinant human albumin-human granulocyte colony stimulating factor,
(b) about 15 to about 50 mM sodium phosphate,
(c) about 180 to about 200 mM mannitol,
(d) about 40 to about 80 mM trehalose dihydrate, and
(e) polysorbate 80,
wherein the composition has a pH of about 6.0.

25. A pharmaceutical composition comprising between about 30 and about 120 mg/ml recombinant human albumin-human granulocyte colony stimulating factor and at least one pharmaceutically acceptable carrier, wherein the composition has a pH of between 4 and 6.4, and wherein the monomer purity is at least 98.1% when measured by SE-HLPC.

26. The pharmaceutical composition of claim 1 comprising a polysorbate.

* * * * *